US010076654B2

(12) United States Patent
Fregoso et al.

(10) Patent No.: US 10,076,654 B2
(45) Date of Patent: Sep. 18, 2018

(54) ELECTRICAL DISCHARGE IRRIGATOR APPARATUS AND METHOD

(71) Applicant: AMERICAN EAGLE INSTRUMENTS, INC., Missoula, MT (US)

(72) Inventors: Gilbert Fregoso, Missoula, MT (US); Brad Heckerman, Missoula, MT (US); Yuval Charles Avniel, Missoula, MT (US)

(73) Assignee: Brad Heckerman, Kalispell, MT (US)

( * ) Notice: Subject to any disclaimer, the term of this patent is extended or adjusted under 35 U.S.C. 154(b) by 281 days.

(21) Appl. No.: 14/653,108

(22) PCT Filed: Sep. 20, 2013

(86) PCT No.: PCT/US2013/060943
§ 371 (c)(1),
(2) Date: Jun. 17, 2015

(87) PCT Pub. No.: WO2014/099064
PCT Pub. Date: Jun. 26, 2014

(65) Prior Publication Data
US 2015/0327963 A1    Nov. 19, 2015

Related U.S. Application Data

(63) Continuation-in-part of application No. PCT/US2012/070080, filed on Dec. 17, 2012.
(Continued)

(51) Int. Cl.
*A61C 5/40* (2017.01)
*A61N 1/04* (2006.01)
(Continued)

(52) U.S. Cl.
CPC .......... *A61N 1/0448* (2013.01); *A61B 18/042* (2013.01); *A61C 1/06* (2013.01);
(Continued)

(58) Field of Classification Search
CPC .......... A61N 1/04; A61N 1/0548; A61C 5/40; A61C 5/50; A61C 8/0007
See application file for complete search history.

(56) References Cited

U.S. PATENT DOCUMENTS 3,916,529 A * 11/1975 Mousseau .............. A61C 19/04
33/514
5,254,121 A 10/1993 Manevitz et al.
(Continued)

FOREIGN PATENT DOCUMENTS

WO       02085230 A2   10/2002
WO    2010052717 A1    5/2010

OTHER PUBLICATIONS

Extended European Search Report issued by the EPO for European Patent Application No. 13864734.2 dated Aug. 11, 2016.
(Continued)

*Primary Examiner* — Tammie K Marlen
(74) *Attorney, Agent, or Firm* — Heslin Rothenberg Farley & Mesiti P.C.

(57) ABSTRACT

An electrical discharge irrigation device and method is described. The device includes a power source to produce a first voltage, a circuit coupled to the power source to convert the first voltage to a second voltage, a discharge capacitor to receive the second voltage from the circuit, a transistor or controlled rectifier coupled to the discharge capacitor to receive the second voltage, and an output tip. This output tip is coupled to the transistor or controlled rectifier and includes an electrode located in an interior space of the output tip configured to receive a charge from the transistor
(Continued)

or controlled rectifier and to release an electric discharge, and a ground return. The ground return is an outside surface of the output tip and a space between the electrode and the ground return holds a conductive medium.

12 Claims, 41 Drawing Sheets

Related U.S. Application Data

(60) Provisional application No. 61/699,568, filed on Sep. 11, 2012.

(51) Int. Cl.

| | | |
|---|---|---|
| *A61N 1/32* | (2006.01) | |
| *A61B 18/04* | (2006.01) | |
| *A61C 1/06* | (2006.01) | |
| *A61C 3/00* | (2006.01) | |
| *A61C 17/02* | (2006.01) | |
| *A61C 17/20* | (2006.01) | |
| *A61C 19/06* | (2006.01) | |
| *A61C 1/07* | (2006.01) | |
| *A61C 3/03* | (2006.01) | |
| *A61N 1/05* | (2006.01) | |
| *A61N 1/44* | (2006.01) | |
| *A61N 5/06* | (2006.01) | |
| *A61C 17/16* | (2006.01) | |
| *A61N 1/30* | (2006.01) | |
| *A61C 5/50* | (2017.01) | |
| *A61L 2/00* | (2006.01) | |

(52) U.S. Cl.
CPC .................. *A61C 1/07* (2013.01); *A61C 3/00* (2013.01); *A61C 3/03* (2013.01); *A61C 5/40* (2017.02); *A61C 5/50* (2017.02); *A61C 17/0202* (2013.01); *A61C 17/16* (2013.01); *A61C 17/20* (2013.01); *A61C 19/063* (2013.01); *A61N 1/04* (2013.01); *A61N 1/0548* (2013.01); *A61N 1/306* (2013.01); *A61N 1/325* (2013.01); *A61N 1/44* (2013.01); *A61N 5/0603* (2013.01); *A61B 2217/007* (2013.01); *A61L 2/00* (2013.01); *A61N 2005/0606* (2013.01); *A61N 2005/0661* (2013.01); *F04C 2270/0421* (2013.01)

(56) References Cited

U.S. PATENT DOCUMENTS

| | | | |
|---|---|---|---|
| 7,276,063 B2 * | 10/2007 | Davison | A61B 18/042 606/32 |
| 7,678,069 B1 | 3/2010 | Baker et al. | |
| 2002/0058914 A1 | 5/2002 | Henniges et al. | |
| 2007/0129715 A1 | 6/2007 | Eggers et al. | |
| 2007/0208334 A1 | 9/2007 | Woloszko et al. | |
| 2007/0239156 A1 | 10/2007 | Palanker et al. | |
| 2008/0097425 A1 | 4/2008 | Truckai | |
| 2009/0143718 A1 | 6/2009 | Jiang et al. | |
| 2012/0237893 A1 | 9/2012 | Bergheim et al. | |

OTHER PUBLICATIONS

Jun. 23, 2015: International Report on Patentability for International Application No. PCT/US2013/060943.
International Search Report for PCT/US2013/060934 dated Dec. 18, 2015.
Supplementary European Search Report issued by the EPO for European Patent Application No. 14846176.7 dated Jun. 1, 2017.

* cited by examiner

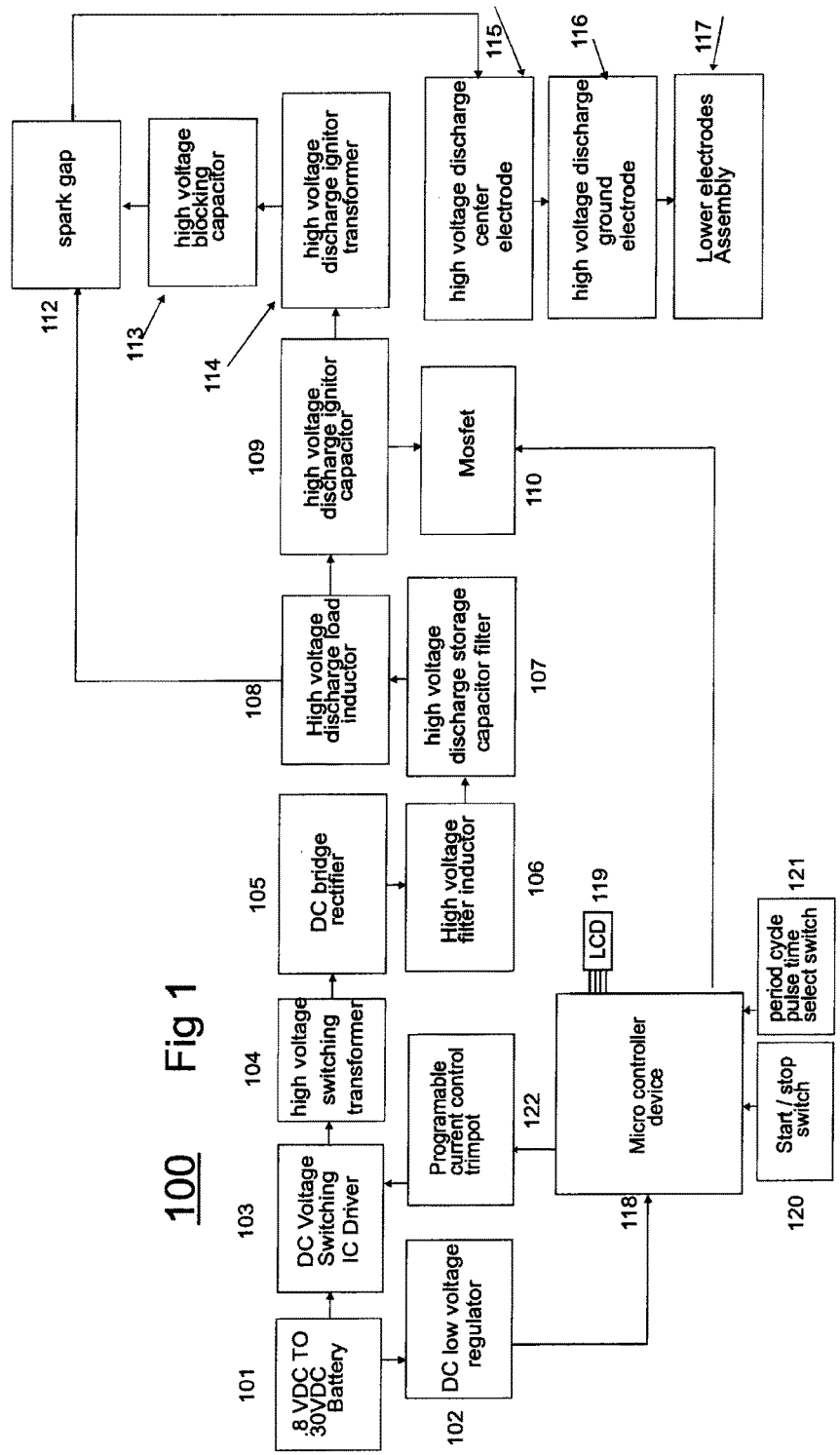

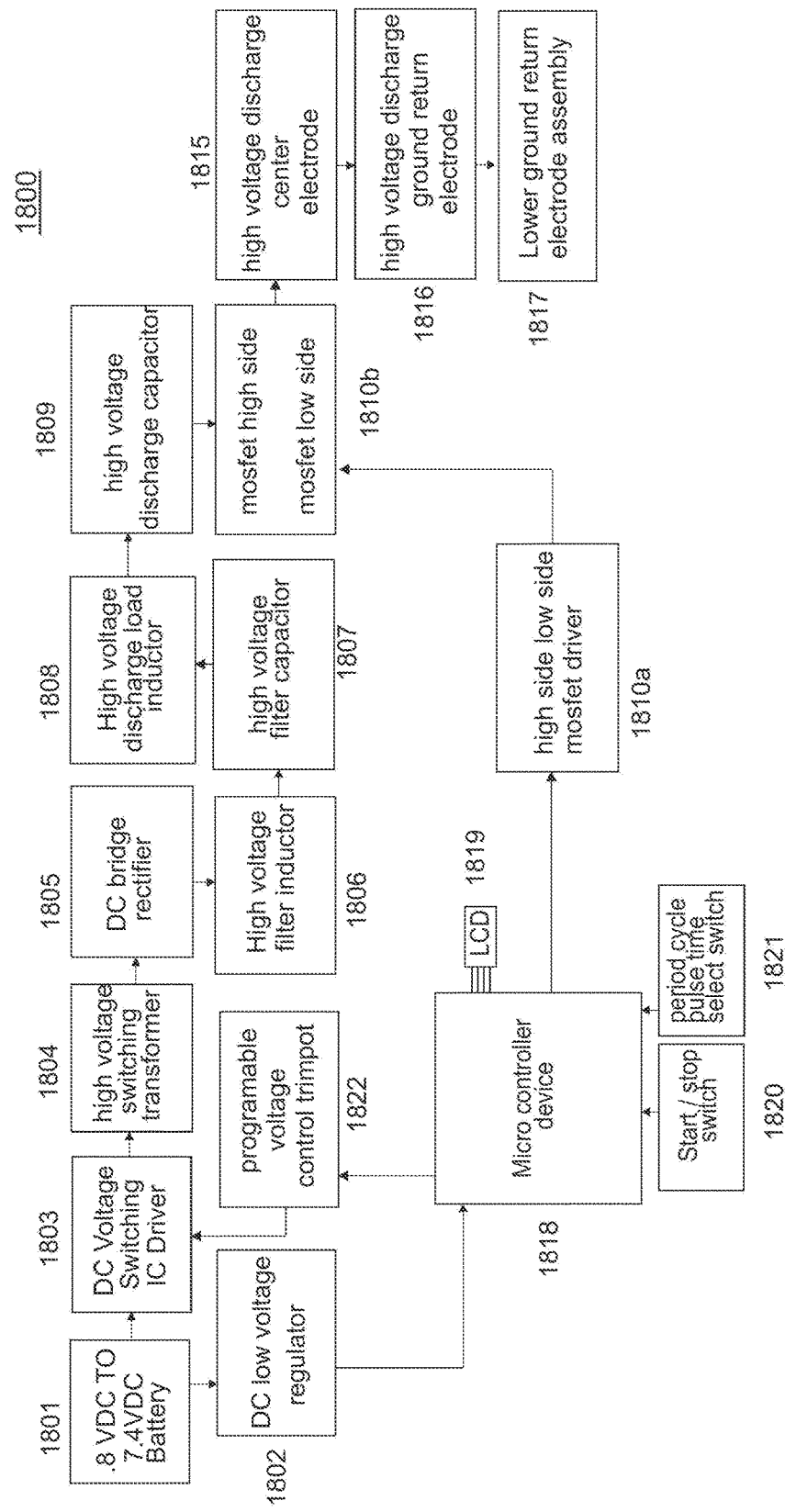

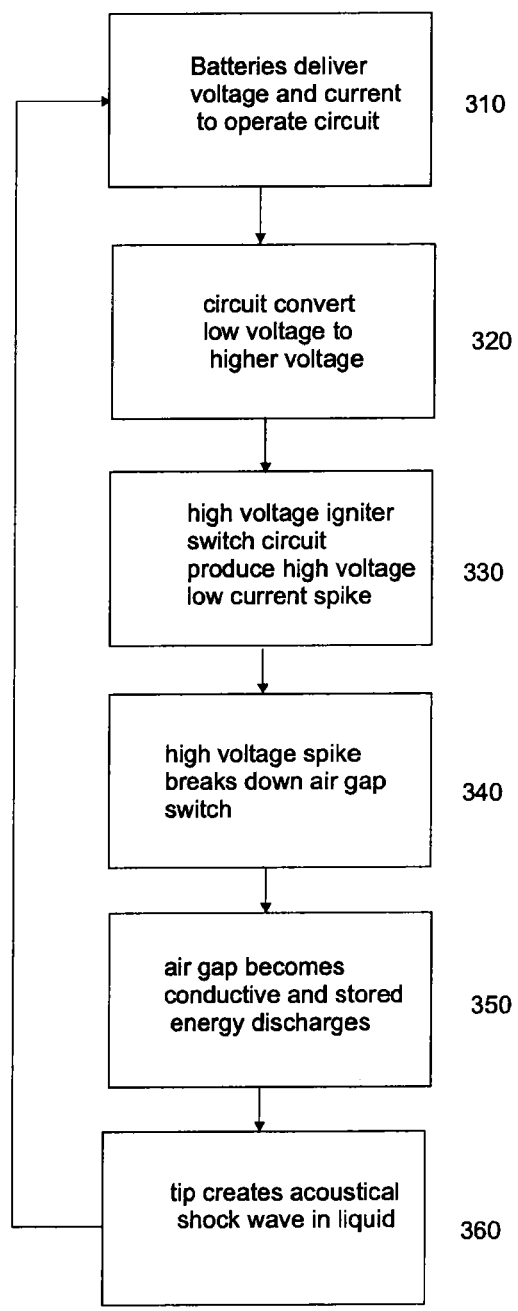

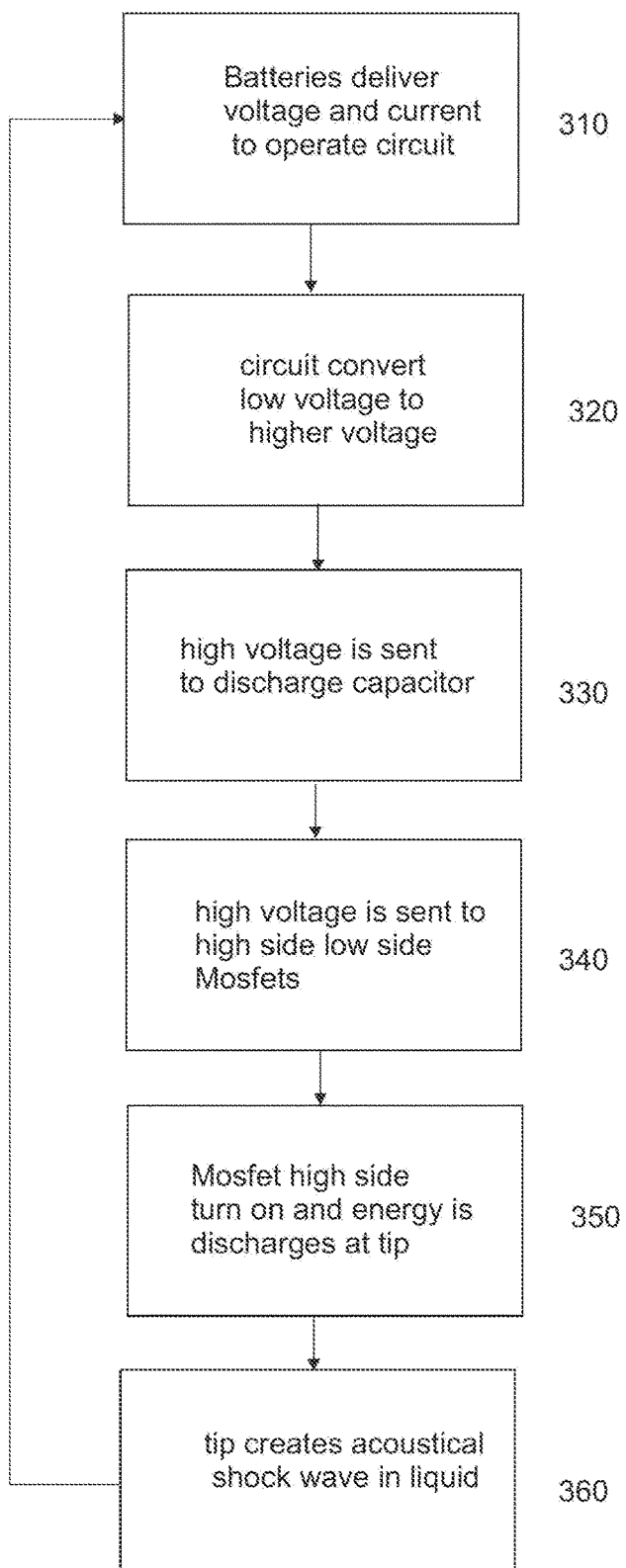

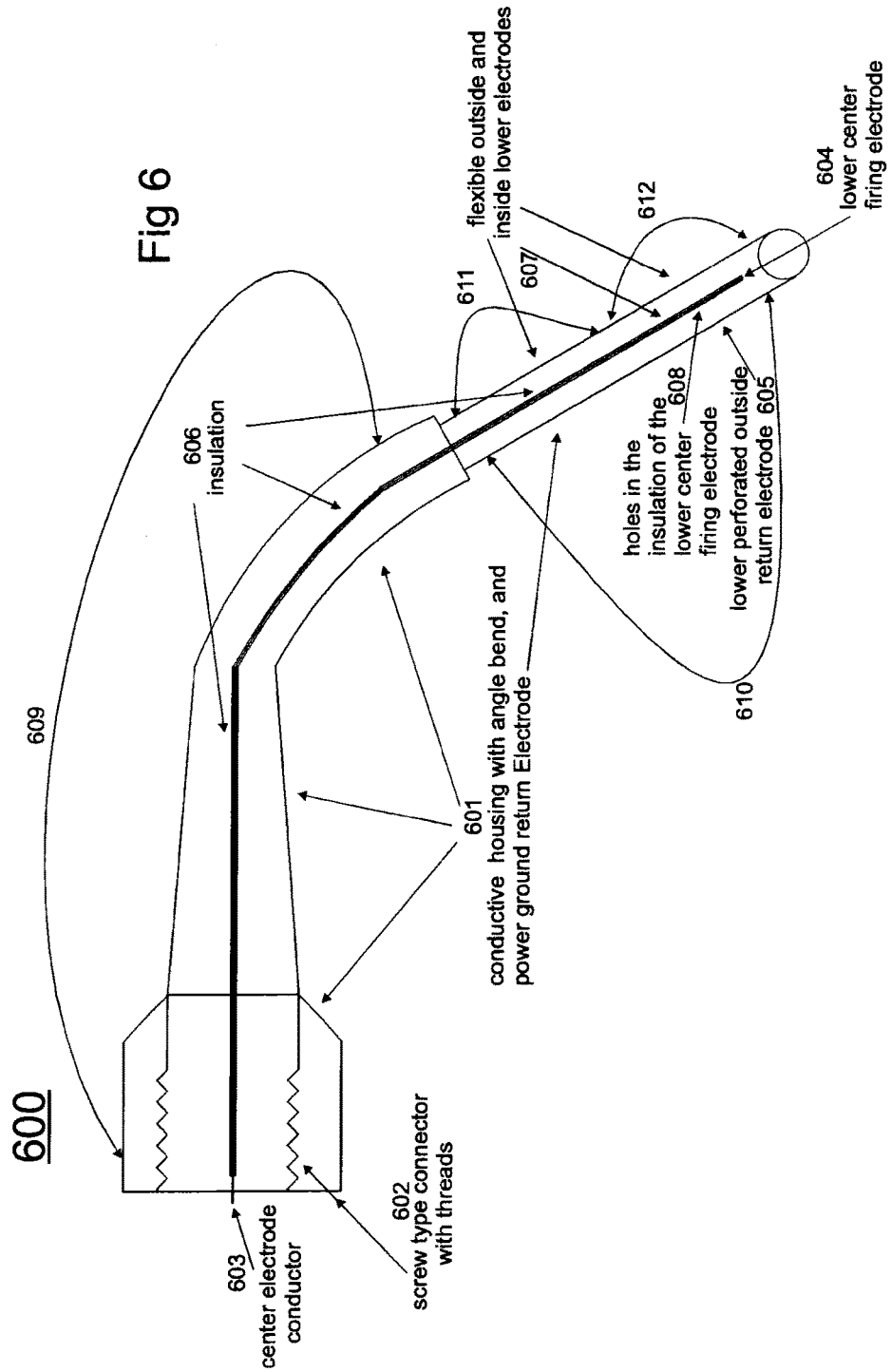

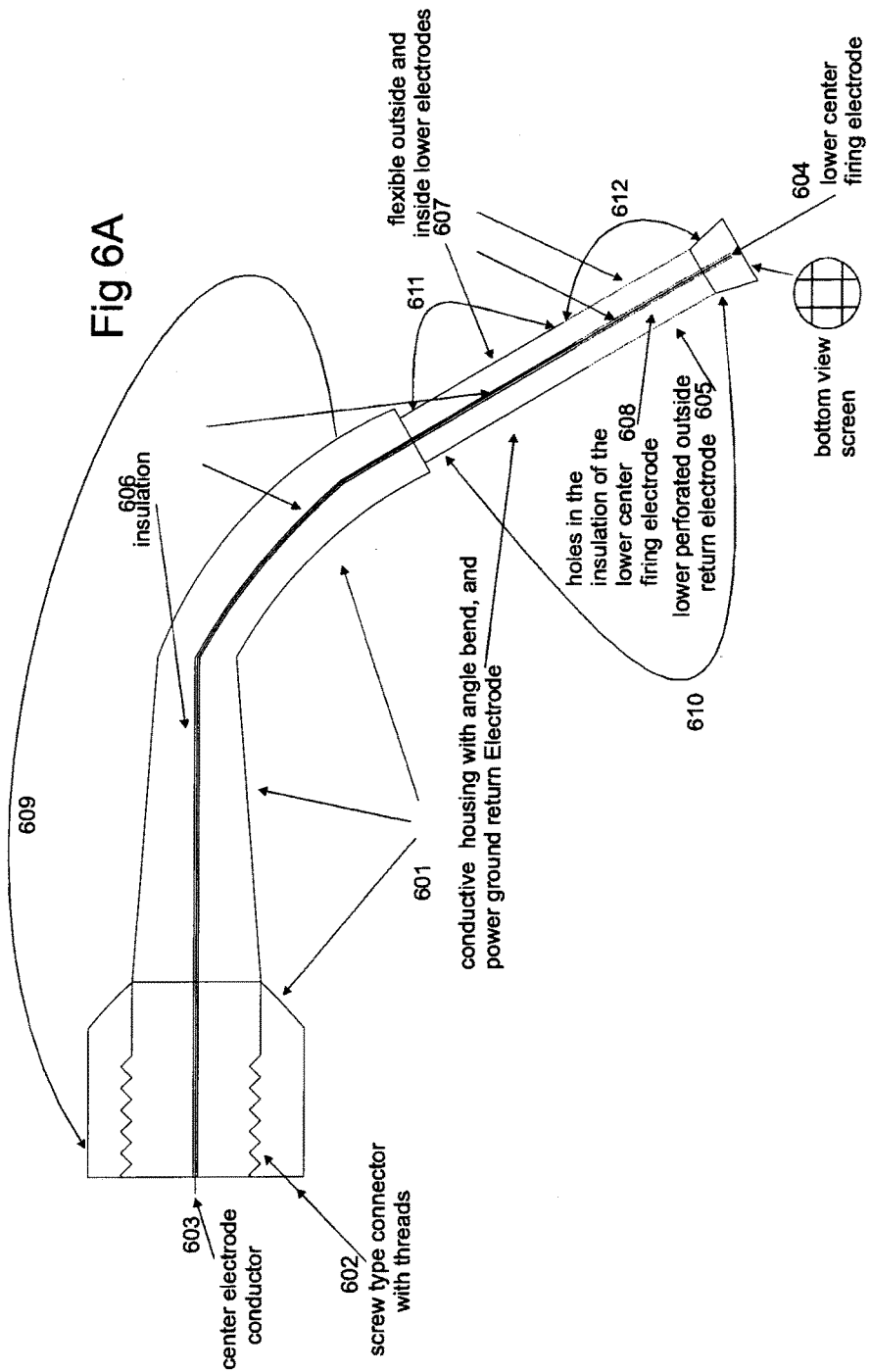

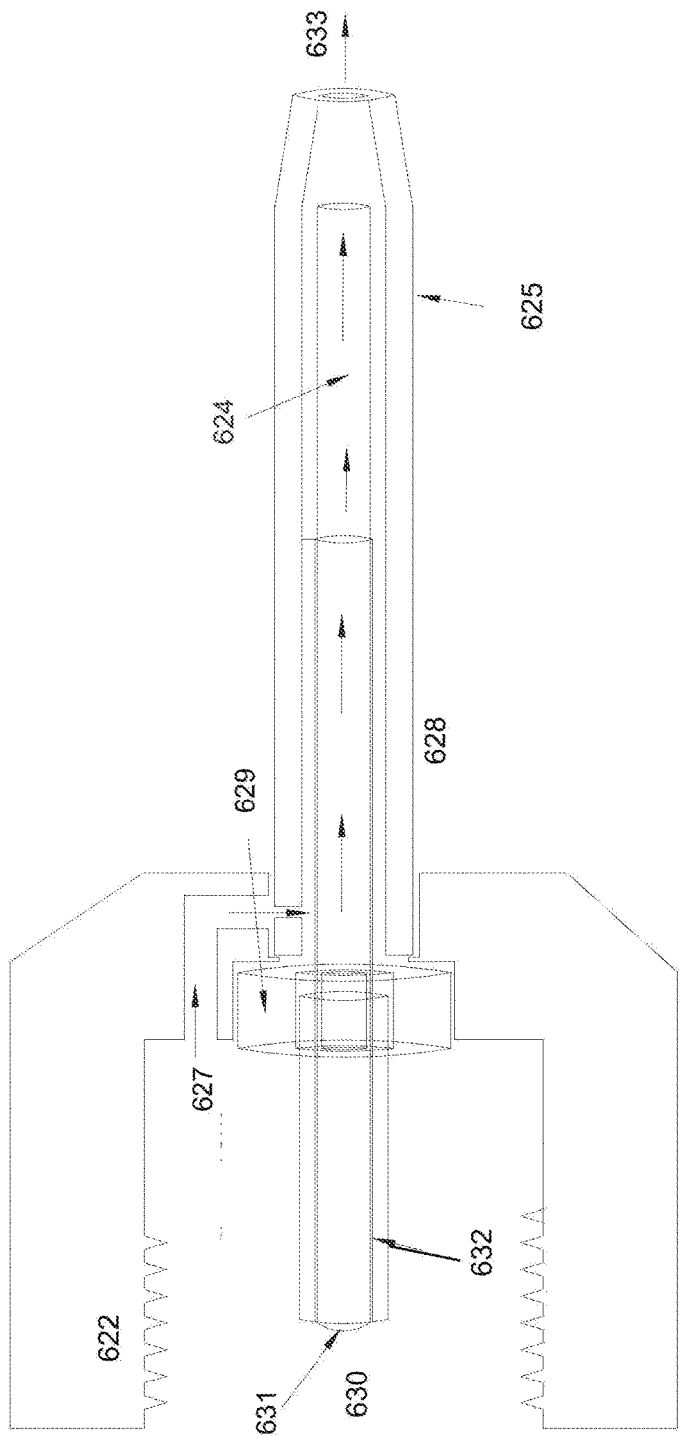

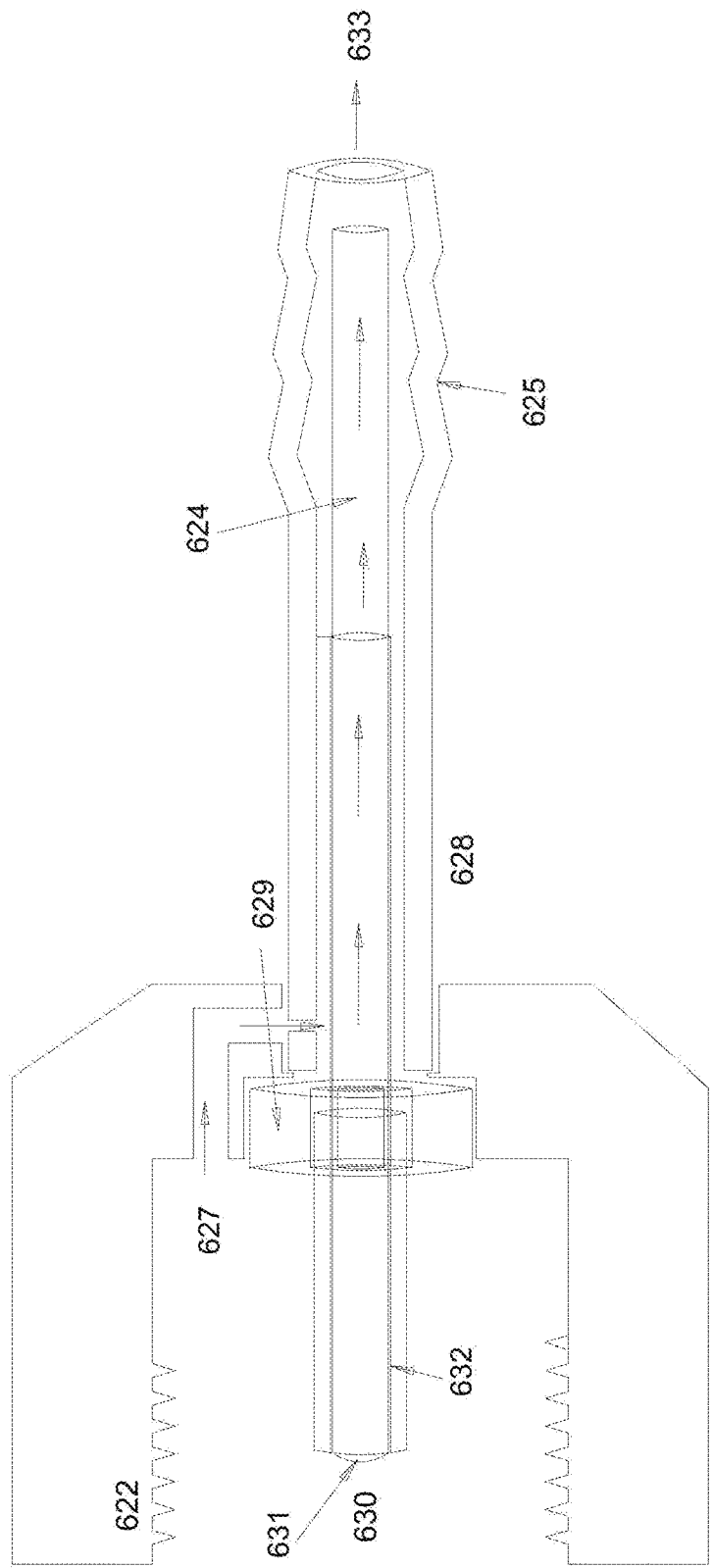

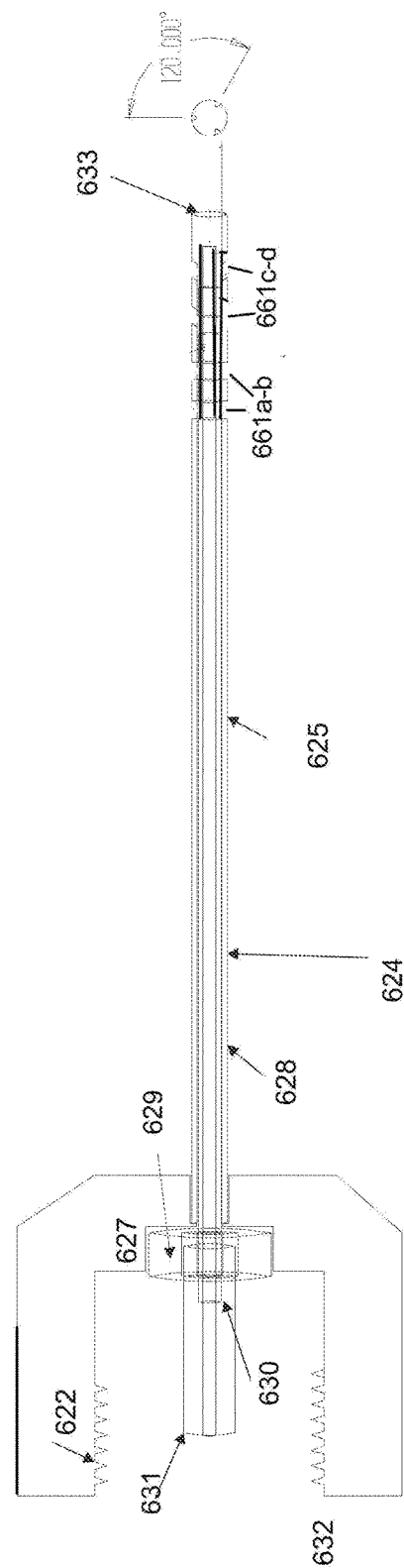

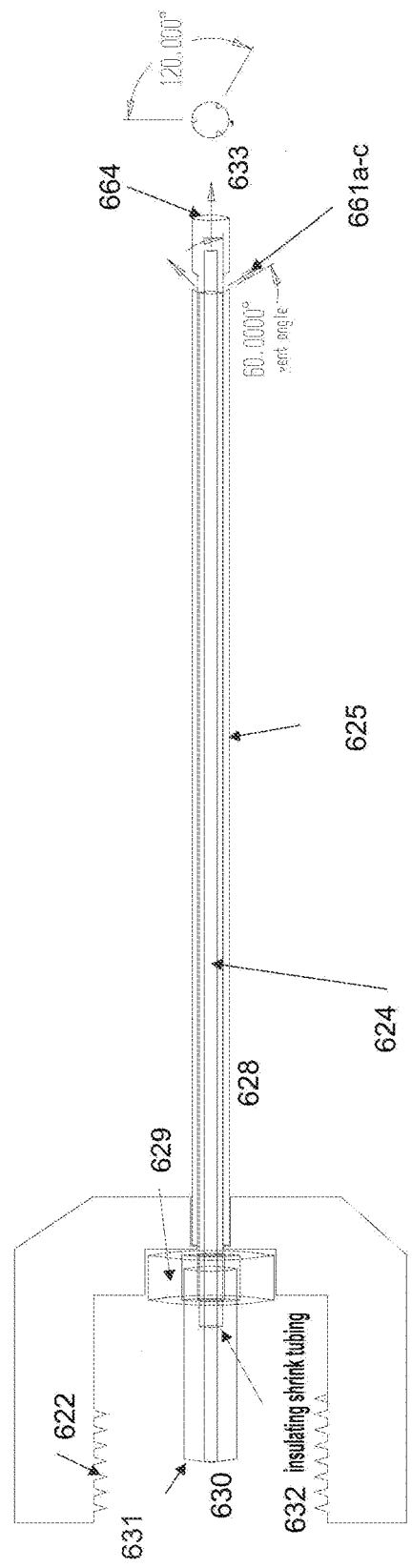

1300

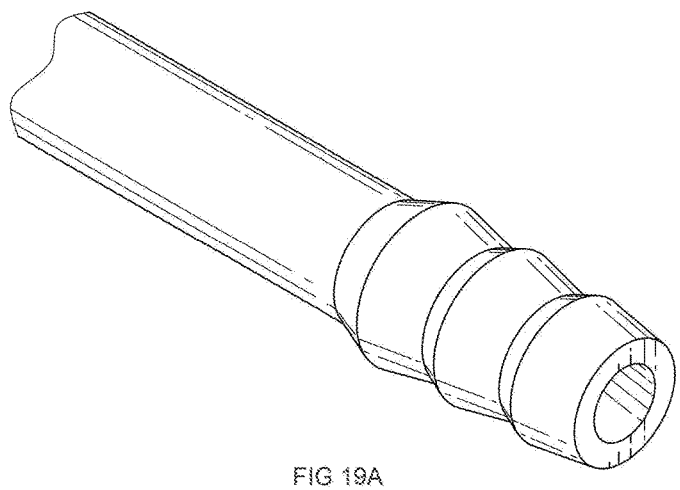
FIG 19A
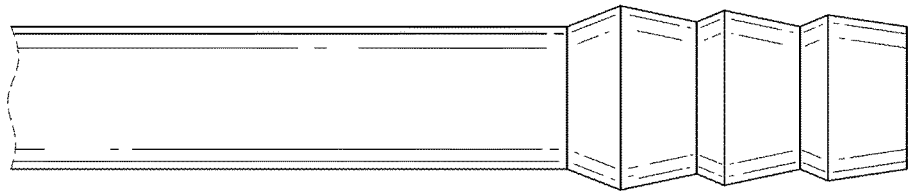
FIG 19B
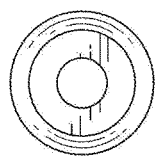 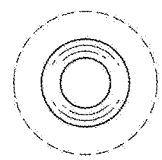
FIG 19C　　　　　　　FIG 19D

FIG 21D
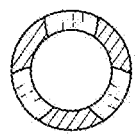
FIG 21E
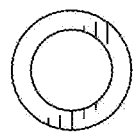 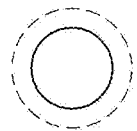
FIG 21F          FIG 21G

ELECTRICAL DISCHARGE IRRIGATOR APPARATUS AND METHOD

CROSS-REFERENCE TO RELATED APPLICATION

This application is a National Stage application based on International Application No. PCT/US2013/060943 filed on Sep. 20, 2013, published as WO 2014/099064 A1 on Jun. 26, 2015. This application also claims the benefit of continuation-in-part of PCT Application No. PCT/US12/70080, entitled "ELECTRICAL DISCHARGE IRRIGATOR APPARATUS AND METHOD," filed Dec. 17, 2012, which claims the benefit of U.S. Provisional Application No. 61/699,568, filed Sep. 11, 2012, which are incorporated herein by reference.

FIELD OF INVENTION

The present invention relates to an apparatus and method of utilizing acoustic waves created by an electrical discharge for irrigation and disinfection.

BACKGROUND OF INVENTION

Foreign bodies, such as bacteria and microbes pose a risk to dental health. These foreign bodies can invade canals and other hard to reach areas in dental structures and compromise dental health. It is the infections that are caused by the persistence of these foreign bodies that pose one of the greatest risks to the endodontic health of a patient.

Treatments to eliminate harmful canal contents, and therefore reduce the risk of infections, range from invasive treatments, such as extraction, to the far less invasive, yet not always effective, irrigation. Irrigation involves the use of an anti-bacterial solution to flush the canals. Today's irrigation solutions include utilizing direct lift, displacement and/or gravity pumps to move a fluid into canals, utilizing ultrasonic tips at varying rates, utilizing mechanical instruments, such as files, using positive pressure to inject fluid (for example, using a hypodermic needle) and negative pressure to remove it, and combinations of these techniques.

Studies have demonstrated that mechanical instruments alone cannot disinfect root canals. This is because large areas of canal walls, including apical, ribbon-shaped, and oval canals, cannot be cleaned mechanically because mechanical means cannot reach and come into physical contact with all surfaces within the tooth, so microorganisms in these areas can survive. Irrigation solutions are generally required to eradicate these microorganisms and various chemicals have been used for this purpose.

Ideally, an irrigant kills bacteria, dissolves necrotic tissue, lubricates the canal, removes the smear layer, and does not irritate healthy tissue. Presently, solutions that include sodium hypochlorite (NaOCl) and ethylenemide tetra-acetic acid (EDTA) are favored by dentists. The NaOCl solution, usually at a concentration between 1%-3% is used to dissolve tissue and disinfect (remove bacteria), while EDTA removes the smear layer. During an irrigation procedure, NaOCl is used initially to dissolve tissue and disinfect and EDTA is introduced at the end of the procedure to remove the smear layer. The EDTA application is followed by another flush of NaOCl or another inert solution.

Although certainly less invasive than extraction, irrigation has its shortcomings. First, NaOCl, EDTA, and other solutions found effective in irrigation are caustic solutions, including other bleaches, which when applied can badly irritate the mouth and surrounding structures. During an application, there is a risk that these solutions will perforate the apex of the canal, the end of the canal where the nerve meets the bone. If this happens, the results are so painful for a patient that the patient will end up on significant pain management, i.e., prescription pain killers, for at least two days, but sometimes, as long as two months. Second, current irrigation techniques carry a failure rate of up to 5% because often, the procedure fails to remove all the nerve tissue that is infected in the root canal system, so residual bacteria remains. Third, irrigation solutions are only effective at the time that they are applied. After a patient is treated with NaOCl and/or EDTA, the solutions are flushed out and there is no positive residual effect after the treatment is complete. Thus, any bacteria remaining in hard to reach canals will remain indefinitely and can lead to infection.

A need exists for a method and apparatus for effectively irrigating even hard to reach dental canals in a manner that produces residual benefits without causing damage and/or pain in the mouth and surrounding structures.

SUMMARY OF INVENTION

An aspect of an embodiment of the present invention includes electrical discharge irrigation device that includes a power source to produce a first voltage, a circuit coupled to the power source to convert the first voltage to a second voltage, a discharge capacitor to receive the second voltage from the circuit, at least one of a transistor and a controlled rectifier coupled to the discharge capacitor to receive the second voltage, and an output tip coupled to the at least one of a transistor and a controlled rectifier. The output tip includes a first end and a second end and a longitudinal axis extending between them, an electrode located in an interior space of the output tip configured to receive an electrical charge from the at least one of a transistor and a controlled rectifier and to release an electric discharge, and a ground return comprising an outside surface of the output tip. A space between the electrode and the ground return holds a conductive medium and the conductive medium is in contact with the electrode and the ground return to produce the electric discharge.

An aspect of an embodiment of the present invention includes an output tip for an electrical discharge irrigation device that includes a first end and a second end and a longitudinal axis extending between them, and an electrode located in an interior space of the output tip to receive an electrical charge from a power source, a ground return that includes an outside surface of the output tip, where between the electrode and the ground return is a conductive medium, and the electrode and the ground return are in contact with the conductive medium. The output tip also includes an insulating layer that includes at least one perforation, the insulating layer is coupled to one of the electrode and the electrode. The ground return are electrically coupled through the at least one perforation to produce an electric discharge. The tip also includes at least one vent extending through the outside surface of the output tip.

An aspect of an embodiment of the present invention includes a method of utilizing an electrical discharge irrigation device and includes obtaining an electrical discharge irrigation device which includes: a power source to produce a first voltage, a circuit coupled to the power source to convert the first voltage to a second voltage, a discharge capacitor to receive the second voltage from the circuit, at least one of a transistor and a controlled rectifier coupled to the discharge capacitor to receive the second voltage, and an output tip coupled to the at least one of a transistor and a controlled rectifier. The output tip includes a first end and a second end and a longitudinal axis extending between them, an electrode located in an interior space of the output tip configured to receive an electrical charge from the at least one of a transistor and a controlled rectifier and to release an electric discharge, and a ground return comprising an outside surface of the output tip. A space between the electrode and the ground return holds a first conductive medium and the first conductive medium is in contact with the electrode and the ground return to produce the electric discharge. The method also includes positioning the output tip of the device in a second conductive medium and engaging the trigger on the device to control the electric discharge.

An object of the present invention is to kill foreign agents, including toxins, bacteria, and microbes, dissolve and remove necrotic tissue, lubricate the canal, and remove the smear layer without causing damage and/or pain in the mouth and surrounding structures.

A further object of the present invention is to utilize a liquid in irrigation without the undesired side effects of bleach, or other chemical agents, while still achieving the desired anti-bacterial and other oral health benefits.

A further object of the present invention is to provide a method and apparatus for irrigation that when utilized, provides a patient with a residual antimicrobial effect after the irrigation procedure is complete.

A further object of the present invention is to provide cleaning, irrigation of the tooth canals for proper Root Canal Procedures per American Dental Association (ADA) guidelines.

A further object of the present invention is to irrigate the periodontal pocket in procedures related to both periodontal disease and peri-implantitis.

A further object of the present invention is to provide a UV light source within the root canal or periodontal pocket to provide bioremediation, light at the point of dental procedure and as a real-time feed back to the operator of actuation of innovation.

An embodiment of the present invention is a hand held irrigation device that generates an electrical discharge, creating cavitation and cavitation byproducts and/or plasma, acoustical shock waves and UV radiation that irrigate dental canals and other structures, including killing foreign agents, during an irrigation treatment, and also introduce one or more of the following: UV light, hydrated electrons, OH radicals, $H_2O_2$, $H_3O$, $O_2$, $MnO_2$, $O_3$ (ozone), O, $HO_2$, electrons, positive or negative ions, reactive chemical radicals, hydroxyl radicals, super oxides, nanoparticles, and/or any other known anti-pathogen, anti-chemical pollution, chemical reactions, which act to combat foreign agents, even after use of the device has ceased.

An embodiment of the present invention comprises a housing, a low voltage power source, a means to convert the low voltage to a high current voltage, including but not limited to a timing circuit, means to produce a high voltage spike, including but not limited to a MOSFET high side and low side to produce a direct injected pulse, a high voltage igniter switch, and/or an air gap switch, to allow the energy to discharge completely through one or more electrodes embedded in and/or external to the tip of the embodiment. An embodiment of the present invention employs capacitors to store the energy before discharge. In an embodiment of the present invention that does not utilize a spark gap, a transformer at a high impedance state delivers a high voltage spike and current to cause a plasma creation, cavitation and an acoustical shock wave.

The tip of an embodiment of the present method and apparatus utilizes electrodes comprised of biologically inert materials, including but not limited to, silver, copper, stainless steel, and/or iron, which have a toxicity to bacteria and act as anti-pathogens. Electrodes in further embodiments of the present invention may include ceramic-based electrode, carbon-based electrodes, and other conductive materials. The nanoparticles created by the electrodes and ground return combat the bacteria and foreign particles in the canals. Nanoparticles can also be created by the introduction of coatings to electrodes or other working surfaces, dispersions and other working surfaces. Working surface are those surfaces that come into contact with cavitation produced microjets thereby producing the aforementioned nanophase particles.

An embodiment of the present apparatus and method utilizes an electrical discharge from an electrode in an embodiment of the apparatus in order to irrigate dental structures, i.e., kill foreign agents, including toxins, bacteria, viruses, and microbes, dissolve necrotic tissue, lubricate the canal, and remove the smear layer without causing damage and/or pain in the mouth and surrounding structures while providing residual resistance to these foreign agents. The utilization of the spark discharge from the electrode in an embodiment of the present apparatus creates "shock waves" in the irrigation fluid, which have a high gradient at their front, so the difference in pressure created in the irrigation fluid damages bacterial membranes and often destroys or weakens them. One of skill in the art may also consider these shock waves to be compression waves because they produce both compression and rarefaction. Because these waves need not hit bacterial targets directly to be effective, the effects of the waves can penetrate canals and dental structures that are difficult to reach. The waves produced by embodiments of the apparatus include pressure waves, compression waves, acoustic waves and/or shock waves.

The discharge column created utilizing an embodiment of the present method and apparatus is a source of ultra-violet (UV) radiation, which when absorbed by water molecules in the irrigating fluid and/or other conductive medium produces UV light, hydrated electrons, OH radicals, $H_2O_2$, $H_3O$, $O_2$, $MnO_2$, $O_3$ (ozone), O, $HO_2$, electrons, positive or negative ions, reactive chemical radicals, hydroxyl radicals, super oxides, nanoparticles, and/or any other known anti-pathogen, anti-chemical pollution, chemical reactions, which destroy microbes and also some organic compounds. The electrical discharge of an embodiment of the invention by controlling cavitation and/or plasma creation and discharge additionally disseminates hydrated electrons, nanoparticles, and positive and/or negative ions (from metal electrodes utilized in various embodiments) which continue anti-microbial and anti-bacterial action against foreign agents after the irrigation procedure has terminated.

An embodiment of the present invention utilizes the aforementioned functionality of the device in tissue alteration and removal to complete medical procedures in the body related to anatomical structures that are not in the mouth. Embodiments of the present invention can be utilized for procedures including removing tissue and ablating tissue An advantage of embodiments of the present invention is controlling the production, and subsequent application, of cavitation processes and cavitation products. For example, by utilizing the diverse of powering schemes that are enabled by the device and method, as described, including, but not limited to, variations in the electronics, the apparatus and method can control the parameters controlling cavitation. By controlling the parameters of cavitation, embodiment of the apparatus and method offers different and controlled degrees of power delivery, irrigation, and/or production of active species, etc. The Cavitation in a liquid is the formation, growth and implosion of voids or bubbles as a consequence of rapid changes of pressure. Cavitation has a unique ability to focus large amounts of energy and to convert one type of energy to another. Commercial applications of cavitation are most commonly associated with industrial cleaning applications, where the cavitating bubbles are used to overcome the particle-to-substrate adhesion forces, loosening contaminants and moving them away from the cleaned surface, resulting in a liquid based cleaning technique. Cavitation is responsible for the creation of plasma, however, plasma is also produced directly by the electrical discharge.

An advantage of embodiments of the present invention is controlling the production, and subsequent application, of plasma. Plasma is created by the device through the electrical discharge as well as a product of the cavitation, in embodiments of the device where cavitation occurs. Thus, like with controlling cavitation, by utilizing the diverse of powering schemes that are enabled by the device and method, as described, including, but not limited to, variations in the electronics, the apparatus and method can control the parameters controlling plasma creation. By controlling the parameters of plasma production and discharge, embodiment of the apparatus and method offers different and controlled degrees of power delivery, irrigation, and/or production of active species, etc. Thus, depending upon the embodiment of the device and its utilization, a given embodiment may produce cavitation products and processes and/or plasma.

Cavitating bubbles are generated by fast overheating of a liquid by applying a short pulse of electric current that results in controlled regions of variant pressure within a working medium. The threshold energy of cavitation bubble formation can be estimated as the energy required for the heating of the infinitesimal thin water layer adjacent to the electrode (where adjacent is defined as close enough to experience the energy from the electrical pulse) to 100° C. This energy is determined by the radius of the electrode, the characteristics of the power applied and the medium being cavitated. Upon cavitation, each bubble emits a narrow pulse of photons (sonoluminesence), and produces an associated microjet.

Embodiments of the present invention are utilized to produce cavitation and control in liquids, which serve to treat and destroy unwanted matter.

In an embodiment of the present invention, results of utilizing an electrical discharge from an electrode in an embodiment of the apparatus to eradicate pollutants, such as bacteria, can include but are not limited to, mechanically destroying bacteria and microbial cells, chemically and permanently changing the cells so they cease regular biochemical activity, irreversibly changing the genetic system of the cells. Cellular damage sustained by the pollutants includes, but is not limited to, cracking the cell walls without releasing the contents of the cells, and dispersing the cell wall and contents of the cells, damage to the DNA structure of the cells.

An embodiment of the present method utilizes an irrigant, which can be either a non-abrasive or an abrasive irrigant, depending upon the goals of the method. Irrigants utilized in the method include, but not limited to, saline solution, water, glutaraldehyde, nanoparticle dispersions, hydrogen peroxide, and/or any antibiotic and/or anti-microbial solution.

An embodiment of the present invention is utilized in conjunction with the current NaOCl and EDTA protocol discussed in the Background section.

An embodiment of the present invention utilizes an ultrasonic tip that disrupts biofilm (bacteria colonies) by using ultrasonic energy to remove the biofilm, and disrupt the bacteria. In an embodiment of this invention, the ultrasonic pulse is provided in a target area at a rate of about 1-99 Hz to mechanically remove the biofilm, and disrupt the bacteria. Tips utilized in this application comprise an exterior and/or interior water line system that delivers water to cool the tips, provide a conductive medium facilitating a cavitation medium and to flush the periodontic pocket with water and to provide nanoparticulate species for subsequent antimicrobial reactions as previously described. The flushing action cleanses the area of the bacteria that the mechanical action of the tip has disrupted in the biofilm and calculus from the tooth structure and bioremediates that area.

Embodiments of the present invention are utilized in ultrasonic treatments in Piezoelectric/Magnetostrictive scalars, and/or water piks. In these embodiments, a reservoir external to the hand piece and/or in the hand piece includes electrodes that generate the electrical discharge into, for example, a conductive medium, including but not limited to, a dielectric fluid. In an embodiment of the present invention, electrodes are embedded in the tip of the device. A conductive medium such as water and/or fluid is treated by the electrodes and is dispensed into the mouth of a patient after it undergoes an electrical discharge event, an event includes, but is not limited to, cavitation, shock wave production, production of energized particles/ions. Depending upon the treatment being applied, different discharge regimens are desirable, including both corona and arc discharge events.

Embodiments of the present invention are utilized in the irrigation of the periodontal pocket in connection with treatments for periodontal disease as well as peri-implantitis.

BRIEF DESCRIPTION OF DRAWINGS

FIG. 1 depicts an aspect of embodiment of the present invention.

FIG. 1A depicts an aspect of an embodiment of the present invention.

FIG. 3 depicts a workflow of an embodiment of the present invention.

FIG. 3A depicts a workflow of an embodiment of the present invention.

FIGS. 6-6F depict aspects of an embodiment of the present invention.

FIGS. 19A-19E depict aspects of an embodiment of the present invention.

FIGS. 21A-21H depict aspects of an embodiment of the present invention.

DETAILED DESCRIPTION OF THE INVENTION

Figure 2:
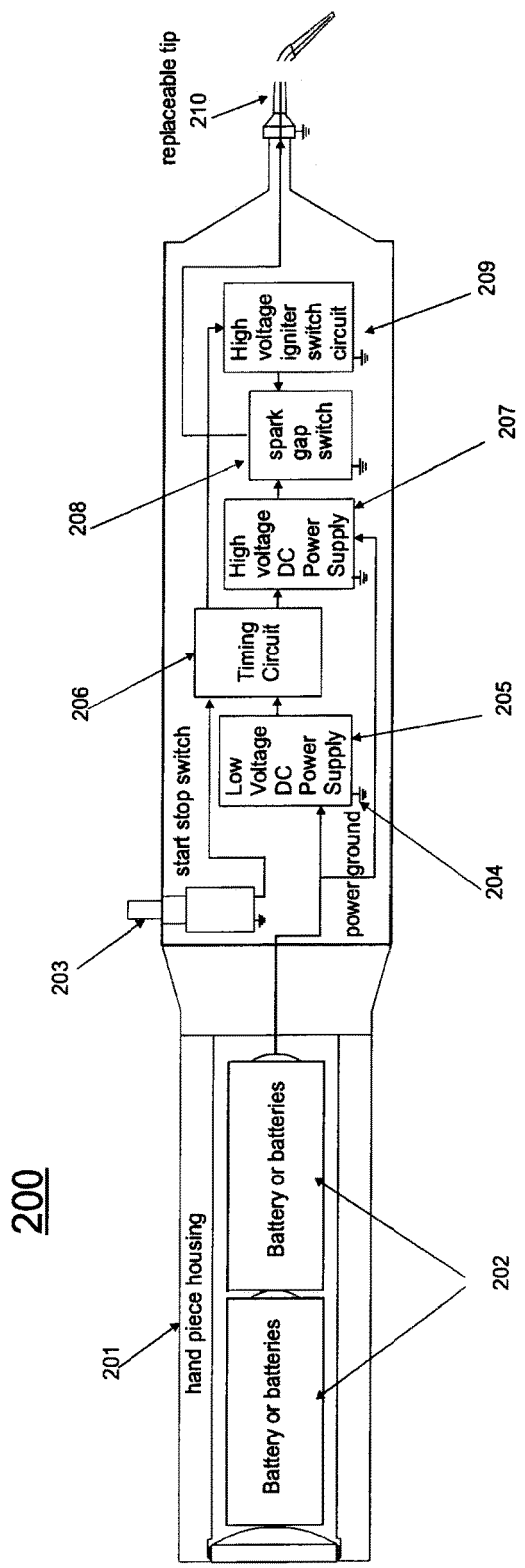
FIG. 2 depicts an aspect of an embodiment of the present invention.

The apparatus and method of the present invention utilize an electric discharge and creates oscillating pressure to eradicate unwanted matter from a medium. Embodiments of the present invention are used as irrigation systems in endodontic procedures as well as in periodontal procedures, including treatments for periodontal disease and peri-implantitis. These dental irrigation systems include, but are not limited to, an irrigation system for Piezoelectric/Magnetostrictive scalars, irrigation system for cleaning the teeth pockets (e.g., root canals or periodontal or endodontic regions), and removing biofilm, a water pick irrigation system for cleaning the teeth, an irrigation system for flushing the periodontal pocket, and/or an irrigation system for surgery for disinfecting wounds. While some embodiments of the present invention pulse liquid that is external to the device directly, for example, in dental canals in endodontic uses, some embodiments of the present invention contain one or more internal reservoir(s) where the liquid and/or water used is pre-treated (pre-pulsed) before it is released into the treatment area, for example, in Piezoelectric/Magnetostrictive scalars and/or water picks.

An embodiment of the present invention utilized for endodontic procedures comprises a tube with electrodes to deliver an electrical discharge which creates the desired acoustical waves, cavitation related byproducts, and/or plasma, in many of these procedures, the embodiment utilized emit electrical pulses through a tip of an embodiment of the apparatus as spark discharges.

Throughout this application, the terms "tip" and "output tip" are used interchangeably to describe and aspect of embodiments of the present invention.

The electrical pulses agitate the liquid into which the tip is immersed and create acoustic waves, shock waves, cavitation, plasma, sonoluminsence, microjets and additional discharges that kill foreign agents, including toxins, bacteria, and microbes, dissolve necrotic tissue, lubricate the canal, and remove the smear layer while providing anti-bacterial and anti-microbial benefits both during and after treatment. Thus, an embodiment of the present invention can be utilized to irradiate bacteria and other infectious agents while providing cleaning and irrigation of the tooth canals for proper Root Canal Procedures in accordance with ADA guidelines.

An embodiment of the apparatus is used as a Piezoelectric/Magnetostrictive scalar. As discussed later in greater detail, an embodiment of the present invention utilized for as a Piezoelectric/Magnetostrictive scalar utilizes an ultrasonic tip that disrupts biofilm (bacteria colonies) by using ultrasonic energy to remove the biofilm, and disrupt the bacteria. In an embodiment of this invention, the ultrasonic pulse is provided in a target area at a rate of about 1-99 Hz—with a pulse duration of 100-500 microseconds at power settings ranging from milli-joules to micro-joules to mechanically remove the biofilm, and disrupt the bacteria. Tips utilized in this application comprise an exterior and/or interior water line system that delivers water to cool the tips, provide a medium for the electrical discharge and to flush the periodontic pocket with water. The flushing action cleanses the area of the bacteria that the mechanical action of the tip has disrupted in and/or fractured off the tooth structure.

In an aspect of a Piezoelectric/Magnetostrictive embodiment, the water and/or fluid that is pulsed is essentially pre-treated in one or more "holding chambers" internal to the apparatus before it passes into the water lines feeding the tips. Then, as the tip is, used it is this treated water that flushes the pockets and provides better pathogen kill, and long term protection in contrast to current methods of just using water, or a mild chemical agent and water. The current industry-standard treatment, as opposed to embodiment of the present method, has an anti microbial effect, but only while it is actually flushing the pocket. This effect does not continue. In an aspect of a Piezoelectric/Magnetostrictive embodiment, this anti microbial effect will continue after flushing the pocket. Liquids utilized in this application include, but are not limited to, a 2% glutaraldehyde solution. In embodiments of the present invention, liquids used in this application may or may not be generally known anti-microbial solutions like gluteraldehyde, hydrogen peroxide, etc. Pre-treating the water/liquid in internal reservoirs is also utilized in embodiments used to clean periodontic wound sites. This type of application is discussed in greater details in FIG. 10.

Returning to endodontic uses, an embodiment of the present invention is a hand held irrigation device that generates an electrical discharge, creating acoustical shock waves in an irrigant and UV radiation that irrigate dental canals and other structures during an irrigation treatment, and also introduce one or more of the following: UV light, hydrated electrons, OH radicals, $H_2O_2$, $H_3O$, $O_2$, $MnO_2$, $O_3$ (ozone), O, $HO_2$, electrons, positive or negative ions, reactive chemical radicals, hydroxyl radicals, super oxides, nanoparticles, and/or any other known anti-pathogen, anti-chemical pollution, chemical reactions, which act to combat foreign agents after use of the device has ceased. Further embodiments of the present invention are mounted or table top models, as opposed to hand held.

An embodiment of the hand-held version of the present apparatus, which is utilized, for example, for endodontic treatments, is comprised of a handle, which is used to grip and manipulate the apparatus, a body, where various electrical components are housed, and a tip, which contains one or more electrodes and a ground return, which is inserted into a conductive liquid in the mouth of a patient in order to irrigate a selected area using acoustic waves generated by one or more circuits in the apparatus. An embodiment of the tip of the apparatus is comprised of flexible material such that it can be positioned deep within dental canals. Although the utilizing an embodiment of the tip comprised on a flexible material assists in positioning the tip, one of skill in the art will recognize that the described results are also achievable with a tip comprised of an inflexible, i.e., rigid, material as well.

An embodiment of the apparatus contains a low voltage power source and the internal circuitry of the apparatus, discussed later in greater detail, converts the initial low voltage power, to high voltage power, which pulses the liquid into which the tip is immersed. The tip of an embodiment of the present method and apparatus utilizes electrodes comprised of biologically inert materials, including but not limited to, silver, copper, stainless steel, and/or iron (ferrite) which have a toxicity to bacteria and act as an anti-pathogen. Electrodes in further embodiments of the present invention may include ceramic-based electrode, carbon-based electrodes, and other conductive materials. The nanoparticles created by the electrodes, and/or working surface, combat the bacteria and other foreign particles in the canals.

In an embodiment of the present invention, because the electrical discharge itself destroys foreign agents both during and after an irrigation treatment, the irrigant utilized needn't possess antiseptic or anti-bacterial qualities on its own. For example, although NaOCl and EDTA can be used in conjunction with this method, saline and water solutions are also effectively used with this method. In general, any anti-bacterial and/or anti-microbial fluids utilized in irrigation protocols are compatible with this apparatus and method as dielectric liquids transmit the electrical discharge and they may improve its effectiveness in use. Thus, because water is conductive, it works well with the present method and apparatus.

In the embodiments of FIGS. 1-2 and 4-5B, the power source of the apparatus is located in the handle of the apparatus and the circuitry is in the body, however, one of skill in the art will recognize that this arrangement can be altered as desired to manipulate or improve the ergonomics of the apparatus. Further embodiments of the present invention may utilize a streaming power source.

The utilization of the electrical discharge from one or more electrodes in the tip of an embodiment of the present apparatus create(s) "shock waves" in the irrigation fluid which have a high gradient at their front, so the difference in pressure created in the irrigation fluid damages bacterial membranes and/or destroys them. The waves are effective in a given radius and therefore penetrate canals and dental structures that are difficult to reach and thus effectively irrigating them.

The electrical discharges produce the pulsed shock waves, which damage pollutants on a cellular level. The pulses may mechanically destroy bacteria and microbial cells, chemically and permanently change the cells so they cease regular biochemical activity, and/or irreversibly change the genetic system of the cells. Cellular damage sustained by the pollutants includes, but is not limited to, cracking the cell walls without releasing the contents of the cells, and dispersing the cell wall and contents of the cells, DNA disruption.

The embodiment of the tip additionally discharges UV radiation, which when absorbed in different degrees by water molecules, hydrogen peroxide, the other mediums discussed, and/or in the irrigating fluid, produces ozone, $H_2O_2$ and OH radicals, which destroy microbes and also some organic compounds. The electrical discharge of an embodiment of the invention additionally disseminates hydrated electrons, nanoparticles, and positive and/or negative ions (from metal electrodes utilized in various embodiments) which continue anti-microbial and anti-bacterial action against foreign agents after the irrigation procedure has terminated. Embodiments of tips may discharge one or more of the following: UV light, hydrated electrons, OH radicals, $H_2O_2$, $H_3O$, $O_2$, $MnO_2$, $O_3$ (ozone), O, $HO_2$, electrons, positive or negative ions, reactive chemical radicals, hydroxyl radicals, super oxides, nanoparticles, and/or any other known anti-pathogen, anti-chemical pollution, chemical reactions.

One advantage of embodiments of the present invention is that they are effective against pollutants yet are able to utilize relatively low power settings over relatively short periods of time and achieve high levels of efficiency. Embodiments of the present invention that use particularly low power settings enable the miniaturization and the simplification of the driving circuit and power requirements. For example, an embodiment of the present invention eradicates foreign agents from a selected medium in 25 seconds-5 minutes at between 20 Hz, the energy in 26 microjoules-4 joules. Some embodiments of the present invention utilize power requirements at least three magnitudes lower than the previous example, i.e., microjoules in place of joules. These settings are exemplary as dependent upon the use of the apparatus and the embodiment of the apparatus, the power settings and the duration of a treatment will vary.

FIGS. 1 and 1A depict embodiments of the present apparatus 100, 1800. In both embodiments, for clarity, the elements of this embodiment are depicted as black boxes. One of skill in the art will recognize the components from their descriptions. Also, later figures, such as FIG. 2, provide more detail regarding the visual appearance of the individual components.

In the embodiments of FIG. 1 and FIG. 1A, the power source, the batteries 101, 1801, are contained in a hand piece housing (not pictured). In FIG. 1, the center electrode 115, the ground return electrode 116, and the lower electrode assembly 117, are located in or on the tip, which makes contact with liquid into which a portion of the tip is submerged to create the acoustic waves therein. In FIG. 1A, the high voltage discharge center electrode 1815, the high voltage discharge ground electrode 1816, and the lower ground return electrode assembly 1817, are located in or on the tip, which makes contact with liquid into which a portion of the tip is submerged to create the acoustic waves therein. As explained later in reference to FIGS. 6-6F, the tips contains positive electrodes, and negative electrodes, and/or ground returns. The spacing of the electrodes in the embodiments of the tip may contribute to the functionality of the tip. For example, the different embodiments create a balance between the electrical discharge characteristics (power, time and shape of power curve), the conductive medium, including the fluid seeing the electrical discharge, and the surface area of the electrode/ground assemblies.

Referring first to FIG. 1, a housing (not pictured) encompasses the electronic circuits and other fragile and electrocharged items. In some embodiments of the present invention, the housing is made of a material that does not conduct electricity as the apparatus is held in the bare or minimally protected hand of the operator. Materials used to form the housing include, but are not limited to, plastic, wood, fiberglass, metal, and/or a composite material. The utilization of a plastic housing in an embodiment of the present invention represents a savings in manufacturing costs. In further embodiments of the present invention, the housing is conductive and serves as a ground return. The housing includes an opening for easy replacement of the batteries 101 in a battery compartment (not pictured) inside the housing 101. The housing is also molded in a manner that allows for easy cleaning and easy replacement of the battery or batteries 101 and is ergonomically designed to be held and manipulated by an operator.

One of skill in the art will recognize that a battery or batteries 101 is only one of many power source options for this device. For example, further embodiments of the present invention utilize solar cells as power sources. In FIG. 1, the battery or batteries 101 serve as a low voltage power source that is later converted to a higher voltage by later components of this embodiment. Batteries 101 utilized in embodiments of the apparatus include but are not limited to lithium batteries, such as lithium ion batteries. In some embodiments of the present invention, lithium batteries are utilized because they have a high current and rapid charging times. Additionally, lithium ion batteries have high energy storage density for their size, which is advantageous in embodiments of the present invention because the smaller the apparatus, the easier it is for an operator to use. Additionally, lithium Ion batteries have a high energy density for their sizes, have no memory problems, can be charged quickly, and have an efficient discharge of current. One of skill in the art will recognize that lithium and lithium ion batteries although compatible with some embodiments of the present invention are only one example of a power source utilized by embodiments of the present apparatus.

Utilization of a lower voltage power source and later converting the lower voltage power source to a higher voltage power source provides the benefit of utilizing readily available power sources, such as batteries. The embodiments described contain components to convert a low voltage power source to the higher voltage utilized by the device. However, one of skill in the art will recognize that further embodiments of the present invention, depending upon the power source utilized, can be configured to keep a consistent voltage and/or lower the voltage provided by the power source, in order to achieve and/or maintain a voltage useable in creating the desired, which include but are not limited to, cavitation processes, cavitation products, UV light, hydrated electrons, OH radicals, $H_2O_2$, $H_3O$, $O_2$, $MnO_2$, $O_3$ (ozone), O, $HO_2$, electrons, positive or negative ions, reactive chemical radicals, hydroxyl radicals, super oxides, nanoparticles, and/or any other known anti-pathogen, anti-chemical pollution, chemical reactions.

A non-battery low voltage power source is used in conjunction with a further embodiment. For example, another embodiment of the present invention in a table top model that utilizes an electrical wire to connect the hand piece to the power source, and box. This embodiment utilizes a standard power cord to provide the power, including but not limited to, a 110V to 220 ac 50/60 Hz. Various embodiments of the present invention are configured to utilize AC, DC, and/or other currents and electrical power used worldwide.

The battery compartment and the housing allow for the easy replacement of the battery or batteries 101. Thus, maintenance of the power source is simplified. The battery and/or batteries 101 housed in the battery compartment to power the apparatus include, but are not limited to, 0.8 vdc-30 vdc, and/or 3-7 volt batteries.

Coupled to the housing with the internal battery compartment is a DC low voltage regulator 102 that regulates the function of at the electronic components and integrated circuits in the embodiment of the apparatus. Coupled to the low voltage regulator 102 is a DC voltage switching integrated circuit (IC) driver 103 that drives power metal-oxide-semiconductor field-effect transistor (MOSFET) 110 and high voltage switching transformer 104 to convert the 0.8 vdc-30 vdc battery input, and/or the 3-7 volt battery input to a bus voltage including but not limited to, 180 vdc-300 vdc. High voltage switching transformer 104 includes, but is not limited to, a high frequency ferrite core transformer.

In this embodiment, a ferrite core transformer is utilized because it has a high frequency, is small, is very efficient, and it can handle a high current. The small size is ergonomically advantageous in hand-held embodiments of the device. The high current tolerance allows a ferrite core transformer to rapidly charge a high voltage discharge storage capacitor filter 107, such as a photo flash storage capacitor. The acoustic pulses generated in the apparatus are fast and repetitive, so the rapid charging is desirable in its operation. Further embodiments of the present invention utilize various transformers with one or more of the advantages enumerated regarding the ferrite core transformer. Further embodiments of the present invention utilize various capacitors with similar electrical properties.

In this embodiment, the converted 300 vdc voltage drives the acoustical shock wave in the liquid solution that creates the desired acoustic effect used for irrigation, which includes irrigation in endodontic procedures. Further embodiments of the present invention convert lower voltage from a power source, such as a battery, to higher voltage power ranging, for example, from 250 vdc to 500 vdc. Further embodiments of the present invention convert the voltage to 180 vdc to 250 vdc. The measure of the voltage differs in accordance with the application of the associated embodiment.

A bridge rectifier 105 is coupled to the high voltage switching transformer 104 and converts the AC output of high voltage switching transformer 104. Then, a high voltage filter inductor 106 filters out the AC ripple current for proper operation of the high voltage discharge storage capacitor filter.

In an embodiment of the present invention, a photo flash storage capacitor is used as the high voltage discharge storage capacitor filter 107 because a photo flash storage capacitor has low impedance and is capable of withstanding multiple and repetitive discharges without overheating or breaking down, i.e., incurring damage to its electrical properties. Further embodiments utilize varied high voltage energy storage capacitors and/or capacitor banks with low impedance. One of skill in the art will recognize additional capacitors beyond photo flash storage capacitors that possess these enumerated properties. Embodiments of the present invention may utilize one or more capacitors with these properties. When multiple capacitors are utilized, they may be of the same or of different types. Embodiments of the present invention that utilize a single capacitor provide benefits, including but not limited to, ease of miniaturization, reduction of noise, and a simplified design.

The high voltage discharge storage capacitor filter 107 is coupled to a high discharge load inductor 108 so that the high discharge load inductor 108 saturates under high discharge current from a low impedance to a high impedance, thus isolating the switching power portion of the circuit.

After this isolation is achieved, a high voltage discharge igniter capacitor 9 discharges all the energy into a high voltage discharge igniter transformer 114, causing a pulse, which can include, in some embodiments, a high voltage pulse, or in others, a lower voltage pulse, such as 250V or less, which is utilized to agitate liquid and create the acoustical waves utilized for irrigation and disinfecting. In this embodiment, a MOSFET 110 discharges voltage discharge igniter capacitor 109 into the high voltage discharge igniter transformer 114. Further embodiments of the present apparatus utilize additional transistors, including but not limited to, a silicon-controlled rectifier (SCR) transistor.

The activity of the MOSFET 110 is controlled by a micro controller device 118. In addition to the activity of the MOSFET 110, the micro controller 118 controls functions within this embodiment of the apparatus, including but not limited to, the period time and the cycle time (Hz) and the current of the power portion of the circuit. The pulse time is a function of the stored energy, which in this embodiment is denoted in micro seconds. By utilizing the micro controller device 118 to set the current, battery power can be conserved within this embodiment.

Once the energy is discharged by the high voltage discharge igniter capacitor 9, the high voltage discharge igniter transformer 114 creates a high voltage pulse. The high voltage pulse breaks down the air spark gap and liquid solution so that the high voltage discharge igniter capacitor 9 can discharge all its energy. The high voltage discharge igniter transformer 14 is isolated using a high voltage blocking capacitor 113. As aforementioned, the high voltage discharge igniter transformer 114 is a low impedance device and would be damaged by the high current that is discharged and stored in the high voltage discharge storage filter 7. Although the embodiment of FIG. 1 includes a spark gap as an electrical gap, further embodiments of the present invention do not utilize this component.

In this embodiment, a spark gap 112 serves as a high voltage switch. The spark gap 112 isolates the high voltage power supply and the energy stored in the high voltage discharge storage filter 107. Because the liquid solution into which the tip of the apparatus is immersed is dielectric, without the spark gap 112, the charge conducted in the liquid would load the power portion of the circuit. In this embodiment, the spark gap 112 allows the high voltage power portion to completely charge to obtain a high current discharge. The high voltage pulses created by the high voltage discharge igniter transformer 114 break down the air spark gap and liquid solution, allowing the high voltage discharge igniter capacitor 109 to discharge all it energy, making this spark gap 112 into a high voltage switch.

Figure 6F:
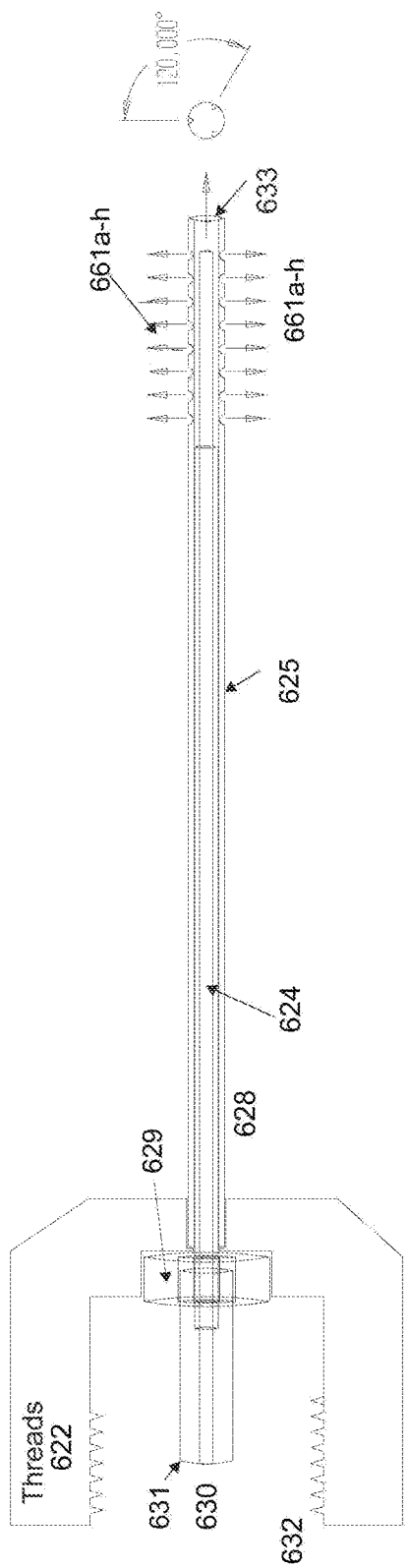

The tip of the apparatus, which is optionally replaceable, is discussed in greater detail in reference to FIGS. 6-6F. However, components of this tip are depicted in FIG. 1.

Referring to FIG. 1, the tip includes center electrode 115, which in an embodiment of the present invention is a high voltage discharge positive electrode, a ground return electrode 116, which in an embodiment of the present invention is a high voltage discharge negative electrode, and a lower electrode assembly 117, which comprises the firing chamber (not pictured). The center electrode 115, so-called due to its location in some embodiments of the tip, is embedded in the tip and the ground return electrode 116 is located on the outside of the tip, including but not limited to, on an outside jacket of the tip. At the lower portion of the tip, holes in both a conductive housing (not pictured) that surrounds electrodes in the tip and in the insulation (not pictured) within the tip, allow liquid solutions to enter into the firing chamber (not pictured). The chamber includes the lower electrode assembly 117. This is where the discharge takes place. The lower electrode assembly 117 in the tip is placed in liquid in order to agitate the liquid and create the acoustic waves utilized in the irrigation of targeted areas.

In one embodiment of the present invention, the center electrode 115 is a negative electrode and the ground return electrode 116 is a positive electrode. The charges of the electrodes vary provided that there is a center electrode and a return electrode with different charges to create pulses. The apparatus creates the electrical discharge utilizing a center electrode 115, and a ground return electrode 116, which will be discussed in more detail in reference to FIG. 6.

Coupled to the aforementioned micro controller device 118 is a liquid crystal display (LCD) 119 to aid the user in accurately utilizing the apparatus. As this embodiment is programmable, the LCD 119 displays the selected settings to the user.

Further embodiments of the present invention utilize varying displays and some do not utilize a display, as the display, although user-friendly, can affect the cost of the apparatus. A start/stop switch 120 coupled to the micro controller 118 initiates and deactivates the apparatus. A second switch, a period cycle pulse time select switch 121, allows the user to select the period time and cycle time. In another embodiment of the present invention, the LCD display 119, or an alternative display, is integrated with a touchscreen with start/stop and/or selection controls which include the same functionality as the start/stop switch 120 and the period cycle pulse time select switch 121. Also coupled to the micro controller device 118 is a programmable current control trimpot 122, which is used to interface with the micro controller device 118 and the DC voltage switching IC driver 104.

As discussed in reference to FIG. 1, further embodiments of the present invention do not utilize a spark gap. FIG. 1A is an example of an embodiment that does not utilize this component.

Referring to FIG. 1A, a housing (not pictured) encompasses the electronic circuits and other fragile and electro-charged items. In some embodiments of the present invention, the housing is made of a material that does not conduct electricity as the apparatus is held in the bare or minimally protected hand of the operator. As with the embodiment of FIG. 1, materials used to form the housing include, but are not limited to, plastic, wood, fiberglass, metal, and/or a composite material and the housing includes an opening for easy replacement of the batteries 1801 in a battery compartment (not pictured) inside the housing 1801. One of skill in the art will recognize that a battery or batteries 1801 is only one of many power source options for this device. Batteries 1801 utilized in embodiments of the apparatus include but are not limited to lithium batteries, such as lithium ion batteries. In some embodiments of the present invention, lithium batteries are utilized because they have a high current and rapid charging times. The battery and/or batteries 101 housed in the battery compartment to power the apparatus include, but are not limited to, batteries with a voltage range of 0.8 vdc-30 vdc.

Referring the FIG. 1A, the voltage from the battery 1801 flows to the low voltage regulator 1802, which regulates the voltage to all the integrated circuits and the microprocessor. The switching IC driver 1803 receives the unregulated voltage from the battery 1801, and the switching IC driver 1803, in conjunction with the high voltage switching transformer 1804, send the AC voltage to the DC Bridge rectifier 1805, which converts the AC high voltage to a DC. This DC high voltage flow through inductor 1806, which filters out any ripple current. After passing through inductor 1806, the voltage flows to the high voltage filter capacitor 1807, which is also a high voltage storage bank, for quick loading of the high voltage discharge capacitors.

The high voltage filter capacitor 1807 now flows to the high voltage discharge load inductor 1808, which in an embodiment of the present invention, is a saturating type inductor. The voltage then flows from the high voltage discharge load inductor 1808 to high voltage discharge capacitor 1809, which is connected to the high side low side metal-oxide-semiconductor field-effect transistor(s) (MOSFET) 1810*b* (a MOSFET is commonly referred to as a MOSFET transistor despite this designation being redundant).

A microcontroller 1818 device controls functions, including, but not limited to, start stop, treatment time, cycle time, Hz frequency and pulse time. The microcontroller 1818 also controls the liquid crystal display (LCD) 1819 and the programmable trim pot 1822. In this embodiment, the LCD display 1819 aids the user in accurately utilizing the apparatus. As this embodiment is programmable, the LCD 1819 displays the selected settings to the user. Further embodiments of the present invention that incorporate one or more aspects of FIG. 1A utilize varying displays and some do not utilize a display, as the display, although user-friendly, can affect the cost of the apparatus. In this embodiment, the programmable trim pot 1822 controls the buss voltage.

Returning to FIG. 1A, in this embodiment, the micro controller 1818 sends a signal to the high side and low side MOSFET driver 1810*a*, which is connected to the high side and low side MOSFET transistor(s) 1810*b*. In turn, the high side MOSFET transistor(s) 1810*b* is connected to a high voltage discharge capacitor(s) 1809.

As aforementioned, the high voltage discharge center electrode 1815, the high voltage discharge ground electrode 1816, and the lower ground return electrode assembly 1817 comprise the tip of this embodiment. For ease of understanding, the high voltage discharge center electrode 1815, the high voltage discharge ground electrode 1816, and the lower ground return electrode assembly 1817 will be collectively referred to as the tip assembly.

Returning to FIG. 1A, the high voltage discharge center electrode 1815 is coupled to the high side of the MOSFET transistor(s) 1810*b*. The high voltage that is stored in the high voltage discharge capacitor(s) 1809 is sent to the high voltage discharge center electrode 1815, at the command of the micro controller 1818. When this signal is sent, the high voltage high side MOSFET 1810*b* conducts and the current/voltage flow down the high voltage discharge center electrode 1815. The voltage flows down the high voltage discharge center electrode 1815, where it makes contact with a conductive solution, such as a dielectric solution. The current flows through this liquid solution, completing the circuit path, through the high voltage discharge ground return electrode 1816, and the lower ground return electrode assembly 1817.

In an embodiment of the present invention, the lower ground return electrode assembly 1817 allows the liquid solution to enter the firing chamber through the vents at the bottom of the assembly (not pictured). When the tip assembly is submerged in the dielectric liquid solution, the circuit sends a high voltage pulse through high voltage discharge center electrode 1815, the high voltage current flows through the liquid solution causing an electrical discharge in the liquid solution. This discharge causes the cavitation shock wave, and completes the circuit path.

In the embodiment of FIG. 1A, the high side low side MOSFET 1810*b* is responsible for conducting and the current/voltage from high voltage discharge capacitor(s) 1809, down the high voltage discharge center electrode 1815. These functions involve one or more of amplifying and/or switching electronic signals. The use of a high side low side MOSFET in this embodiment is an example of an electrical component that may be utilized to perform this function. One of skill in the art will recognize that additional electrical components may be substituted for one or more high side low side MOSFETs and/or combined with one or more high side low side MOSFETs, to achieve the same functionality. Electrical components included in various embodiments of the invention to carry out the functionality attributed to the high side low side MOSFET 1810*b* include, but are not limited to, insulated-gate bipolar transistors (IGBTs), silicon-controlled rectifiers (SCRs), bipolar transistors (including NPN and PNP), and Darlington transistors.

Utilizing a high side low side MOSFET in embodiments of the present invention, rather than an alternative component that accomplishes equivalent functionality, may introduce certain advantageous electrical properties into the structure of the device. Advantages of using a MOSFET include, but are not limited to, limiting loss (MOSFETs are not lossy as compared to components with equivalent functionality) and providing a component with low impedance.

Returning to FIG. 1A, as recognized by one of skill in the art, electrical components utilized, in embodiments comparable to FIG. 1A, to conduct the current/voltage from high voltage discharge capacitor(s) 1809, down the high voltage discharge center electrode 1815 in place or in concert with one or more high side and low side MOSFET 1810*a* may utilize alternate drivers in place of the high side and low side MOSFET driver 1810*a*

FIG. 2 is another embodiment of the apparatus 200. Like the embodiment of FIG. 1, FIG. 2 utilizes a spark gap. FIG. 2 is designed to reflect the shape and ergonomic design of the apparatus. This embodiment is hand-held and therefore, the hand piece housing 201 is easily gripped and the embodiment of the apparatus easily manipulated by a user. On the end of the apparatus 200 is a replaceable tip 210, an embodiment of which is discussed further in reference to FIGS. 6-6F.

Like the embodiment of FIG. 1, the hand piece housing 201 of FIG. 2 is molded of a non-conductive material, such as plastic, and the hand piece housing 201 is also molded as such that allows for easy cleaning and easy replacement of the batteries 202 within. In another embodiment of the present invention, the housing is conductive and serves as a ground return. Embodiments that utilize plastic, non-conductive housings may reduce manufacturing costs.

The two compartments for the batteries 202 in this embodiment are shown as a non-limiting example. Depending upon the batteries selected, the number used to achieve the acoustical pulse generated by the apparatus varies. Batteries 202 utilized in this embodiment include but are not limited to 0.8 vdc-30 vdc batteries, and/or 180 vdc3-7 volt batteries. The low voltage of the batteries 202 is later magnified by additional components in the embodiment, as in the embodiment of FIG. 1, to drive the acoustical shock wave in the liquid solution that creates the acoustic effect used, for example, in endodontic irrigation.

The batteries 202 charge a low voltage DC power supply 205 with a power ground 204. A timing circuit 206 takes input from the low voltage DC power supply 205 while also taking input from a start/stop switch 208. The operation of the start/stop switch 208 by a user controls whether the apparatus is operational. This timing circuit 206 powers a high voltage igniter switch circuit 209. In this embodiment of the apparatus 200, the start/stop switch 208 controls the operation of the embodiment.

In this embodiment 200, the high voltage igniter switch circuit 209 is coupled to spark gap switch 208. Also coupled to the spark gap switch 208 is a high voltage DC power supply 207. The low voltage DC power supply 205, inputs to the timing circuit 206, which inputs to a high voltage DC power supply 207.

Figure 2A:
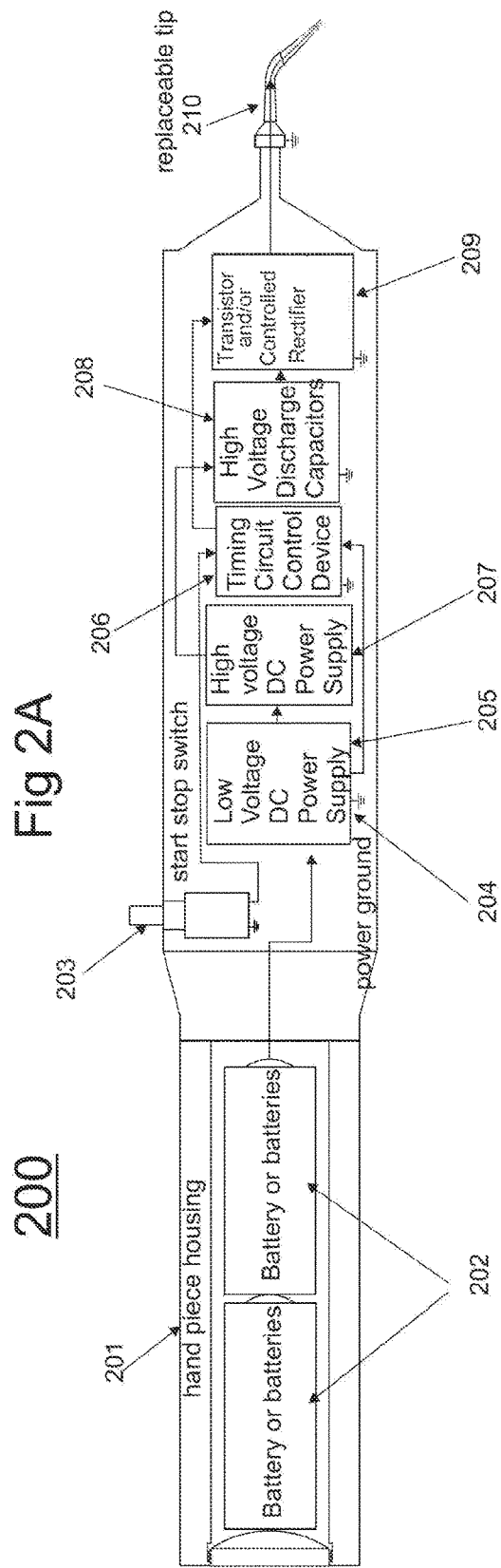
FIG. 2A depicts an aspect of an embodiment of the present invention.

Like FIG. 1A, the embodiment of FIG. 2A does not utilize a spark gap or an igniter. However, like the embodiments of FIG. 1A, the hand piece housing 201 of FIG. 2A is molded of a non-conductive material, such as plastic, and the hand piece housing 201 is also molded as such that allows for easy cleaning and easy replacement of the batteries 202 within. In another embodiment of the present invention, the housing is conductive and serves as a ground return. Embodiments that utilize plastic, non-conductive housings may reduce manufacturing costs.

Returning to FIG. 2A, the two compartments for the batteries 202 in this embodiment are shown as a non-limiting example. Depending upon the batteries selected, the number used to achieve the acoustical pulse (and control the cavitation) generated by the apparatus varies. Batteries 202 utilized in this embodiment include but are not limited to 0.8 vdc-30 vdc batteries, and/or 180 vdc3-7 volt batteries. In various embodiments of the present invention, the batteries are lithium and the voltage range is 3.6 v to 7.4 v. The low voltage of the batteries 202 is later magnified by additional components in the embodiment, as in the embodiment of FIG. 1A, to drive the acoustical shock wave in the liquid solution that creates the acoustic effect used, for example, in endodontic irrigation.

In the embodiment of FIG. 2A, the batteries 202 deliver voltage and current to operate the circuit. Voltage flows from the batteries 202 to the low voltage power supply 204, which regulates the power to all the integrated circuit and timing circuit 206. Voltage travels from the low voltage power supply 204 to the high voltage power supply 207, which converts the voltage from the batteries 202, to a higher voltage. For example, In various embodiments of the present invention, voltages can be converted from all 160 volts DC to as high as 300 volts DC, or higher.

In the embodiment of FIG. 2A, the timing circuit 206 is a micro controller device. In embodiments that utilize an LCD display, or any alternate, display, the timing circuit 206 controls this display. In the embodiment of FIG. 2A, the timing circuit 206 controls the start stop switch 203, period time, cycle time, pulse width time, and, if utilized in the embodiment, the start stop switch 203 also controls the electronic trim pot that controls the bus voltage.

The high voltage discharge capacitor 208 is connected to a transistor or a controlled rectifier 209, including but not limited to, a high side low side MOSFET(s), and the high voltage discharge capacitor 208 delivers the power in joules. The high transistor or a controlled rectifier (such as a high side low side MOSFET(s) and driver circuit(s)) 209 is/are controlled by the timing circuit 206. For ease of understanding, in FIG. 2A, the transistor or a controlled rectifier are depicted in a single element, but in embodiments of the present invention, this element can include, but is not limited to, a high side low side MOSFET(s) and driver circuit(s). In the transistor or a controlled rectifier 209, the timing circuit 206 controls the transistor or controlled rectifier. In embodiments that utilize a high side low side MOSFET(s) and MOSFET driver(s), the timing circuit 206 controls the driver circuits, which are connected to MOSFET(s). When the timing circuit 206 sends the signals to the devices, high voltage discharge capacitor(s) 208 delivers the energy to the tip assembly. Energy is discharged at the replaceable tip 210, which creates acoustical shock wave in the liquid into which the replaceable tip 210 is at least partially submerged.

One of skill in the art will recognize that in further embodiment of the present invention, additional electrical components may be substituted for one or more high side low side MOSFETs in embodiments where the high side low side MOSFET(s) and driver circuit(s) are used as the and/or combined with one or more high side low side MOSFETs, to deliver power from the high voltage discharge capacitor 208 to the replaceable tip 210. Electrical components included in various embodiments of the invention to carry out this functionality include, but are not limited to, a transistor, a controlled rectifier, insulated-gate bipolar transistors (IGBTs), silicon-controlled rectifiers (SCRs), bipolar transistors (including NPN and PNP), and Darlington transistors.

Figure 5:
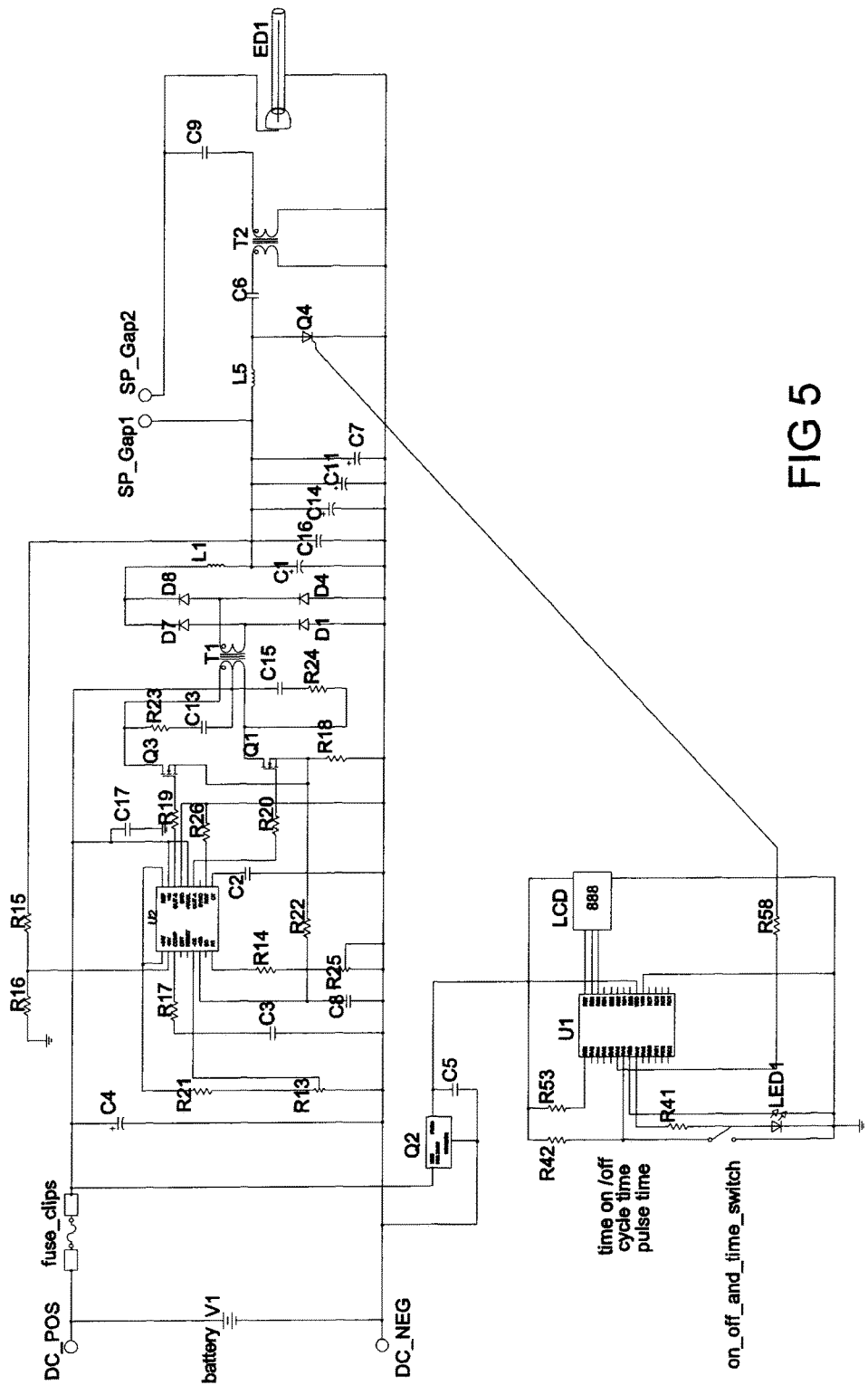
FIG. 5 depicts an aspect of an embodiment of the present invention.

FIG. 3 is a general workflow 300 of an aspect of the present invention utilizing an igniter, such as the embodiment of FIGS. 1 and 5. Throughout FIG. 3, references are made to the elements of FIG. 2 for clarity. However, FIG. 2 is only one embodiment of the apparatus. The workflow 300 is applicable across further embodiments of the apparatus. FIG. 3A, discussed after the discussion of FIG. 3, is a workflow relevant to embodiments, such as the embodiment of FIG. 1A, which do not utilize a spark gap and/or an igniter.

Referring to FIG. 3, the battery or batteries 202 deliver the voltage and current to operate the circuit (S310). The low voltage dc power supply 205, which in FIG. 2 is small enough to fit in a hand held device, and the timing circuit 420, convert the low voltage to a high current/voltage (S320). The high voltage igniter switch circuit 209 produces a very sharp high voltage spike that is low in current (S330). The high voltage spike breaks down the air gap switch 208 (S340) in an embodiment with this component, and/or is injected directly utilizing a MOSFET high side and low side. When the spark bridges the air gap, the gap becomes conductive and it allows all the stored energy to discharge completely (S350). In various embodiments of the present apparatus, this energy is stored in capacitors, like the high voltage capacitor 109 in FIG. 1.

When the stored energy discharges, the tip of the apparatus 210 tip is in the liquid solution and the energy travelling through the tip 210 creates an acoustical shock wave in the liquid (S360). Once a wave is created, the process repeats as the batteries 202 continue to deliver voltage to the circuit (S310).

In an embodiment of the present invention, the electrical discharge achieved in FIG. 3 (and described in reference to FIG. 1) delivers more than just an acoustical wave to combat foreign agents, such as bacteria. The electrical discharge at (S350) delivers the aforementioned acoustical shock waves, cavitation within the liquid medium, UV radiation, hydrated electrons, OH radicals, $H_2O_2$, nanoparticles, and positive and/or negative ions (of embodiments of the present invention that utilize metal electrodes in the tip, discussed later in FIG. 6). This embodiment may deliver one or more of the following: UV light, hydrated electrons, OH radicals, $H_2O_2$, $H_3O$, $O_2$, $MnO_2$, $O_3$ (ozone), O, $HO_2$, electrons, positive or negative ions, reactive chemical radicals, hydroxyl radicals, super oxides, nanoparticles, and/or any other known anti-pathogen, anti-chemical pollution, chemical reactions.

FIG. 3A is an exemplary workflow on an embodiment of the present invention that utilizes circuitry similar to FIGS. 1A and 2A, i.e., there is no igniter nor spark gap. In this workflow, in an embodiment of the present invention, the batteries (or alternate power source), deliver voltage and current to operate circuit (S310). The circuit converts the low voltage from the batteries to a higher voltage (S320).

This now higher voltage is sent to a capacitor (S330) and from the capacitor, to a high side low side MOSFET (S340). Once the MOSFET high side turns on and energy is discharged at the tip (S350), the tip creates acoustical shock wave in liquid (S360).

In an embodiment of the present invention, the electrical discharge achieved in FIG. 3A (and described in reference to FIG. 1A) delivers more than just an acoustical wave to combat foreign agents, such as bacteria. The electrical discharge at (S350) delivers the aforementioned acoustical shock waves, cavitation within the liquid medium, UV light, hydrated electrons, OH radicals, $H_2O_2$, $H_3O$, $O_2$, $MnO_2$, $O_3$ (ozone), O, $HO_2$, electrons, positive or negative ions (of embodiments of the present invention that utilize metal electrodes in the tip, discussed later in FIG. 6), reactive chemical radicals, hydroxyl radicals, super oxides, nanoparticles, and/or any other known anti-pathogen, anti-chemical pollution, chemical reactions.

The electrical discharges created by the electrodes in the tip of an embodiment of the present apparatus create shock waves that are high pressure and therefore, damage the bacterial membranes due to the difference in pressure. The destroying effect on bacteria due to this pressure difference is realized more intensely with faster discharges and/or for acoustic waves on destroyed cells.

In an embodiment of the present invention, shock wave forces the irrigant through the small lateral canals at a pressure that achieves irrigation of main canals coupled with irrigation of small and tiny lateral canals, including those that are oddly shaped. By utilizing an embodiment of the present invention, If a lateral comes off of a tooth, because the lateral stems off the root canal, the tip can be positioned such that the discharge that is next to the lateral canal and will drive the irrigant directly into the lateral. In an embodiment of the present invention, the electrode in the tip, discussed further in FIG. 6, is small so that it can go down the canal and/or be placed in close proximity.

Discharging one or more embodiments of the tips of embodiments of the present device into the air and/or at the air/water interface may provide some benefits. In embodiments of the present invention, a tip with a conductive solution in its chamber can be discharged into the air and may results in positive, purifying, benefits for the air, such as ionization. As discussed later, an embodiment at the tip that is discharged at the point where the air and the water (or other conductive liquid) meet with also provides one or more of the benefits discussed in relation to discharging wholly into a dielectric fluid. In embodiments of the present invention, moisture in the air could assist in conducting the discharge.

In addition to OH and $H_2O_2$, other products of this electrical discharge include, but are not limited to, H*, O*, and $O_3$ (ozone), which together with OH and $H_2O_2$ act as oxidizing agents. The electric fields of these discharges are lethal to several kinds of microorganisms. Additionally, $H_2O_2$ and $O_3$ dissociate into free radicals and these free radicals oxidize organic components. OH* also oxidizes organic components. These particles oxidize organic components both above and below the surface of the irrigant.

The UV radiation also oxidizes organic compounds in the irrigant. Thus, combining the shock wave with these oxidizing agents serves to sterilize the irrigant.

After the OH radicals, the $H_2O_2$, and the hydrated electrons have dissipated, i.e., after no more than several days, the nanoparticles and positive and/or negative ions of metal, which are produced by the erosion of the electrodes, continue to provide anti-bacterial benefits. In an embodiment of the present invention, the erosion of the electrodes is lessened by running an embodiment of the described apparatus at lower energy levels The decreased erosion enables the use of a wide variety of different material systems, systems produced from finer gauged (thinner) electrodes and provides a working system that does not destroy itself through cavitation-produced erosion. As aforementioned, use of embodiments of the invention may produce the following: UV light, hydrated electrons, OH radicals, $H_2O_2$, $H_3O$, $O_2$, $MnO_2$, $O_3$ (ozone), O, $HO_2$, electrons, positive or negative ions (of embodiments of the present invention that utilize metal electrodes in the tip, discussed later in FIG. 6), reactive chemical radicals, hydroxyl radicals, super oxides, nanoparticles, and/or any other known anti-pathogen, anti-chemical pollution, chemical reactions.

One manner in which the nanoparticles destroy bacteria is by penetrating the bacteria and emitting ions which are toxic to bacteria. When nanoparticles are in close proximity to bacteria, directed streams of toxic ions appears, which produce a bactericidal effect. Thus, this cooperative residual bactericidal effect is accomplished at least in part by the actions of nanoparticles and positive and/or negative ions emitting by them. The residual effects of the nanoparticles and positive and/or negative ions of metal are realized for a duration including but not limited to several months.

Embodiments of the present invention can be used both in concert with and without the NaOCl and EDTA protocol to remove all of the nerve and infected materials, clean the smear layer, and kill bacteria or pathogens. When used in conjunction with the NaOCl and EDTA protocol, this apparatus and method would kill remaining bacteria and pathogens that remain after the protocol and provide residual effects that the protocol does not provide. When used without the protocol, the apparatus and method could provide the listed functionality without introducing a biologically toxic substance into the body. Irrigants that can be used include, but are not limited to saline solution, hydrogen peroxide, glutaraldehyde, and/or any antibiotic and/or antimicrobial solution.

Figure 4:
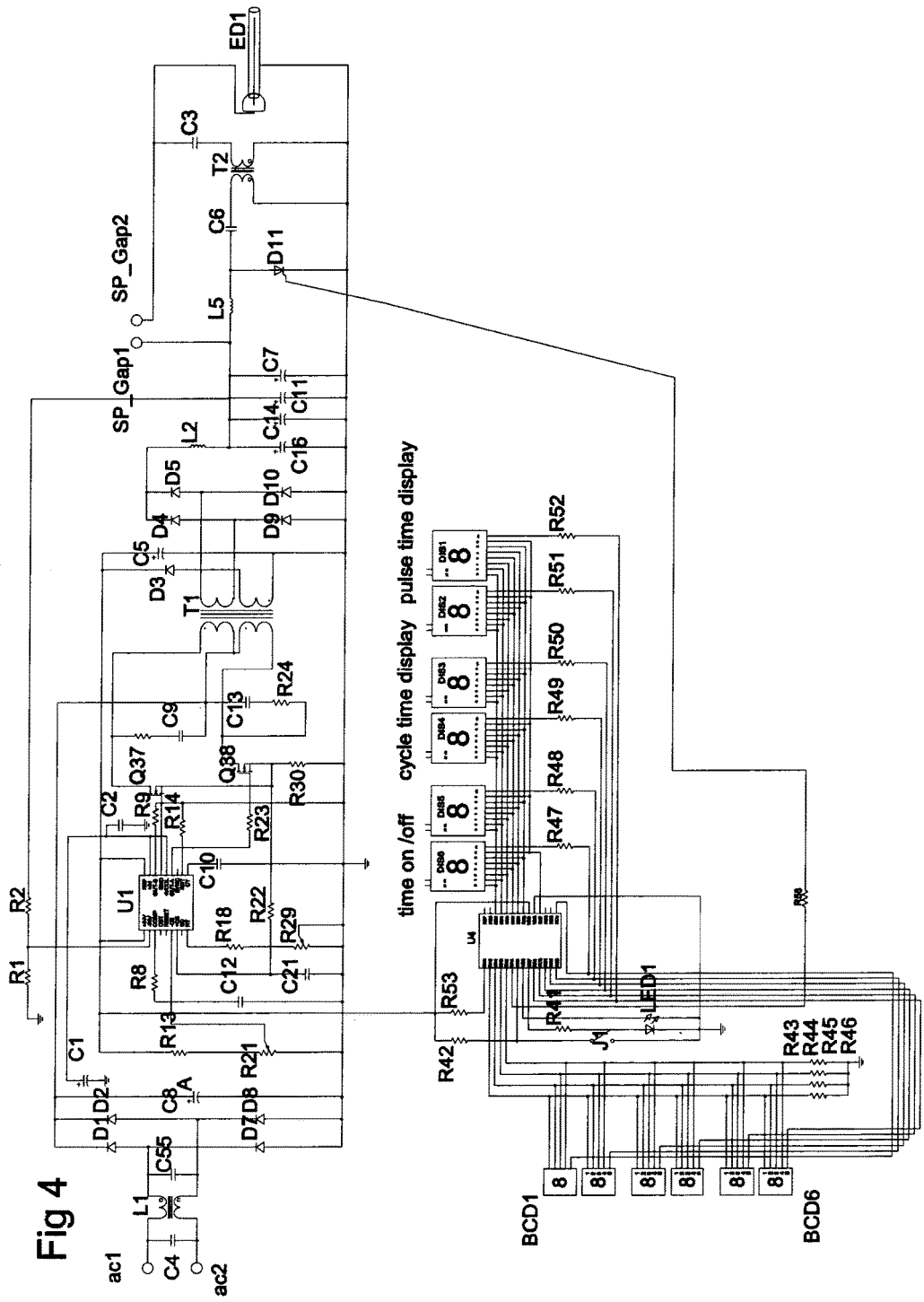
FIG. 4 depicts an aspect of an embodiment of the present invention.

FIG. 4 depicts an embodiment of the circuitry utilized in an embodiment of the present apparatus. This apparatus practices the workflow 300 of FIG. 3. The electrical elements of FIG. 4 are enclosed in a non-conductive housing (not pictured). The circuit details provided in FIG. 4 are an example of a possible configuration of circuit components utilized to practice the method disclosed. One of skill in the art will recognize that certain components can be substituted and still create an irrigating acoustic wave. For example, FIG. 4 features seventeen capacitors C1-C17, which is only one example of how capacitors can be configured in the circuitry of the present apparatus.

The functions of the apparatus in FIG. 4 are programmable by utilizing a micro chip controller U1. The micro chip controller U1 controls all timing functions, including but not limited to period time and cycle time (Hz). The pulse time is a function of the stored energy, which is measured in micro seconds.

The embodiment of FIG. 4 is powered by a lithium battery V1. The lithium battery V1 is a low voltage battery with a voltage range of 0.8 vdc-30 vdc. A further embodiment of the present invention utilizes batteries with a range of 3-7 volts. Further embodiments of the present apparatus employ additional power sources with voltages within this range. As discussed in reference to FIG. 1-2, in this embodiment, this low voltage power source is later converted to a high voltage in order to create the acoustical waves that agitate liquid through the tip (not pictured) of the apparatus and irrigate dental structures in the mouth of a patient. A safety fuse F1 is additionally incorporated in this embodiment. A filter capacitor C4 is used to eliminate any electrical noise that may be generated by the switching power supply or other IC's in the embodiment. The switching power supply U2 converts the low battery voltage to a high bus voltage, which includes but is not limited to a range of 250 vdc to 500 vdc and/or a range of 180 vdc-250 vdc.

As seen in FIG. 4, this switching power supply U2 utilizes supporting passive and active components to set up all the levels and references. Included in these components are the 5 volts references, resistors R13, R21, which are tied to the switching power supply U2. Meanwhile, resistors R15 and R16 form a voltage divider feedback loop and are tied to the high voltage bus output. Additional resistors R19 and R20 limit the current to the gates of the MOSFETs Q1, Q3 and the IC maximum current drive output. The MOSFETs switch the high frequency transformer together with switching power supply U2 and drive them to switch on and off at a predefined frequency. Resistor R18 works as a current sensing resistor and implements electrical resistance in the circuit. Meanwhile, resistor R22 and capacitor C8 act as a buffer filter to eliminate spikes caused by switching the inductive load.

FIG. 4 utilizes a high frequency ferrite transformer T1, including but not limited to a ferrite core transformer. The high frequency transformer T1 includes MOSFET pins 1 and 3, so-called because they are tied to the MOSFETs Q1, Q3. MOSFET pin 2 is tied to the power supply, in this embodiment, a 0.8 vdc-30 vdc battery supply. Further embodiments utilize a variety of power supplies, including but not limited to, one or more 3-7 volt batteries. The AC output pins 4, 5, of the high frequency transformer T1 feed diodes D1,D4,D7 and D8, which are set up as a full wave bridge rectifier, converting the rectified AC to DC. Resistor R23 and capacitor C13 acts as an RC snubber as does resistor R24 and capacitor C1; RC snubbers work like filters and keep spikes and radio frequency interference (RFI) noise to a minimum.

In the present embodiment, Inductor L1, together with capacitors C1, C16, C14, and C11 filter and store the energy that will be discharged at a high current rate. Specifically, Inductor L1 saturates when capacitors C1, C16, C14 and C11 are discharged.

The high voltage igniter portion of the circuit is comprised of inductor L5, MOSFET Q4, capacitor C6, and transformer T2. Capacitor C9 acts as a blocking capacitor and prevents the high discharge capacitor stored current from damaging transformer T2. As in the embodiment in FIGS. 1 and 2, an air gap SP_Gap1-SP_GAP2 is used as a switch, which loads as the capacitors C1, C16, C14, C11 are charged. The bus voltage is sufficient to cause break down of the liquid solution which is somewhat conductive. Therefore, the capacitor C9 protects the transformer T2 from being loaded down.

FIG. 5 depicts the circuitry utilized in an embodiment of the present apparatus. The circuitry is similar to FIG. 4, but the apparatus utilizes a different control for user input. Both the embodiment of FIG. 4 and the embodiment of FIG. 5 are programmable by utilizing a micro chip controller U1. In FIG. 5, the user adjusts settings by utilizing user BCD switches BCD1-BCD6 to set the period time and cycle time. These settings are obtained by micro chip controller U1. Light-emitting diode (LED) displays DIS1-DIS6 display the countdown timer, displays DIS5-DIS6, the cycle time, displays DIS3-DIS4, and the pulse time, displays DIS1-DIS2, to a user.

FIG. 4 utilizes an LCD display LCD1 to display the countdown timer, cycle time, and pulse time to a user.

Figure 5A:
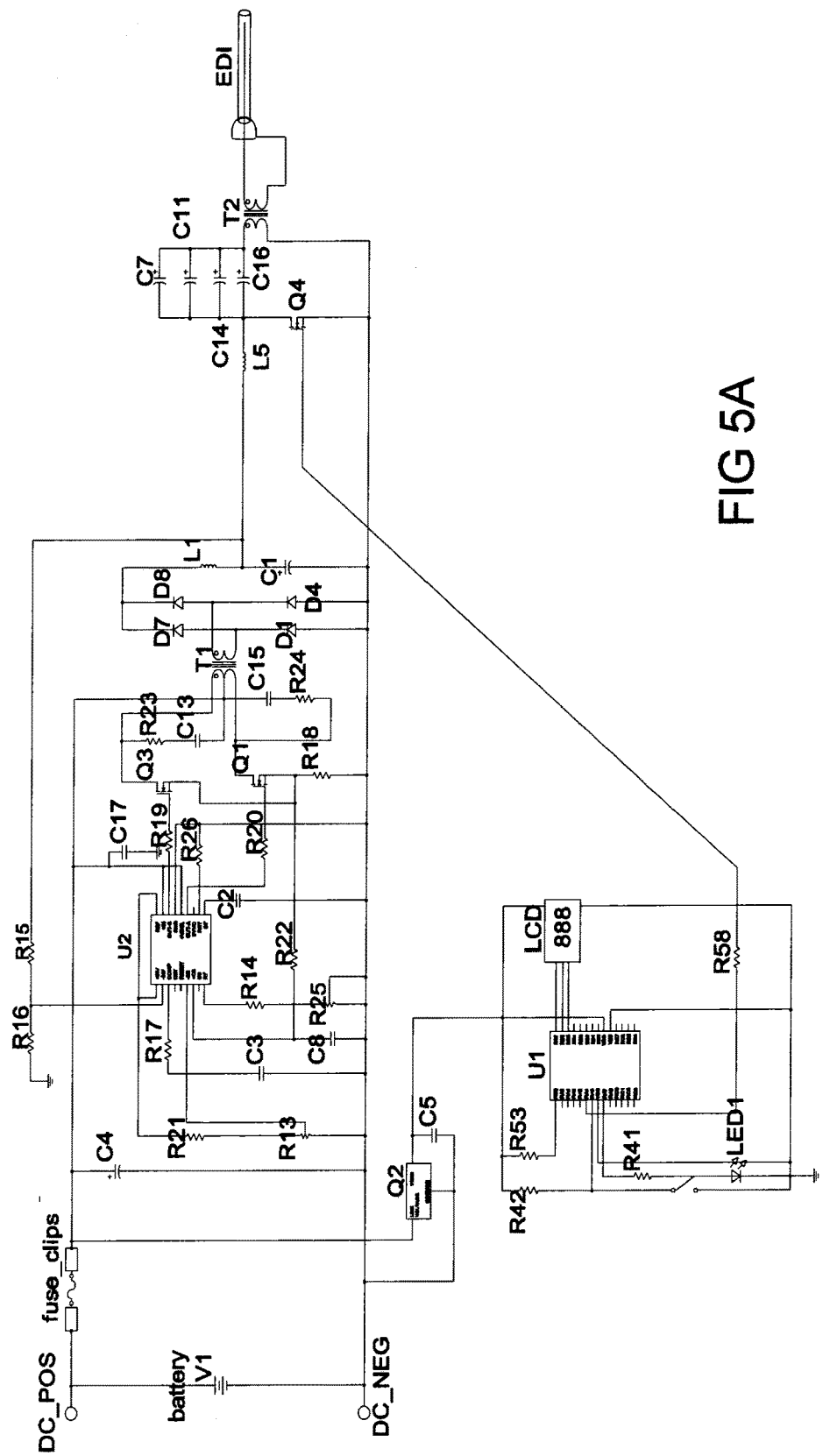
FIG. 5A depicts an aspect of an embodiment of the present invention.

FIG. 5A also depicts circuitry utilized by an aspect of an embodiment of the apparatus. In the embodiment of the apparatus that utilizes the circuitry of FIG. 5A, power is delivered to the tip (not pictured) differently. Like FIG. 1A, this embodiment does not utilize a spark gap to create an acoustic wave.

Referring to FIG. 5A, voltage/current travels to inductor L5 and to one or more capacitors C7, C11, C14, C16, including but not limited to, one or more photo discharge capacitors. The four capacitors utilized in FIG. 5A are depicted as an example as additional embodiments utilize different numbers of capacitors as needed depending upon the use, among other factors. Once charged, capacitors C7, C11, C14, C16 discharge at the primary of transformer T2.

In this embodiment, transformer T2 delivers a high voltage spike and current to cause an acoustical shock wave. Transformer T2 is robust as it delivers both a high voltage spike and enough current to cause the acoustical shock wave. Transformer T2 is rendered robust by a thick wire and its configuration. Not only is the wire thick, the secondary of transformer T2 is isolated from the circuit and connected directly to electrodes in the tip (not pictured).

Before the voltage/current flows through inductor L5 and charges capacitors C7, C16, C11 and C14, MOSFET Q4 gets an instruction micro chip controller U1. The micro chip controller U1 applies voltage, including but not limited to, 5 volts, to the gate of the MOSFET Q4, so that it conducts the voltage/current. The MOSFET Q4 then turns and it discharges all the stored energy from capacitors C7, C16, C11 and C14 into transformer T2, which causes inductor L5 to momentary saturate. Transformer T2, now at a high impedance state, delivers a high voltage spike and current to cause an acoustical shock wave.

Figure 5B:
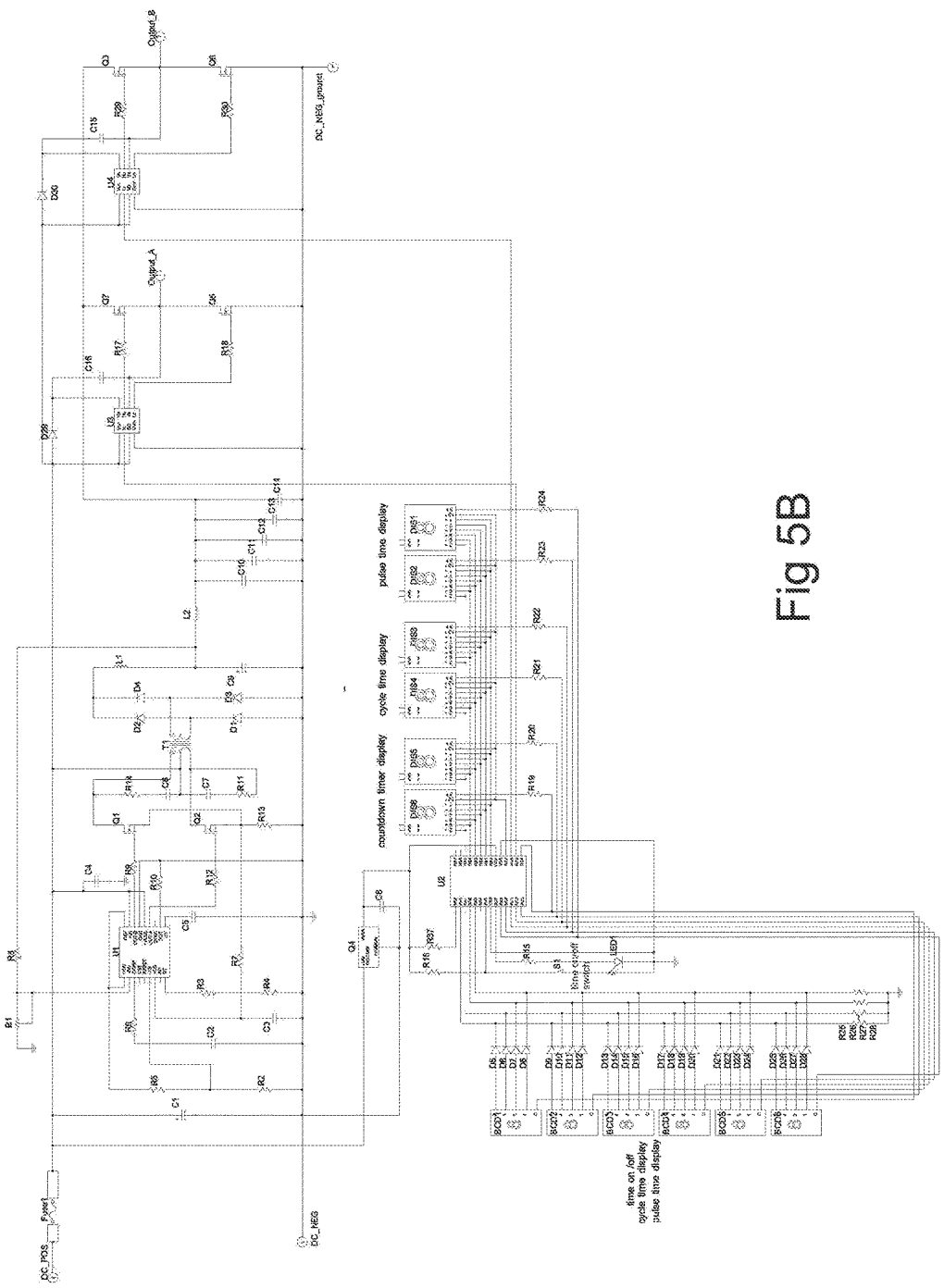
FIG. 5B depicts an aspect of an embodiment of the present invention.

Like FIG. 5A, FIG. 5B is a schematic of an aspect of an embodiment of the present invention that does not utilize a spark gap. The embodiment of FIG. 5B can deliver a DC pulse or an AC pulse to a tip. To this end, the embodiment of FIG. 5B utilizes a high side low side MOSFET pairs to deliver the stored energy in the discharge capacitors and deliver the stored energy into the tip.

Referring to FIG. 5B, a power source that can be utilized by this embodiment is a lithium battery pack from 3.6 vdc to 7.4 vdc. One advantage of this power source is that these batteries type packs are standard.

In the embodiment, the low voltage of the battery pack flows into two directions. The first direction is to the low voltage regulator that regulates the power to all the integrated circuits and the micro controller device. The second direction is to the switching IC driver.

The IC driver can operate in two modes: fly back or push pull. In FIG. 5B, the IC driver is in the second mode. This switching IC drive, drives MOSFETs Q1, Q2, which are coupled to Mosfets, they are coupled to the primary high frequency ferrite transformer T1. The primary high frequency ferrite transformer T1 the lower DC battery voltage to a higher voltage. In some embodiments of the present invention, the higher voltage ranges from 160 volts to well over 300 volts AC.

Returning to FIG. 5B, the now higher voltage, the AC voltage flows to diodes D1, D2, D3, D4, which are set up as a bridge rectifier. The rectified voltage then flows through inductor L1, which filters out the ripple current. The voltage then flows into the filter capacitor C9 and continues to flow through inductor L2 and flows into the high voltage discharge capacitors. The high voltage discharge capacitor, which are coupled to the high voltage the MOSFETs Q1, Q2.

An embodiment of the tip 600 of an embodiment of the apparatus is shown in FIG. 6. The tip 600 appears as an integrated unit, but is separated into components to understand its functionality. During use, the end of the tip 600 is inserted in the mouth of a patient and in some applications, such as cleaning fissures, it may be embedded in a specific tooth that is being irrigated. The tip 600 connects to the body of the apparatus with a connector 602 that is integrated into the tip design. In the embodiment of FIG. 6, the connector 602 is a screw-type connector with threading. The receptors of the threading are located on the body of the apparatus (not pictured).

Like the hand held portion discussed in earlier figures, the tip 600 is comprised of a housing 601. This housing 601 on the tip 600 is comprised of a conductive material, including but not limited to, metal, such as stainless steel. This housing 601 is conductive because it doubles as a ground return electrode. The housing 601 is shaped with a bend that is utilized to manipulate the tip into the mouth of a patient and into the dental structure, such as the tooth, that the user of the apparatus desires to irrigate.

Although a continuous housing 601, the upper portion of the housing 609, and the lower portion of the housing 610 have differing characteristics. To protect the internal elements, in an embodiment of the present invention, the upper portion of the housing 9 is thick and rigid. The lower portion of the housing 610 is comprised of a material that is both conductive and flexible, such as a flexible stainless steel tube. The lower portion of the housing 610 is comprised of a first portion 611 and a second portion 612. The first portion 611 is solid while the second lower portion 612 is porous. The porous second lower portion 612 allows an electrical discharge to occur in the lower part of the tip 600 and permeate the tip into the liquid.

Internal to the housing 601, is a center electrode conductor 603, which conducts the charge through the tip 600. This center electrode conductor 603 is insulated using a layer of insulation 606 throughout the length of the tip 600 and the center electrode conductor 603. A porous portion of insulation 608 surrounds the lower center firing electrode 604. As discussed later in accordance with different tip configurations, clearings, also called perforations, in the insulation enable embodiments of the system to fire, i.e., match the central electrode with the ground electrode. For example, the location of one or more perforations in a tip defines where the sparks, cavitation, compression, nanoparticle evolution occurs. As recognized by one of skill in the art, utilizing tips with different placements for perforations is useful in increasing the efficacy of different treatments. In a method of manufacturing embodiments of the tips, an insulating layer is placed on the center electrode and selectively removed, thereby defining the proximity of electrical coupling between the center electrode and the ground return. Electrical coupling occurs where the insulation layer has been removed.

In an embodiment of the present invention, the lower center firing electrode 604 is the center electrode 115 referenced in FIG. 1. In an embodiment of the invention, the lower perforated return electrode 605 is the ground return electrode 116 referenced in FIG. 1, and the insulation 606 and the perforated return electrode 605 comprise the a lower electrode assembly 117 and firing chamber referenced in FIG. 1. In an embodiment of the present invention, the center electrode 115 is centrally located in the tip, evenly from all walls.

In embodiments of the present invention, the center firing electrode 604 is either a positive or a negative electrode, and the lower perforated return electrode 605 is either a negative or a positive electrode. In each embodiment, the center firing electrode 4 has a charge that opposes that of the lower perforated return electrode 605. One of skill in the art will recognize that a center electrode and a ground electrode, regardless of charge, may be adapted to create the desirable electrical events within the tip of embodiments of the present invention.

Returning to FIG. 6, the lower center firing electrode 604 is embedded in the tip 600, while the lower perforated return electrode 605 is located in the outside of the tip 600. The porous second lower portion 612 of the tip 600, the porous portion of insulation 608 surrounding the lower center firing electrode 604, and the perforated return electrode 605 allow liquid solution to make contact with the lower center firing electrode 604. The conductive liquid bridges the connection between the lower perforated return electrode 605 and the lower center firing electrode 604 so that the tip can deliver acoustic waves into the area targeted by the tip. The lower center firing electrode 604 transfers the energy into the liquid solution that causes the acoustical shock wave, while the holes in the lower perforated outside return electrode 605 allow the acoustical shock wave to penetrate into the liquid solution and enable the liquid solution, which embodies the aforementioned antimicrobial properties, to flow from the inside of the tip to the dental surface being worked upon, for instance, a root canal.

Flexible outside and inside lower electrodes 607 assist in positioning the tip 600 to deliver the acoustic waves to a targeted area. Specifically, the flexible outside and inside lower electrodes 607 allow the tip 600 to be worked into the tooth or the root canal for performing the irrigation of the root canal and laterals. Many infections within a root canal are introduced during the dental procedure. Because the use of the tip of FIG. 6, for example, offers real time bioremediation during the dental process, its use reduces the introduction of foreign species to the inside of a tooth.

In an embodiment of the present invention, the electrodes utilized include silver. Water treated with silver electrodes has the highest bactericidal activity because ions of silver have the highest toxicity to bacteria; it is an anti-pathogen. Thus, the nanoparticles created by the silver electrodes also combat the bacteria and foreign particles in the canals. Further embodiments of the present invention utilize electrodes comprised from additional materials that are biologically inert. Materials used to comprise the electrodes include but are not limited to silver, copper, stainless steel, ceramic, carbon-based material, iron, and/or other conductive materials. The suspensions utilized with an embodiment of the present invention can also contain nanoparticles, which further aid in the efficacy of embodiments of the device in combating bacteria and foreign particles. In embodiments of the present invention, sonoluminescence, as described earlier, may occur during treatment and provides light at the working surface which assists an operator in confirming the actuation of the device as well as providing UV light which is known to further remediate microbial/biologic species.

As aforementioned, the tip of an embodiment of the apparatus may be removable and may be switched out with different tips that are more suited for different applications. In embodiments where the tips are not removable, the tip design may vary to maximize efficacy across varying uses. FIGS. 6-6F show embodiments of various tips designed to accomplish different tasks in embodiments of the present invention. For example, FIG. 6A shows an embodiment of a tip that is designed to fire at the surface. The tip 601 has a larger opening at the bottom 613 to fire onto a greater surface. Each of the tips helps control cavitation.

In the tips of embodiments in FIGS. 6-6F an electrical discharge is produced between a centrally located electrode and a ground return and creates a cavitating bubble and therefore, ionic species, nanoparticles, pathogen killing agents etc. In the tips in FIGS. 6-6F, the cavitating bubble further produces a force capable of moving the working fluid down the inside of the ground return tube of the top, exiting the ground return tube via machined water vents, also referred to as orifices, in various tip embodiments. In tips that include these vents, the position of the vents on the tip and the shape of the vents help define the position, magnitude and direction of the exiting working fluid.

In the present application, the terms vents, holes, orifices, openings, and apertures, are used interchangeably.

Embodiments of the tips include different numbers of vents, different vent positions, and particular vent angles, which facilitate the movement of the conductive medium, including but not limited to, the working fluid in a particular direction from the inside of the dental tip, to the outside of the dental tip, into the root canal. In some embodiments of the tips, the angle and position of the vents is defined to match the known angles of laterals within a tooth. For example, that laterals in the center of the tooth exit/enter the root canal at approximately 90 degrees to the root canal, while laterals positioned towards the bottom of the root canal exit/enter the root canal at approximately 60 degrees. Matching of these angles focuses the cavitation produced species and/or the plasma into the lateral canals at optimum angles. However, depending upon the anatomical structure targeted and the cavity into which an embodiment of the device is at least partially inserted, the angles of the openings can vary anywhere from 0-180 degrees relative to a longitudinal axis.

In some embodiments of the tips of the present invention, a small amount of epoxy resin is applied to the insulating shrink tubing upon construction. The resin keeps water from firing up the tube, effectively forcing the water to egress via the engineered orifices.

Referring to FIG. 6A, the tip 601 utilizes a connector 602, including but not limited to a screw-type connector with threading. Further embodiments of this tip 601 may utilize additional fasteners. Returning to FIG. 6A, when threading serves as the connector 602, the receptors of the threading are located on the body of the apparatus (not pictured).

Tip 601 is comprised of a housing 601, which is comprised of a conductive material, including but not limited to, metal, such as stainless steel which doubles as a ground return electrode and is shaped with a bend that is utilized to manipulate the tip into the mouth of a patient. The upper portion of the housing 609 is thick and rigid. The lower portion of the housing 610 is may be comprised of a material that is both conductive and flexible, including but not limited to, a flexible stainless steel tube. Although embodiments of the present invention utilize inflexible elements and materials, flexible materials provide advantages in ease of use. The lower portion of the housing 610 is comprised of a first portion 611 and a second portion 612. The first portion 611 is solid while the second lower portion 612 is porous. The porous second lower portion 612 allows an electrical discharge to occur in the lower part of the tip 601 and permeate the tip into the liquid.

The tip 601 features at least two electrodes, a center electrode and a ground electrode. The electrodes may be comprised of a metal and/or other conductive materials with anti-bacterial properties, including but not limited to, silver.

Internal to the housing 601, is a center electrode conductor 603, which conducts the charge through the tip 601 and is insulated using a layer of insulation 606 throughout the length of the tip 601 and the center electrode conductor 603. A porous portion of insulation 608 surrounds the lower center firing electrode 604. The lower center firing electrode 604 is embedded in the tip 601, while the lower perforated return electrode 605 is located in the outside of the tip 601. The porous second lower portion 612 of the tip 601, the porous portion of insulation 608 surrounding the lower center firing electrode 604, and the perforated return electrode 605 allow liquid solution to make contact with the lower center firing electrode 604. The conductive liquid bridges the connection between the lower perforated return electrode 605 and the lower center firing electrode 604 so that the tip can deliver acoustic waves into the area targeted by the tip. The lower center firing electrode 604 transfers the energy into the liquid solution that causes the acoustical shock wave, while the holes in the lower perforated outside return electrode 605 allow the acoustical shock wave to penetrate into the liquid solution.

In embodiments of the present invention, the liquid solution is within said tip and the shock waves initially interact with the liquid solution inside the tip. The holes in the tip allow the cavitated solution to exit the tip into the root canal. The acoustic waves exit the tip through the tip walls and via the holes.

Embodiments of the present invention utilize electrodes that are both flexible and inflexible, however, flexible outside and inside lower electrodes 607 assist in positioning the tip 601 to deliver the acoustic waves to a targeted area Although flexible tips assist in positioning the device for efficacy in certain uses, even when a tip is flexible, it is desirable to maintain the spacing between electrodes to perform certain procedures more effectively. Specifically, the flexible outside and inside lower electrodes 607 allow the tip 601 to follow the natural curvature of the tooth or the root canal for performing the irrigation of the root canal and laterals.

In embodiments of the tips, as aforementioned, the spacings of electrode may contribute to the utility of the device for a specific purpose. In one or more of the tips discussed, the described electrical discharge takes place at that the shortest distance between the center electrode and the ground return. Thus, centering the noted "center" electrode balances the discharge. If an electrode is positioned within the chamber at an angle, i.e., it is closer to one side of the chamber than the other, the discharge will take place preferentially at the closest gap. The cavitation and the resulting microjets may impinge upon the working surface, producing erosion and a change in the topology of the surface and hence, may re-define the position of the shortest distance. Utilizing different orientations for the electrode within the tip, different sizes for the electrode and the tip, different spacings between the electrode and the closest inside surface of the tip, different shapes for the electrodes, and different shapes for the inside surface of the tip that is closest to the electrode, will affect the functionality of the device. Therefore, different combinations of these changeable factors may be best suited for different functions.

The end 614 of the tip 601 is fitted with a screen 613. The screen 613 has a slight angle with a bigger opening at the bottom. Tip 601 is utilized in one aspect to fire at the surface. Thus, the greater surface area allows greater and more concentrated dispersion of firing discharges, including but not limited to cavitation products, including but not limited to, microjets, nanophase and sub-nanophase materials, plasma discharge and the UV, ozone, shock wave, radicals, and ions pulse at the surface. The screen 613 is part of the ground return and prevents an electrical charge from passing the end of the tip and having an adverse effect on a patient being treated. In embodiments of the present invention, the screen 613 performs as a Faraday cage.

The descriptors used for the components in the tip embodiments of FIGS. 6B-6F differ slightly from those used describing tips 6-6A. However, one of skill in the art will recognize that the incorporation of aspects of the present invention, i.e., using a central electrode and a ground return to produce and control an electrical discharge. Like with FIGS. 6-6A, in FIGS. 6B-6F certain numerals are repeated between figures to highlight structural similarities in these embodiments.

The diameters of embodiments of the tips in FIGS. 6B-6F vary and include, but are not limited to, an outer diameter of 0.062" with a taper down to 0.046" at the working end of the tip 620. The tips include a first end, a second end, and a longitudinal axis extending between them. In the embodiments of FIGS. 6B-6F, a center electrode 624 runs along the longitudinal axis. However, as discussed later, varying the positioning of the center electrode 624 within a tip can vary the functionality of the tip.

Referring to the embodiments of FIG. 6B-6F, the tips in these embodiments are utilized when a charge defined, for example, by the electronics in the hand piece (not pictured) is supplied to the center electrode conductor 624, which is comprised of a conductive material, for example, stainless steel. In embodiments of the invention, the charge to the center electrode conductor 624 can be adjusted by the operator through a handset (not pictured). Insulation in these embodiments is provided by a layer located between the center electrode conductor 624 and the ground return tube 625, called the insulating shrink tube 632, which and is comprised, in this embodiment, of an insulating material, such as an insulating plastic. The ground return tube 625 is comprised of a conductive material, including but not limited to, stainless steel. Portions of the insulating shrink tube 632 in each tip are selectively removed to define specific areas where electrical coupling between the center electrode conductor 624 and ground return tube 625 can occur. On the outside of the ground return tube 625, vents can be added by machining techniques in order to control the egress of liquid from the tip.

In the embodiments of FIGS. 6B-6F, a screw-type connector with threads 622 is used to attach the tip to a handset (not pictured). The handset includes the electronics to run the tip and the delivery of the working fluid (liquid solution). A plated metal insert 624 facilitates the electrical connection between the tip and the handset. A liquid solution is introduced into the chamber 628 between the ground return tube 625, and the center electrode conductor 624 by way of a liquid solution input vent 627. In these embodiments, an insulating plastic insert 629 secures and positions the center electrode conductor 624 in the center of the ground return tube 625. The insulating plastic insert 629 also insulates a central assembly 630. The central assembly 630 includes a plated metal insert 631 and the center electrode conductor 624, which is coated in the aforementioned insulating shrink tube 632. In each tip, cavitation products exit the tip through at least one vent 663. Various tips may include or exclude one or more holes at an end, also referred to herein as the apex, of the tip. Those tips that do not include one or more holes at the apex would irrigate approximately 90 degrees from the length of the tip.

The tips in FIGS. 6B-6F all provide a focused, repeatable and adjustable way to accomplish different dental goals, for example, boring into a tooth's interior, irrigating lateral canals, remediating biological species etc., irrigating, which assists in debris removal. During operation, sonoluminescence can occur and provides light at the working surface, which assists an operator in confirming the actuation of the device as well as providing UV light which is known to further remediate microbial/biologic species.

The aforementioned adjustment is facilitated in embodiments of the present invention by a change in power settings and thereby offers differing amounts of boring force. Embodiments of the present invention include preselected power settings that can be programmed into the hand piece (not pictured). Focusing is a function, in embodiments of the present invention, of power, frequency and duration settings, the shape of the egress hole(s) in the tip design located at the working end of the tip and further accentuated by the tapering of the working end (or exit nozzle) of the tip design, and any additional vents in the ground return tube. In embodiments of the present invention, the three dimensional shape of the egress orifice(s) can further define the resulting stream of working fluid.

Referring the FIG. 6B, the tip embodiment 620, a single vent 663 is at the end, apex 664 of the tip 620, adapting the tip 620 for boring. The tip 620 can be used, due to the single vent 663, to open up the crown of a tooth, thereby facilitating access to the inside of the tooth (i.e. access to the root canal). When providing accessing to the inside of the tooth, the design of the tip 620 also minimizes introduction of foreign species to the tooth's interior because its advantages include, but not limited to, constant irrigation, in situ remediation species as previously discussed, and exemplary access to root interior.

This tip 620 provides an alternative to a standard dental drill commonly used to open a tooth crown gaining access to the enclosed root canal. In addition to facilitating drilling, the tip 620 offers bioremediation by the introduction of radicals, excited ions, nanoparticles, etc. The tip 620 offers light directly at the working surface by sonoluminescence. By using this tip 620, use of a mechanical tool to drill out a portion of the tooth can be avoided. These advantages are common to other embodiments of the present invention.

In the embodiment of FIG. 6B, the insulating shrink tube 632 is removed on the right half of the center electrode conductor 624, i.e., the side closest to the liquid solution high pressure output end. The removal enables electrical coupling and cavitation within the portion of the tip 620 where the insulation was removed. Specifically, electrical coupling and cavitation take place where the insulating shrink tubing 632 has been removed.

FIGS. 18A-18E depict various views of an embodiment of the tip incorporating aspects of the embodiment of the tip in FIG. 6B.

Like the tip 620 in FIG. 6B, the embodiment of FIG. 6C can also be used in place of a standard drill in dental procedures, such as a root canal or cavity preparation. The tip 640 of FIG. 6C also features a single vent 663 output that assists in focusing the discharge. The tip 640 can be used to open up the crown of a tooth, thereby facilitating access to the inside of the tooth, access decayed or otherwise compromised material within a tooth, in order to gain access to the root canal.

Although the tip 620 of FIG. 6B and the tip 640 of FIG. 6C both feature a single vent a single vent 663 and additional similar components, the ground return tube 625 of the tip 640 of FIG. 6B also includes a number of angled surfaces 641a-641n at the working end of the tip 640. These angled surfaces 641a-641n facilitate increased focus of the cavitation/compression waves/cavitation produced particles etc. produced during operation of an embodiment of the device. Similar to focusing acoustic sound waves, the angled surfaces 641a-641n focus the resultants towards the single vent 663, further increasing resulting jet velocities. In further embodiments of the present invention, tips may include additional examples of non-planar outer surfaces in order to manipulate the jet velocities.

FIGS. 19A-19E depict various views of an embodiment of the tip incorporating aspects of the embodiment of the tip in FIG. 6C.

Referring to FIG. 6D, the tip 660 embodiment is a tip that can be used for cavitation and includes more than one angled vent 661a-661n along the shaft 662 and a vent 663 located at the apex 664 of the tip 660. In this embodiment, the vent angles are machined to correspond to the angles at which the root canal laterals enter/exit the root canal. This tip 660 can be used, in conjunction with the described handset, to ream, clean, open up, and disinfect a root canal. This tip 660 both removes debris and a small layer of inter root canal material along the root canal wall proximal to the tip 660 during operation. The vents 661a-661n offer irrigation along a maximum portion of the root canal at the same time.

In this tip 660, the insulating shrink tube 632 is removed in close proximity to the vent holes 661a-661d located at the working end, the right side in FIG. 6D, of the tip 660, which allows electrical coupling and cavitation in these locations. The embodiment of FIG. 6D also incorporates a number of vents 661a-661d into an outside surface of the tip, in this case, the ground return tube 625. The numbers of vents varies and the number and configuration of vents in the embodiments discussed are offered as examples.

Returning to FIG. 6D, as aforementioned, laterals in the center of the tooth exit/enter the root canal at approximately 90 degrees to the root canal, while laterals positioned towards the bottom of the root canal exit/enter the root canal at approximately 60 degrees. Thus, the vents in this embodiment are targeted to both these groups of teeth. In order to target the laterals in the center of the tooth, in the non-limiting example in FIG. 6D, the ground return tube 625 incorporates two to four angled vent holes 661a-661b to target the laterals in the center of the tooth, and two to four angled vent holes 661c-661d to target the laterals positioned toward the bottom of the root canal, in addition to a vent 663 located at the apex 664 of the tip 660. The orientation of vent holes directs the fluid directly into the angled laterals, which enter the root canal at the aforementioned specific angles (90 degrees in the middle of the root canal and 60 degrees towards the bottom of the root canal) and down the main root canal via the apex vent 663. In FIG. 6D, vents 661a-661b are angled at 90 degrees from a longitudinal axis and vents 661c-661d are angled at approximately 60 degree from the longitudinal axis (in this embodiment, the center electrode 624 defines the axis). In various embodiments of the present invention, ranges of angles are utilized to target the angled laterals. The laterals at a 60 degree angle are targeted utilizing vents that include, but are not limited to, vents that output at a 45-75 degree angle from the longitudinal axis. The laterals at a 90 degree angle are targeted utilizing vents that include, but are not limited to, vents that output at a 75-115 degree angle from the longitudinal axis. As aforementioned, depending upon the anatomical structure targeted and the cavity into which an embodiment of the device is at least partially inserted, the angles of the openings can vary anywhere from 0-180 degrees relative to a longitudinal axis.

One of skill in the art will recognize that by reconfiguring the angles in this tip 660, the functionality of the tip, including the irrigation properties, can be focused on different portions of the mouth of a dental patient. The angles incorporated into the embodiment of FIG. 6D are only offered by way of example.

An advantage of using this tip 660 during dental procedures is that it can eliminate the need for a mechanical tool to ream a portion of the tooth. The files presently used in more traditional root canal procedures are capable of breaking within a tooth and piercing the apex of the tooth (which leads to a variety of detrimental situations). By omitting the use of files and utilizing the tip 660 of FIG. 6D, the chance of this type of damage to the tooth being treated is minimized.

FIGS. 20A-20H depict various views of an embodiment of the tip incorporating aspects of the embodiment of the tip in FIG. 6D.

FIG. 6E is an example of how changing the number and orientation of vents in a tip utilized in embodiments of the present invention can affect the functionality of the invention. In FIG. 6E, the tip 670, incorporates three vents 661a-661c angled to output at 45-75 degrees, to target the 60 degree angle at which lateral canals enter/exit the primary root canal. Matching the angles at which the cavitation products exit the tip 670 to the actual angle of the lateral canals increases the instance of working fluid penetrating the lateral canals and hence, increases irrigation, etc. because the limited amount of vents produces a highly focused, angled and powerful jet of irrigation at the same angle as the lower lateral canals. As a result, by utilizing this tip 670, the invention becomes a precision tool capable of precise delivery of the aforementioned cavitation products. As with the previous tips, portion of the insulating shrink tube 632 are removed at the vents 661a-661c. There is also a vent 663 located at the apex 664 of the tip 670.

FIGS. 21A-21H depict various views of an embodiment of the tip incorporating aspects of the embodiment of the tip in FIG. 6E.

Referring to FIG. 6F, the tip 680 in this figure is another example of how changing the number and positioning of vents machined into a tip can affect the functionality of an embodiment of the invention. Embodiments of the tip, such as the one in FIG. 6E, are used to ream, clean, open up, and disinfect a root canal. This embodiment of a tip 680 both removes debris and a small layer of inter root canal material along the root canal wall proximal to the tip 680 during operation.

Although the number and placement of vents can vary, in FIG. 6F, the non-limited example tip 680 incorporates eight angled vents 661a-661h (angled to output at 75-115 degrees) in the ground return tube 625 and a vent 663 located at the apex 664 of the tip 680. The 75-115 degree orientation of vent holes, which include a 90 degree orientation, in this embodiment of an aspect of the present invention, directs irrigants, including but not limited to, water, directly down via the apex vent 663 and at 90 degrees from the tip 680, thereby facilitating a movement of working fluid directly down the root canal and perpendicular to the canal wall. This tip 680 offers irrigation along a maximum portion of the root canal at the same time. Additionally, the vents 661a-661h in the ground return tube 625 directs cavitation produced products, such that they exit the tip 680 at 90 degrees from the tip 680. Thus, by utilizing this type of tip 680, embodiments of the present invention become precision tools capable of precise delivery of the cavitation products.

FIGS. 22A-22G depict various views of an embodiment of the tip incorporating aspects of the embodiment of the tip in FIG. 6F.

As aforementioned, the spacing of the electrodes in the embodiments of the tip may contribute to the functionality of the tip. Additionally, varying the size of the ground return tube, the size of the center electrode, and the distance of the center electrode from the nearest point of the ground return tube, may affect the power settings of the device as a whole. Table 1 below is an example of the power settings achieved by varying the size the center electrode and of the shortest distance between a given center electrode and a given ground return tube (i.e., wall spacing).

The examples in the table below are a few non-limiting examples of spacings and sizes for certain embodiments of the tip. In these examples, a stainless steel tube of a consistent size is utilized as a ground return tube. Additionally, the stainless steel tube in the examples below is cylindrical. However, one of skill in the art will recognize that ground returns of different materials and of different shapes can be utilized to achieve the discharges discussed, including but not limited to, cavitation products. In fact, different shapes and sizes of various elements of the tip may adapt the device for different applications.

TABLE 1

| Example # | Ground Return Outer Diameter | Ground Return Inner Diameter | Center Electrode | Wall Spacing | High Power Setting/ Joules | Low Power Setting/ Joules |
|---|---|---|---|---|---|---|
| 1 | 0.028 in | 0.019 in | 0.017 in | .001 in | 1 | 26.45 m |
| 2 | 0.028 in | 0.019 in | 0.016 in | .002 in | 1 | 26.45 m |
| 3 | 0.028 in | 0.019 in | 0.012 in | .0035 in | 1 | 26.45 m |
| 4 | 0.028 in | 0.019 in | 0.010 in | .0045 in | 1 | 1.481 m |

Although in the embodiments of the tips in FIGS. 6B-6F, an insulation layer is in contact with the center electrode, this insulation layer, in further embodiments of the tip, can alternatively be coupled to the ground return. In these embodiments, the center electrode and the ground return, in contact with a conductive medium, would couple through perforations in this layer.

As aforementioned, an embodiment of the present invention can be used to create an irrigation system for Piezoelectric/Magnetostrictive scalars, like a water pik-type device with additional bactericidal benefits. In this application, water is pretreated before being expelled into the mouth of a patient.

Figure 7:
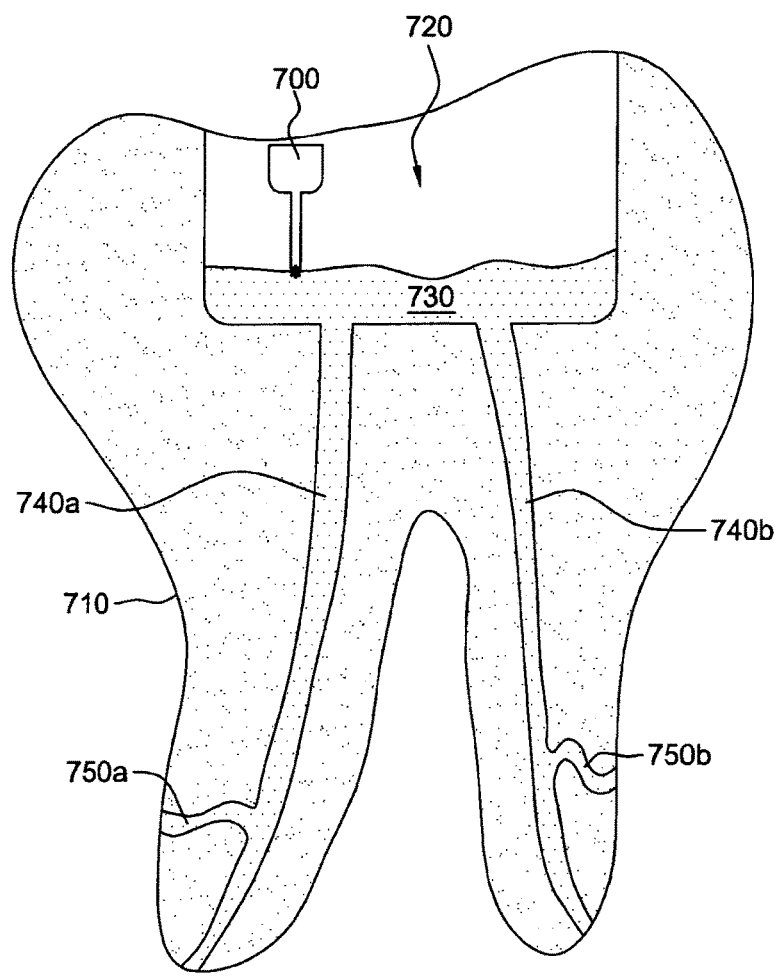
FIG. 7 depicts an aspect of an embodiment of the present invention.
Figure 8:
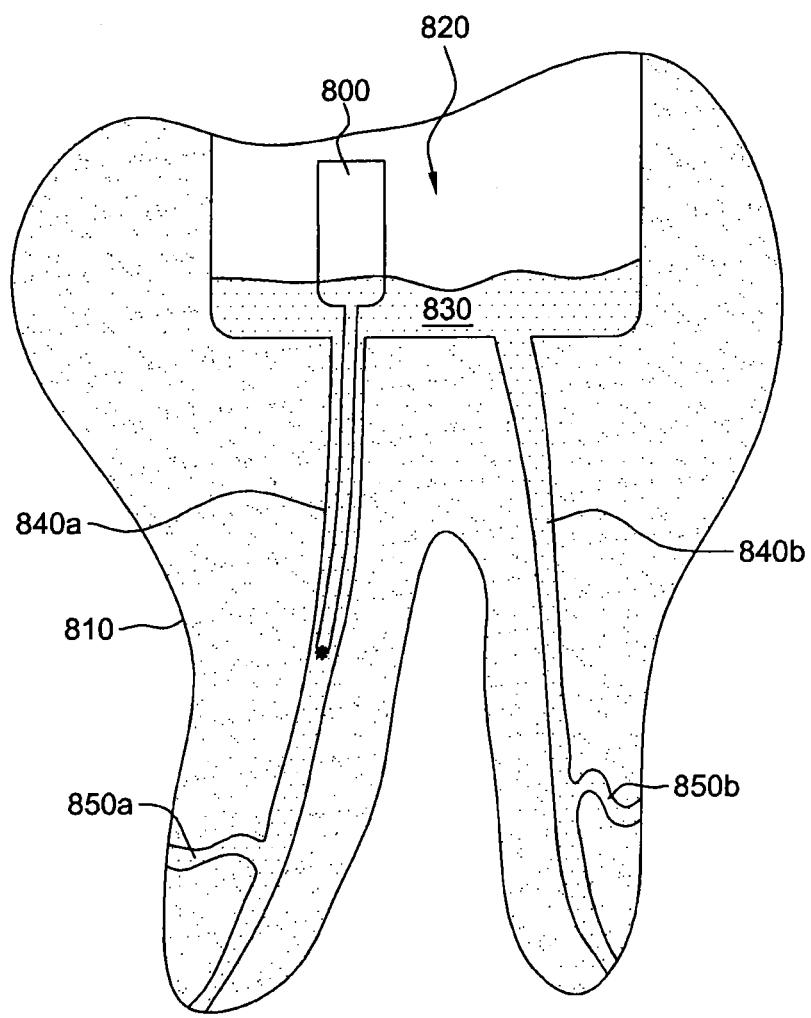
FIG. 8 depicts an aspect of an embodiment of the present invention.
Figure 9:
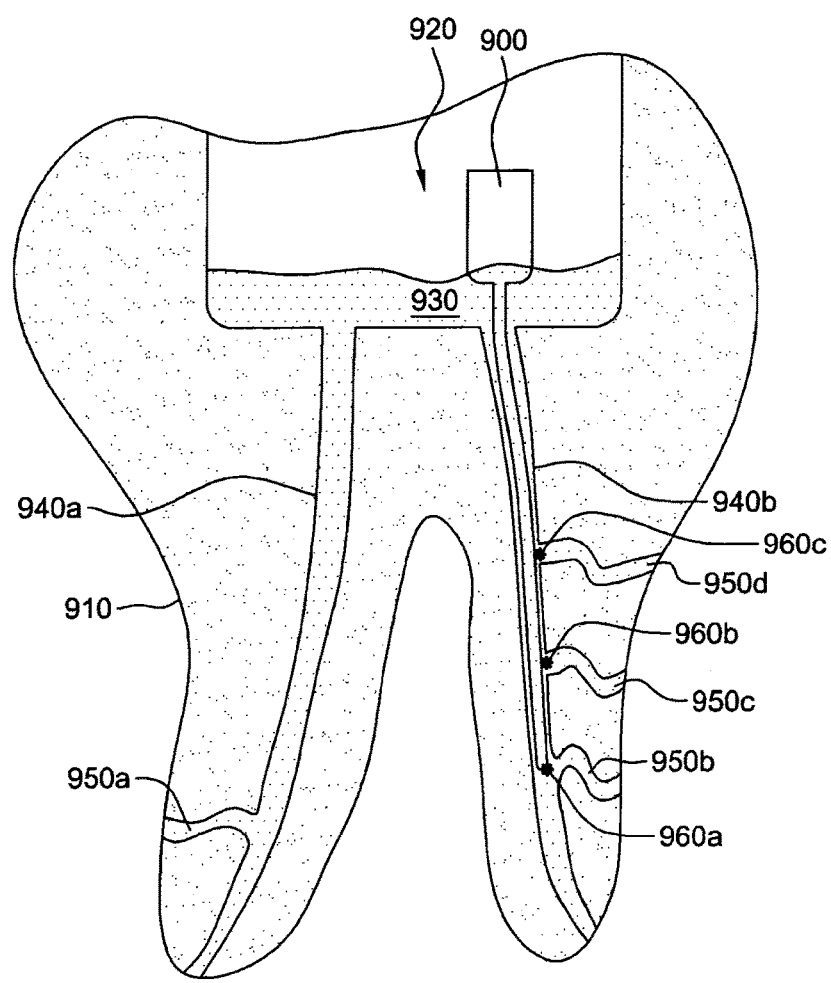
FIG. 9 depicts an aspect of an embodiment of the present invention.

FIGS. 7-9 illustrate the use of an embodiment of the present invention in irrigating canals and dental structures. These figures are merely meant to illustrate some possible positioning of one or more embodiments of the present apparatus during irrigation and are not meant to be exhaustive. One of skill in the art will recognize that the flexibility of the tip presents many possibilities for positioning which would be beneficial for the oral health of a patient.

Referring to FIG. 7, the tip 700 in an embodiment of the apparatus is positioned to fire a discharge at the surface, above the surface, or below the surface of the irrigant's fluid level 730, in both orientations, providing a working fluid within the tip chamber to complete the circuit. When the tip fires, it contains working fluid, which acts a dielectric, completing the circuit, which enables the electrical discharge, cavitation etc. As discussed earlier, the electrical discharge from the tip 700 has an anti-microbial effect even when discharges above the fluid level 730.

Although conductive fluid, such as dielectric fluid, is used as an example in various embodiments of aspects of the invention described, one of skill in the art will recognize that any conductive medium, including but not limited to liquid mediums, is useable with an embodiment of the present invention provided that it is able to conduct the charge as previously described. Further embodiments of the present invention may incorporate tips that utilize vapor, air, and/or gas as conductive mediums within the tips.

Returning to FIG. 7, to position the tip 700, the main coronal chamber 720 of the tooth 710 has been opened surgically. With the main canals and lateral canals. In this figure, both the main canals 740a-740b and lateral canals 750a-750b are visible.

Referring to FIG. 8, the firing tip 800 of an embodiment of the apparatus in placed below the fluid line 830, in fact, the tip 800 is submerged. The tip 800 is being fired in a main canal 840a, but given its flexibility, the tip 700 can also be fired in the vicinity of and/or in the lateral canal 850a. The firing tip 800 is not drawn to scale and in an embodiment utilized in practice is preferably long enough to approach the apex or the laterals, i.e., physically long enough to reach the apex of the tooth.

Referring to FIG. 9, the progression of a tip 900 of an embodiment of the present invention through a main canal 940b wherein it discharges at three different discharge sites 960a-930c, which are adjacent to three lateral canals 950b-950d is shown. The firing tip 900 and probe (not pictured) are moved down the main canal 940b to three lateral canals 990b-950d. As the tip 900 moves up and down the main canal 940b, firing discharges 960a-960c along the laterals 950b-950d, the UV, ozone, shock wave, radicals, and ions pulse directly into the lateral openings for full force and effect. A saline solution is useful in this embodiment because it conducts these particles to their destinations and has advantageous dielectric breakdown behavior as the saline acts as a dielectric solution which completes the circuit. However, as aforementioned, irrigants that can be used include, but are not limited to saline solution, hydrogen peroxide, glutaraldehyde, and/or any antibiotic and/or anti-microbial solution.

For certain applications of the present invention, pretreating the water and/or liquid by collecting it in an internal or external reservoir is advantageous. Such applications include, but are not limited to, ultrasonic scalars such as Piezoelectric and/or Magnetostrictive scalars, sonic scalars, and water piks. Meanwhile, for some applications, locating electrodes in the tip is sufficient to treat the water and/or liquid. In embodiments of the present invention utilized as water piks, Piezo/Magneto ultrasonic devices, and/or irrigation, including irrigation of periodontic wound sites, the locations of the electrodes utilized to pulse the water and/or liquid include, but are not limited to a reservoir internal or external to the handle of the embodiment of the device, and/or in the tip of the embodiment of the device.

Such applications include, but are not limited to, ultrasonic scalars such as Piezoelectric and/or Magnetostrictive scalars, sonic scalars, and water piks. FIGS. 10-16 are embodiments of the present invention that utilize electrodes in an external reservoir, in an internal reservoir, and/or in the tip of an embodiment of the device to treat the water and/or liquid to be utilized in the intended procedure.

Figure 10:
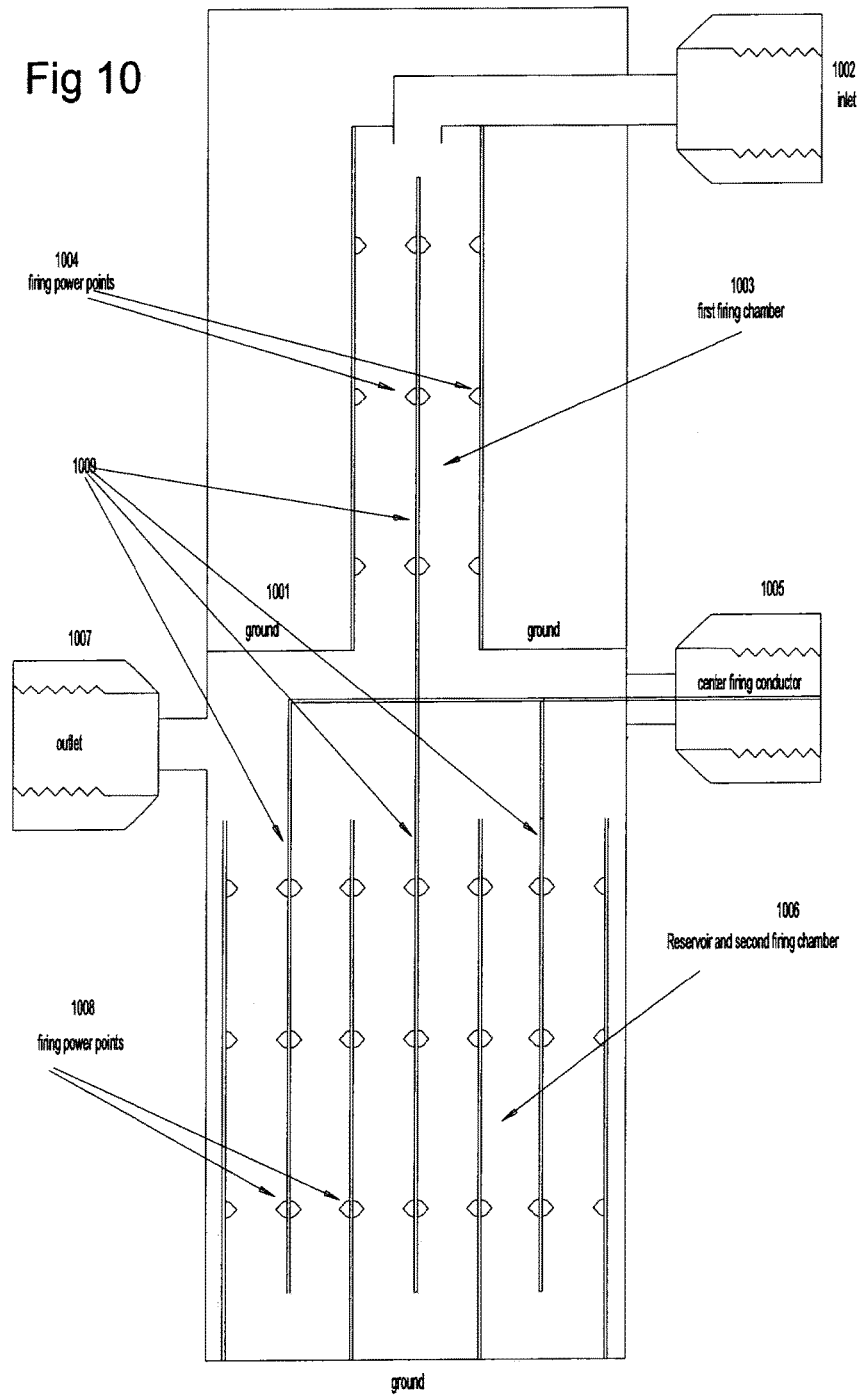
FIG. 10 depicts an aspect of an embodiment of the present invention.

FIG. 10 is an example of a standalone unit embodiment of the present invention that can be utilized as a Piezoelectric and/or Magnetostrictive scalars. Water is moved through the device and while inside, the water is treated through the dispersion of firing discharges, including but not limited to, UV, ozone, shock wave, radicals, and ions pulse. Thus, the water that exits the device carries with it bactericidal benefits. In the embodiment of FIG. 10, water and/or another liquid to be treated with spark discharges is moved through the device from the inlet 2, and out through the outlet 7, after being treated with electrical pulses.

In the embodiment of FIG. 10, water is channeled through the inlet 1002, where it progresses into a first firing chamber 1003, which is not storing liquid at this time. Firing points 1004 are positioned throughout this first firing chamber 1003 as well as the second firing chamber 1006. The multiple firing points 1004 save energy consumption because the area within the embodiment can be large. Thus, utilizing multiple firing points 1004 can translate to a cost savings because less energy is required to create the pulse.

The water and/or liquid progresses from the first treatment chamber 1003, into a second firing chamber 1006, which contains a reservoir where the water and/or liquid is stored. The second firing chamber 1006 also contains a group of firing points 1008, distributed within the reservoir. The water and/or liquid is treated by pulsed discharges in this second firing chamber 1006 before it moves through the outlet 1007, which can be understood as a "feed tube" to an used in the irrigation. The firing points 1008 provide the water and/or liquid with exposure to the pulse discharges in an attempt to achieve an 100% pathogen kill before the water and/or liquid leaves the second firing chamber 1006 and into the outlet 1007 to the end of the irrigation device.

In an embodiment of the present invention, the reservoir in the second firing chamber 1006 can be removed from the device and sterilized separately for further bactericidal benefit.

Given that this tip and/or electrode is utilized to treat a reservoir of water and/or liquid, it is also useful for water purification for non-dental health purposes. For example, it can be used to inject bactericidal properties into drinking water as a type of high efficiency filter.

In embodiments of the present invention utilized as water piks, Piezo/Magneto ultrasonic devices, and/or irrigation, including irrigation of periodontic wound sites, the locations of the electrodes utilized to pulse the water and/or liquid include, but are not limited to, the first firing chamber 1003, the second firing chamber 1006, and/or a reservoir in the handle of the embodiment of the device. When utilized for ultrasonic uses, an embodiment of the present invention utilizes a reservoir in the handle, rather than in the tip. The description of FIG. 10 can be applied to understand the functionality of the aspects of the embodiments described in FIGS. 11-16.

Figure 11:
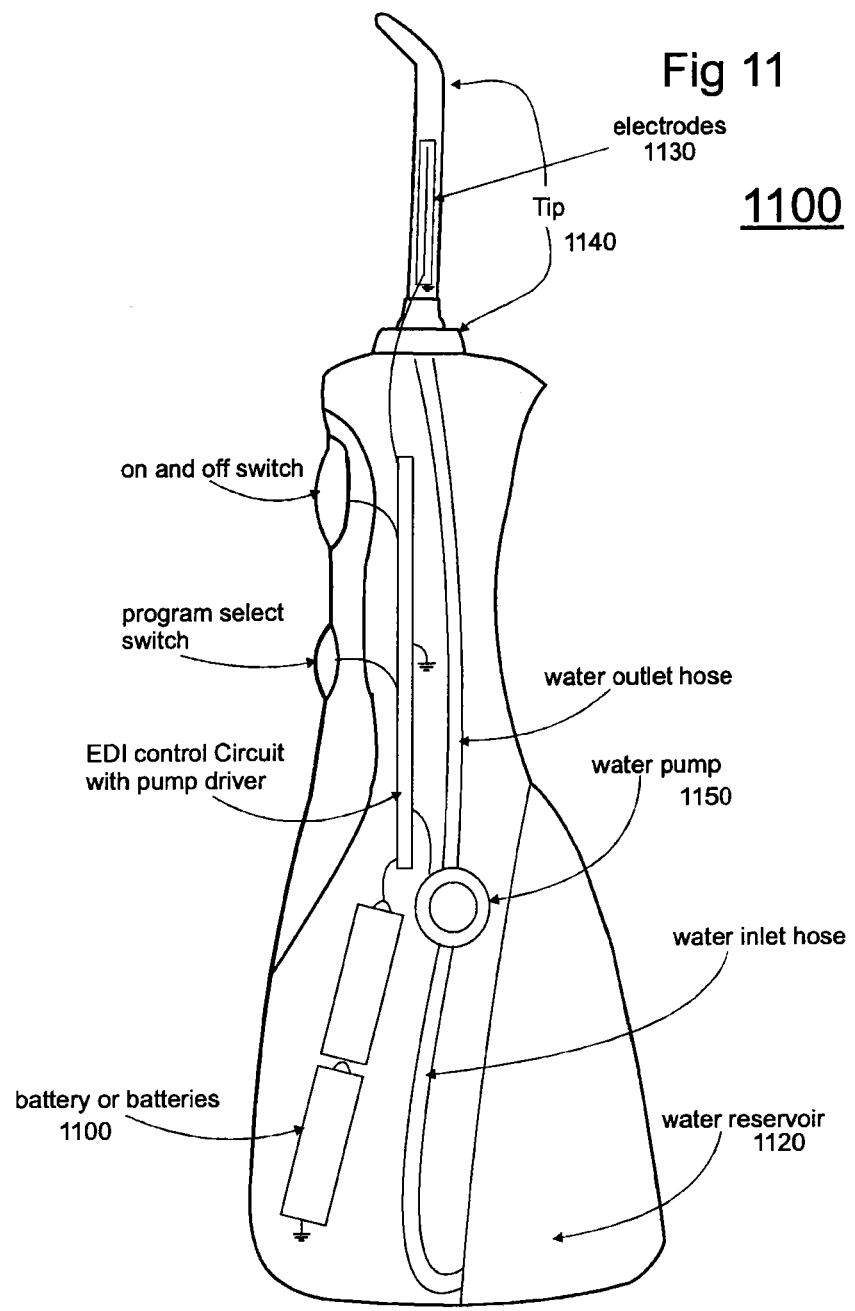
FIG. 11 depicts an aspect of an embodiment of the present invention.

Referring to FIG. 11, an embodiment of the present device 1100 that can be utilized as a water pik and/or a Piezo/Magneto ultrasonic device. Batteries 1110 serve as the power source in this device 1100. This embodiment of the device 1100 utilizes a single reservoir 1120 for holding and liquid and/or water that will be treated before moves from the tip to the patient's mouth. One set of electrodes 1130 in the tip 1140 of the device 1100 provide the electrical discharge to treat the water and/or liquid before it leaves the tip. The device 1100 is additionally powered by one or more PC boards (not pictured). The water pump 1150 is driven by one or more microcontrollers (not pictured).

In a subset of embodiments of the present invention, such as device 1100, a ceramic conductive substrate can be utilized for the electrodes. This type of electrodes is particularly effective when the water and/or liquid cannot be treated over a period of time in the apparatus, for example, within a reservoir before being released into an area that is being treated. The ceramic conductive electrodes can create a pulse that creates the desired anti-pathogenic effects over a short period of time and when a large volume of water is flowing through an area where the spark discharge is created in a short period of time. In the device 1100, the water and/or liquid is pumped through the tip 1140 and only treated by electrodes in that tip 1140. Thus, there is a short window for the electrical discharge.

In another example, in a scalar application, water and/or liquid is pumped through the tip rapidly and under pressure. In an embodiment of the scalar application, a reservoir of water and/or liquid is pumped to different rooms in a dental office. The high volume and pressure flow does not allow for much time to release the electrical discharge into the liquid and/or water before it is directed into a treatment area. By using one or more ceramic conductive substrates, the desire pathogen kill rate is achieved within the shortened period of time for a large volume of water and/or liquid with a high pressure.

Figure 12:
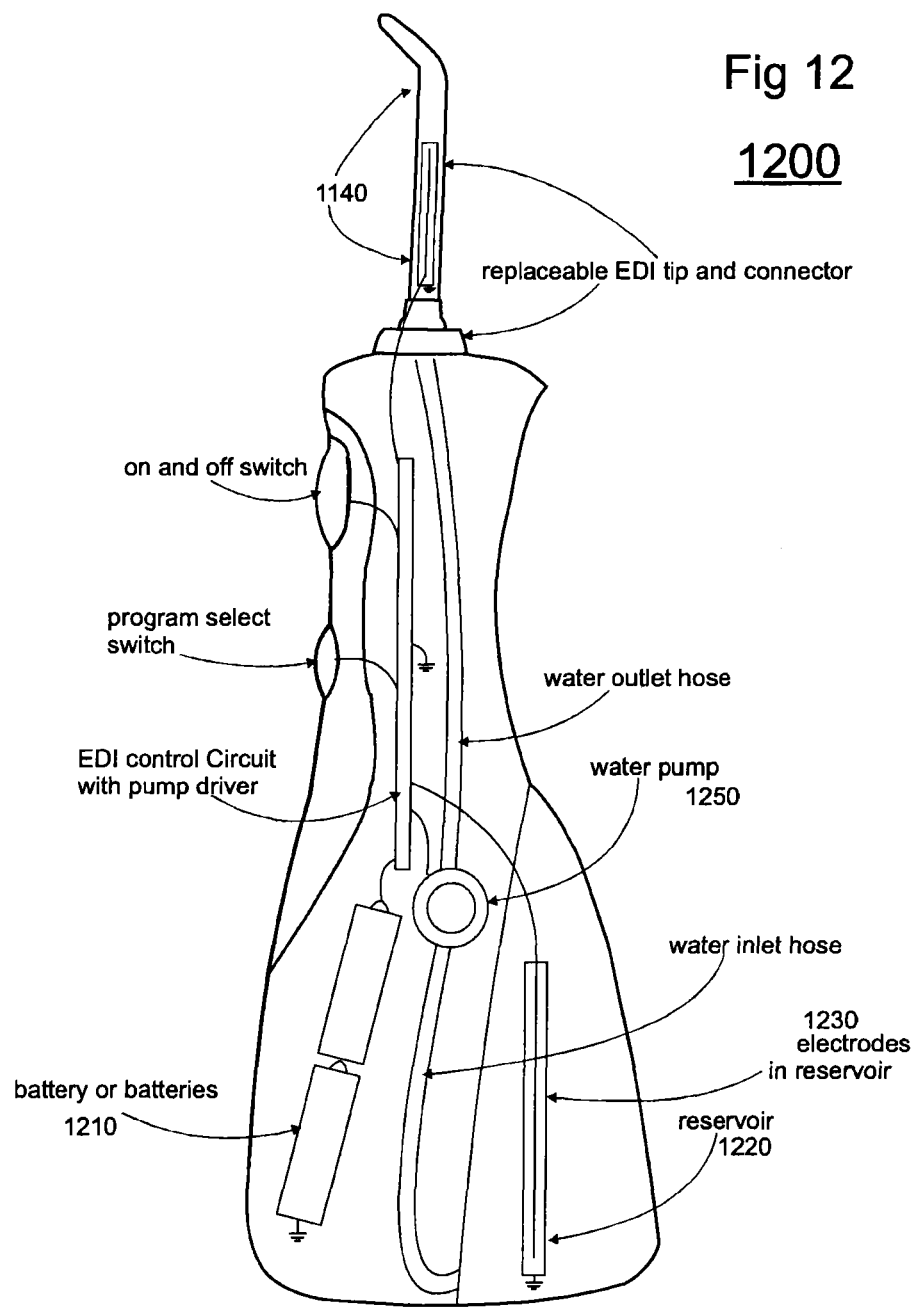
FIG. 12 depicts an aspect of an embodiment of the present invention.

Unlike in the device 1100 of FIG. 11, in FIG. 12, the water and/or liquid to be applied is treated in a reservoir, which allows for a longer treatment time. Similar to FIG. 11, FIG. 12 is an embodiment of the present device 1200 that can be utilized as a water pik and/or a Piezo/Magneto ultrasonic device, operates on batteries 1210, has a single water reservoir 1220, PC boards (not pictured), a water pump 1250, and is driven by at least one microcontroller (not pictured). However, in this device 1200, the electrodes that provide the electrical discharge to treat the water and/or liquid, actually reside in the reservoir 1220. Thus, the amount of time that the electrodes can treat the water and/or liquid is increased.

Figure 13:
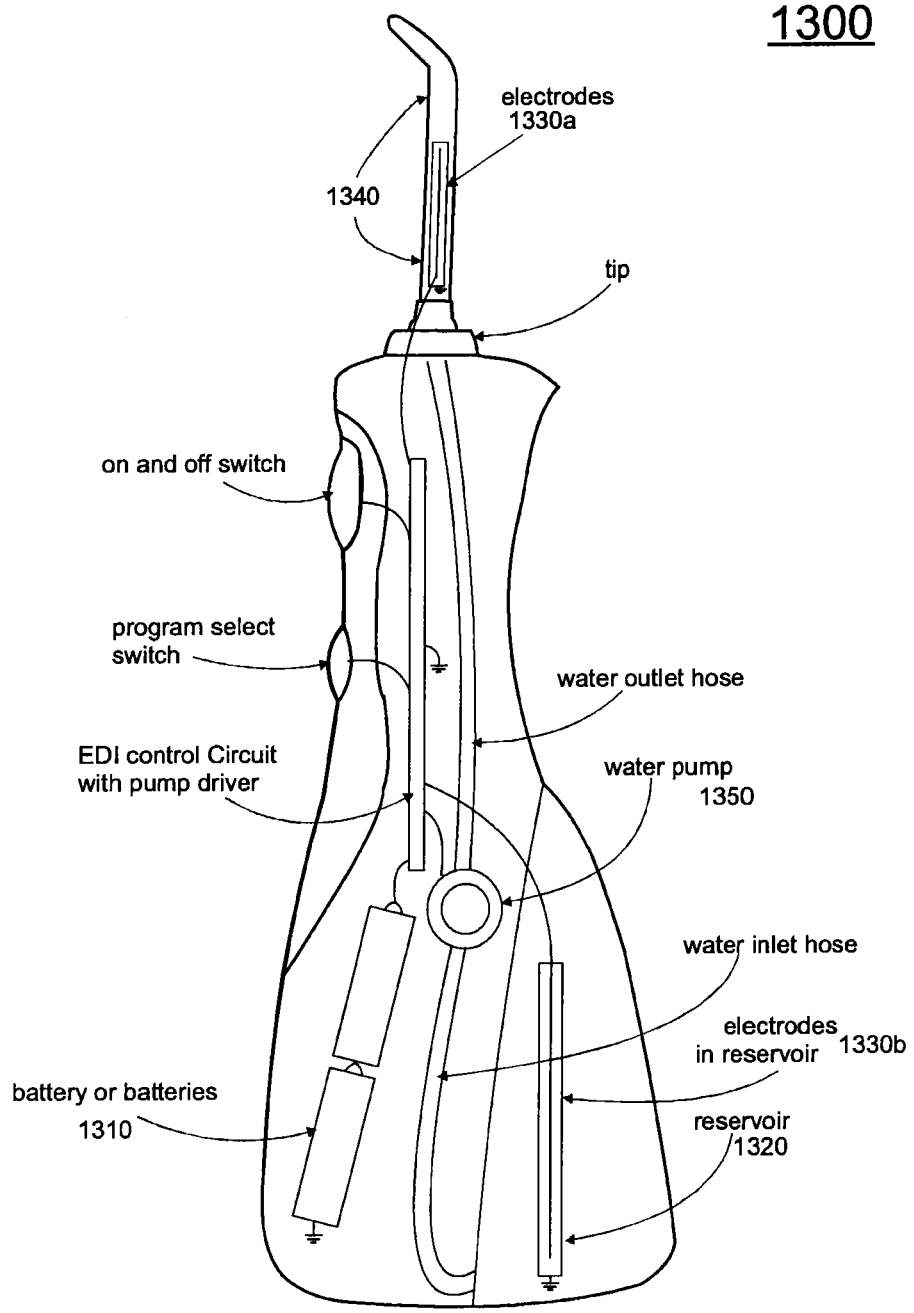
FIG. 13 depicts an aspect of an embodiment of the present invention.

FIG. 13 is another embodiment of a device 1300 that can be utilized as a water pik and/or a Piezo/Magneto ultrasonic device in accordance with at least one aspect of the present invention. In this embodiment, electrodes discharging the spark pulse to treat water and/or liquid are placed in both the tip 1340 and the reservoir 1320. A first set of electrodes 1330b treats the water and/or liquid while it is in the reservoir 1320, which a second set of electrodes 1330a treats the water and/or liquid as it exists the device 1300.

Figure 14:
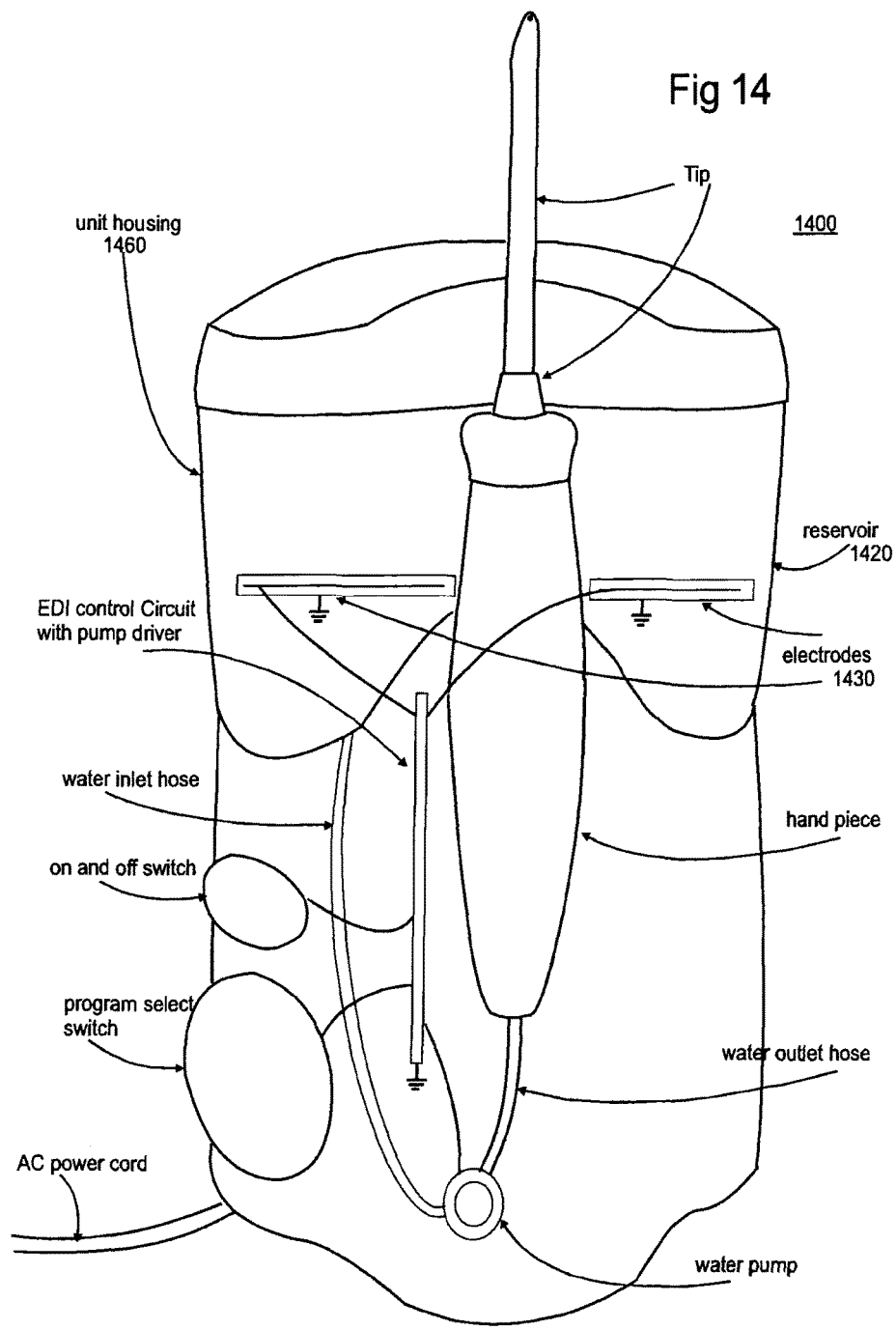
FIG. 14 depicts an aspect of an embodiment of the present invention.
Figure 15:
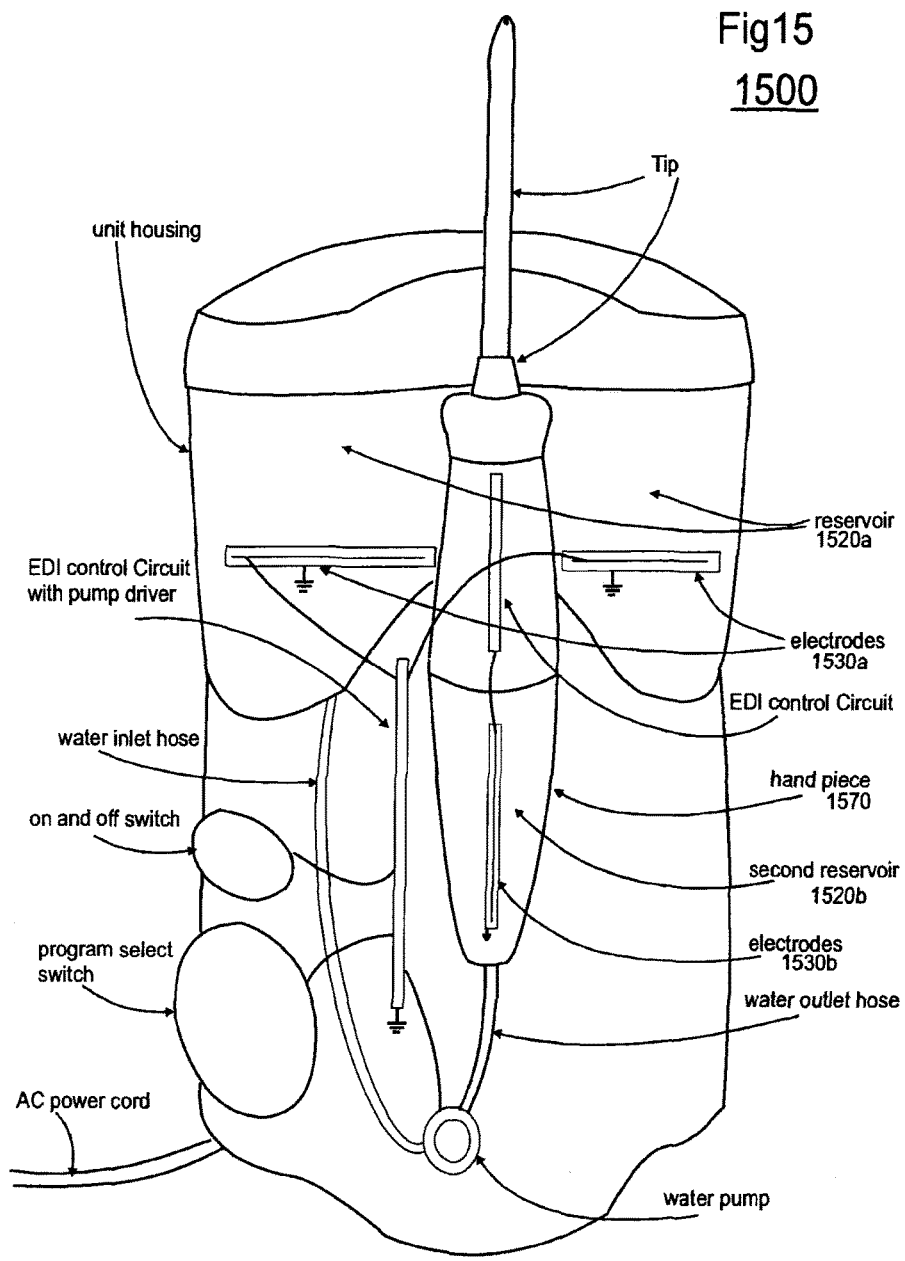
FIG. 15 depicts an aspect of an embodiment of the present invention.
Figure 16:
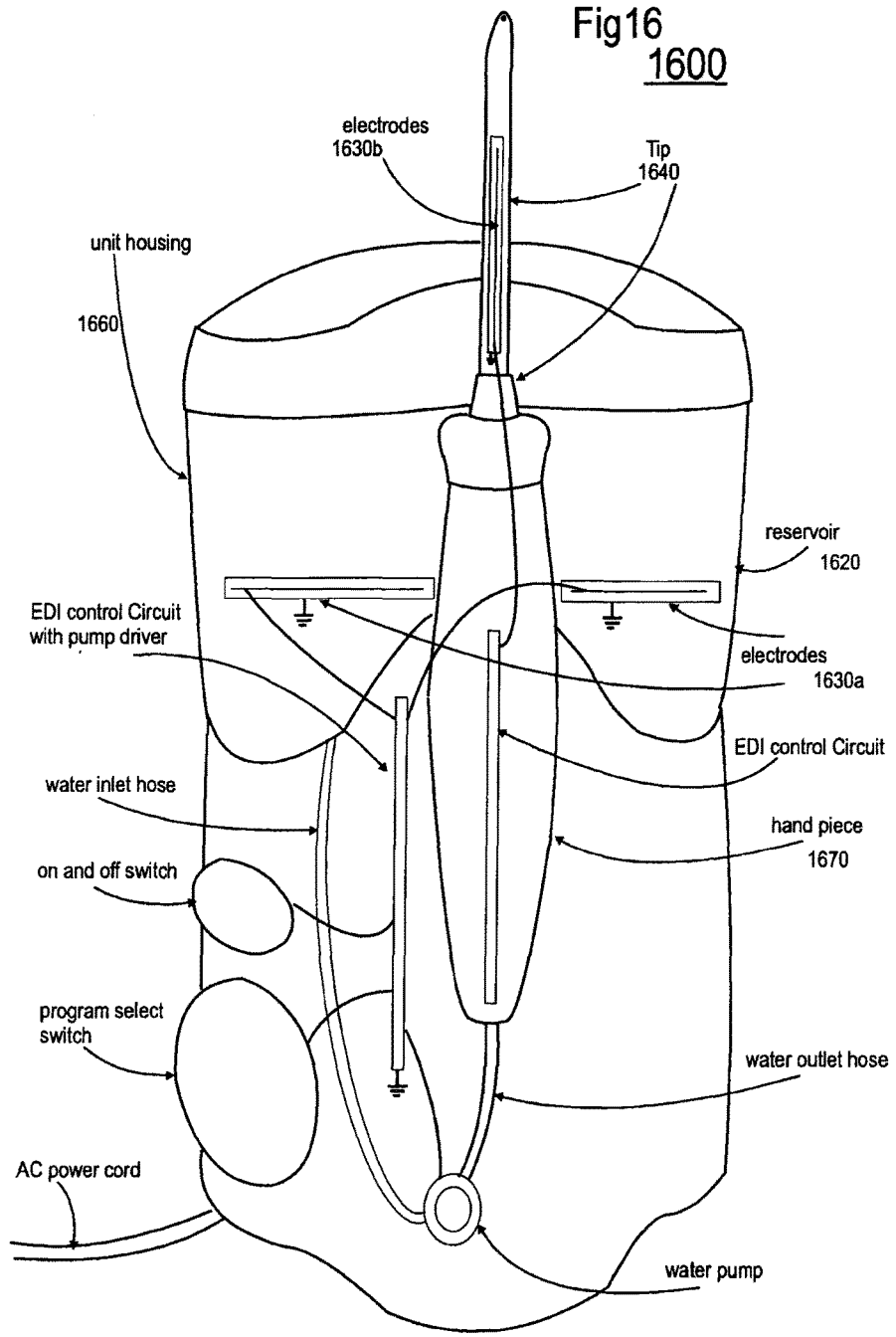
FIG. 16 depicts an aspect of an embodiment of the present invention.

FIGS. 14-16 are embodiments of the present invention that can be utilized as water piks, and/or a Piezo/Magneto ultrasonic devices. However, the devices in FIGS. 14-16 utilize an AC line as a power source and have no batteries. The functionality of these embodiments is discussed in reference to FIGS. 4-5 and FIG. 10. FIG. 14 is an embodiment of the present invention 1400 with one reservoir 1420 in the unit housing 1460 and a set of electrodes in that reservoir 1430. The embodiment 1500 in FIG. 15 has two reservoirs, a first reservoir 1530a in the housing 1560, and a second reservoir 1530b in the hand piece 1570. Thus, the water and/or liquid is treated in the unit housing 1560 and again in the hand piece 1570. The embodiment 1600 in FIG. 16 treats the water and/or liquid twice as well, but rather than utilize a second reservoir in the hand piece 1670, in this embodiment, there is a second set of electrodes 1630b in the tip 1640. This embodiment of the device 1600 also utilizes a first reservoir 1620 with a first set of electrodes 1630a in the unit housing 1660.

FIGS. 11-16 are offered as examples of placements of electrodes with and without reservoirs in embodiments of the present invention and are not meant to be exhaustive. One of skill in the art will recognize that the placement of electrodes and/or reservoirs can vary in accordance with the principles of the present invention.

Figure 17:
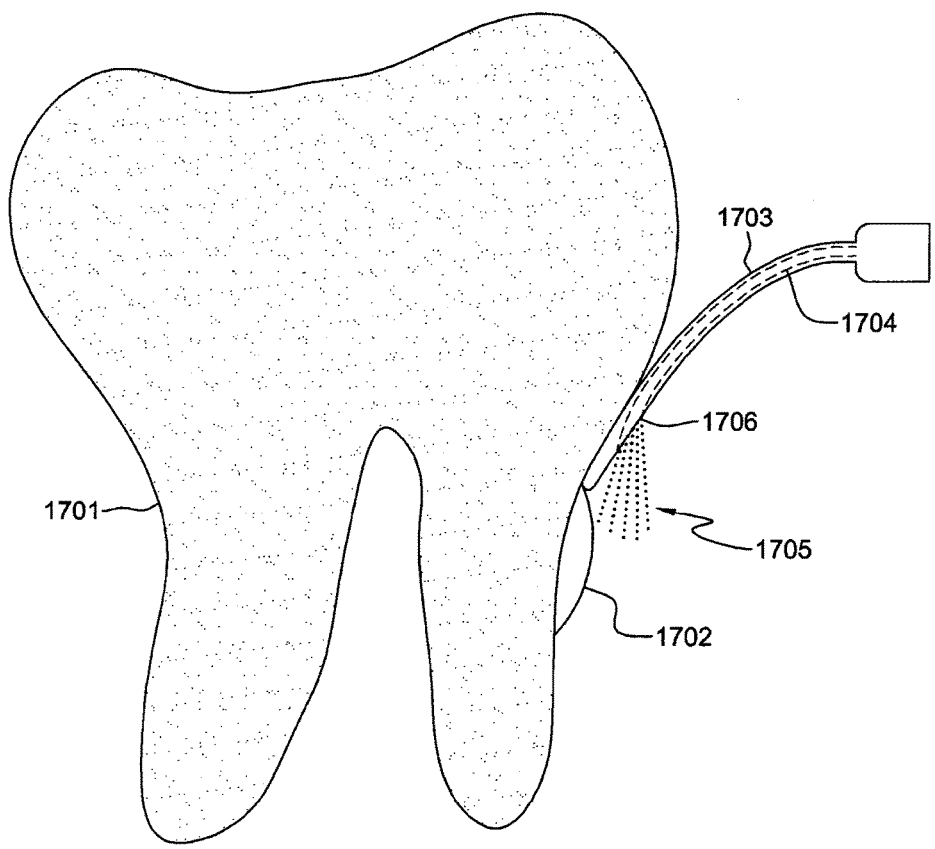
FIG. 17 depicts an aspect of an embodiment of the present invention.
Figure 18A:
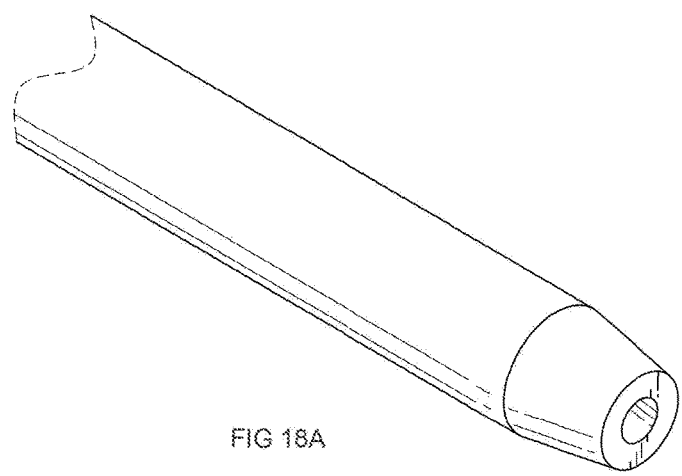
FIGS. 18A-18E depict aspects of an embodiment of the present invention.
Figure 18B:
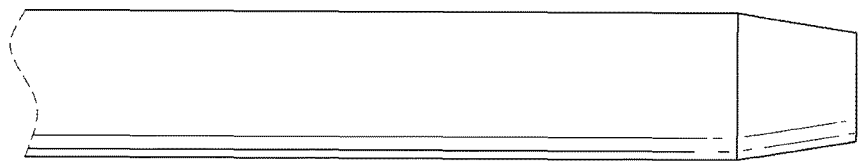
Figure 18C:
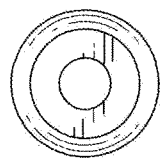
Figure 18D:
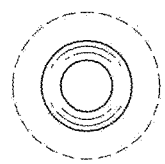
Figure 18E:
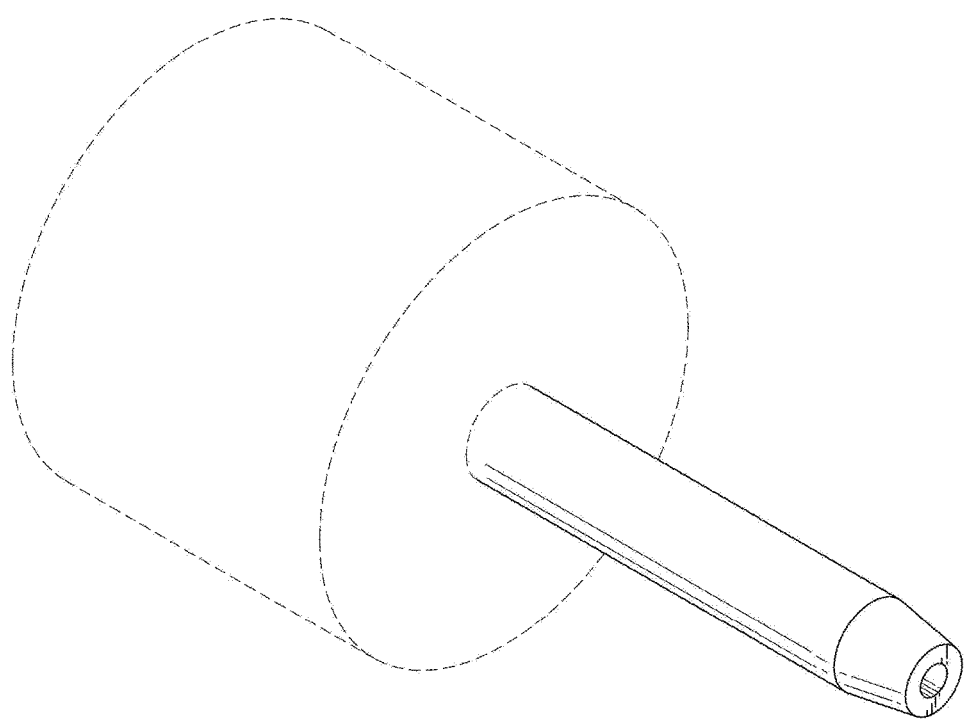
Figure 19E:
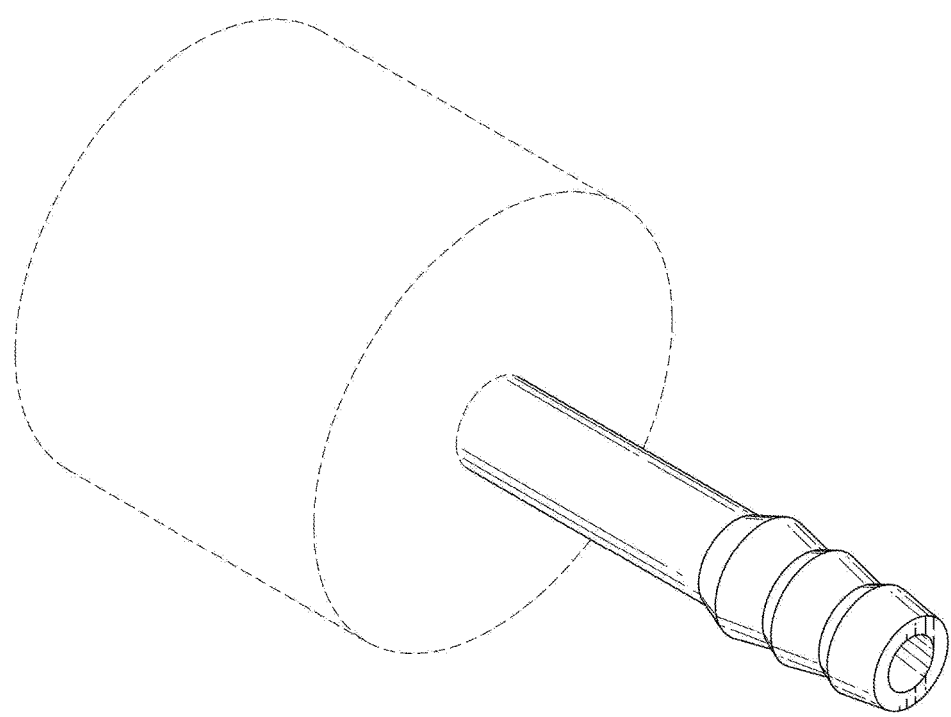
Figure 20A:
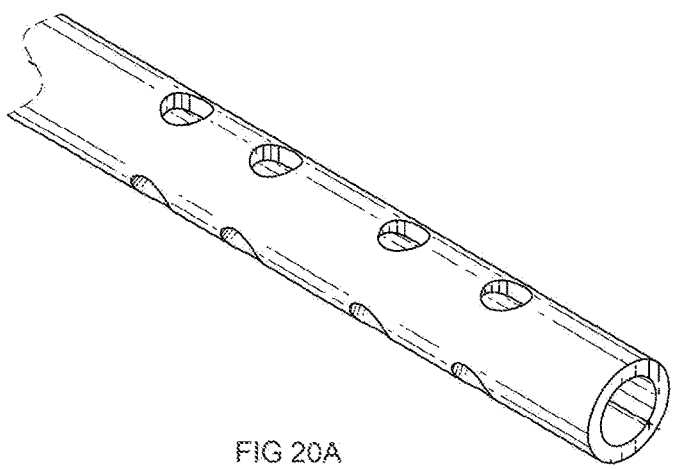
FIGS. 20A-20H depict aspects of an embodiment of the present invention.
Figure 20B:
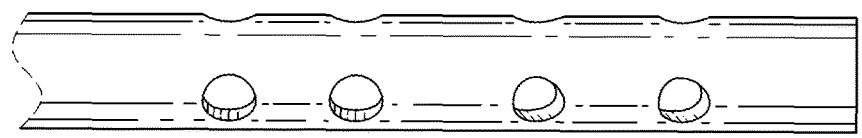
Figure 20C:
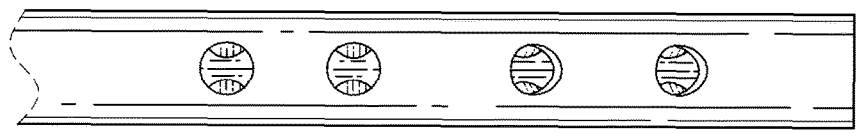
Figure 20D:
Figure 20E:
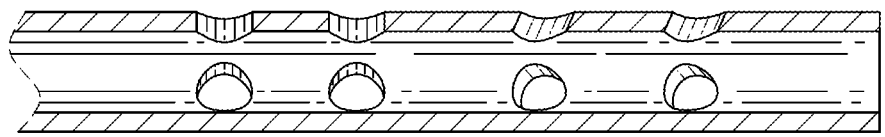
Figure 20F:
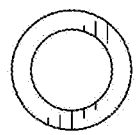
Figure 20G:
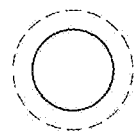
Figure 20H:
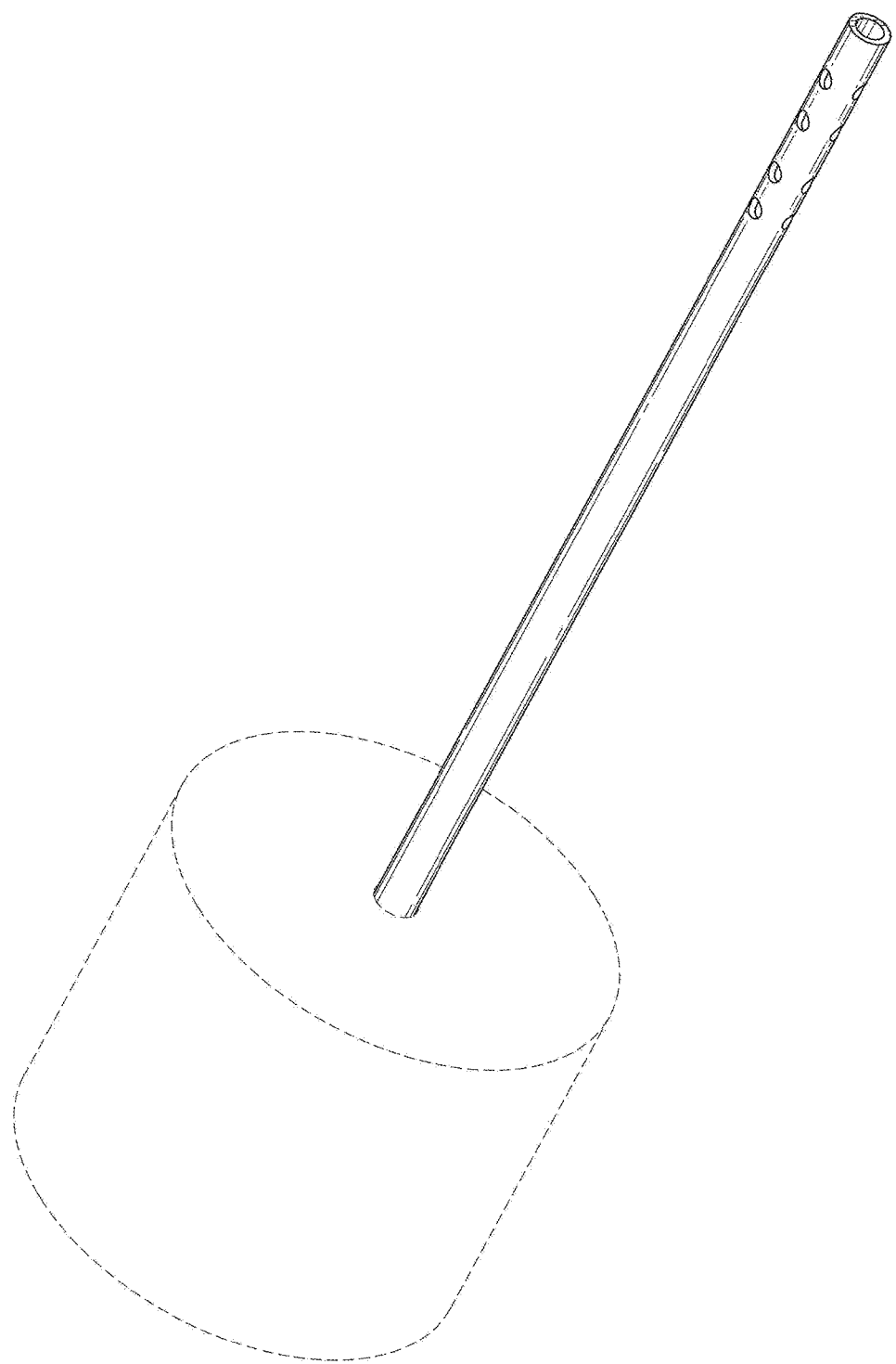
Figure 21A:
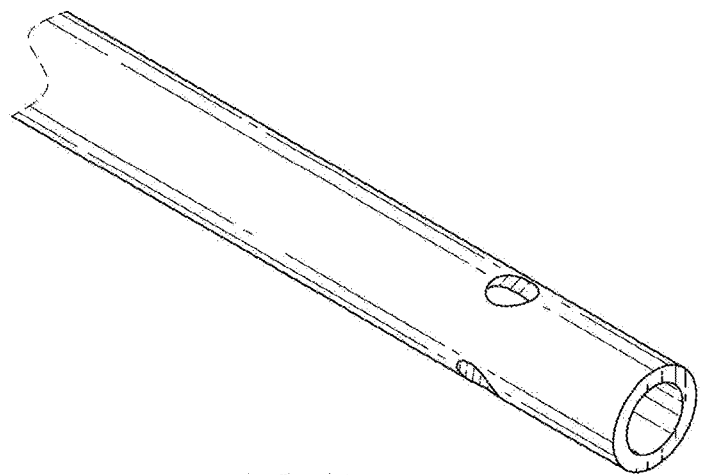
Figure 21B:
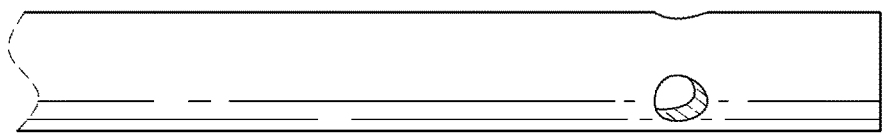
Figure 21C:
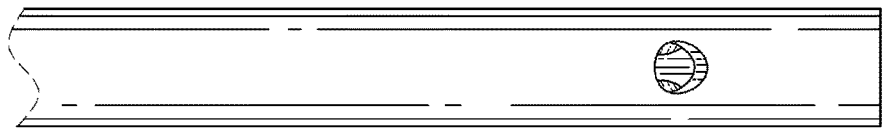
Figure 21H:
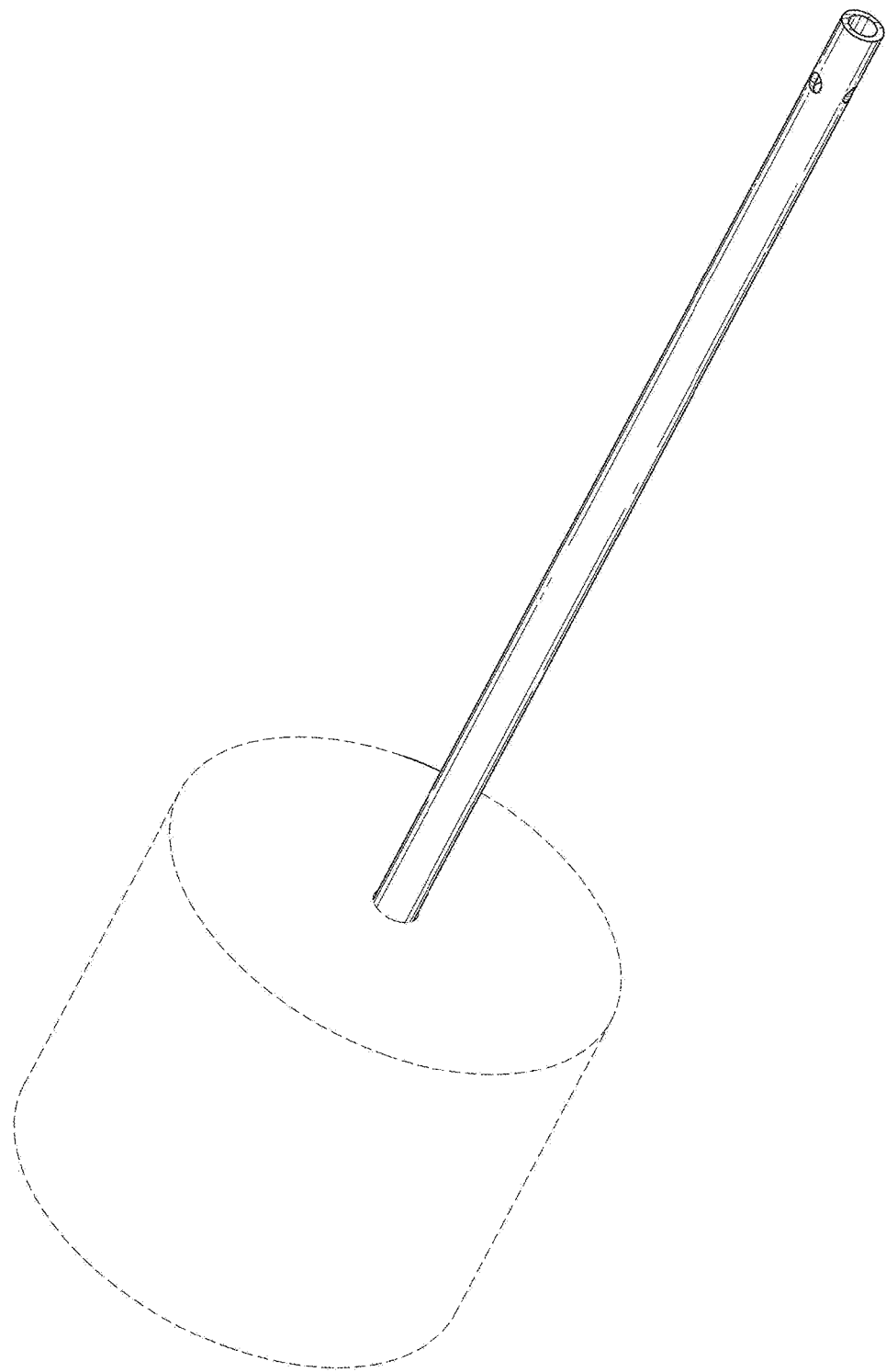
Figure 22A:
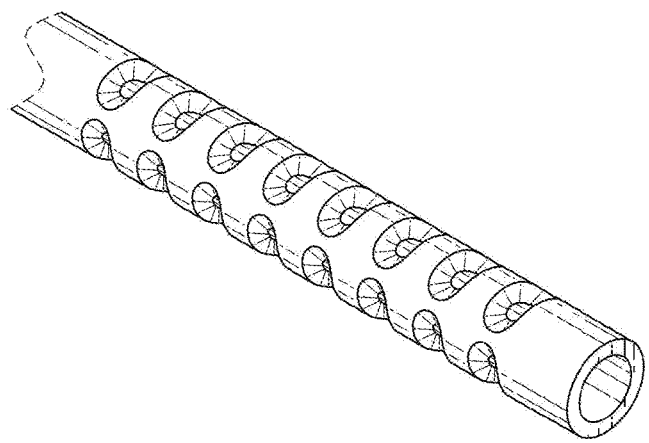
FIGS. 22A-22G depict aspects of an embodiment of the present invention.
Figure 22B:
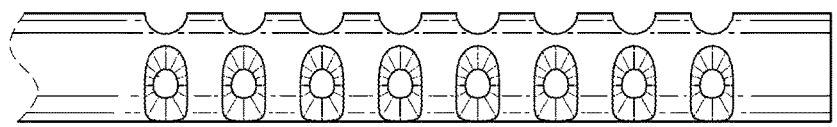
Figure 22C:
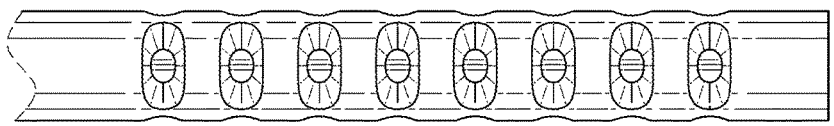
Figure 22D:
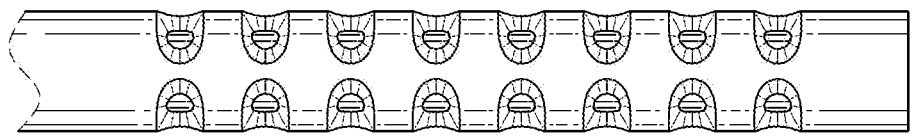
Figure 22E:
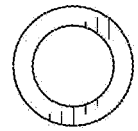
Figure 22F:
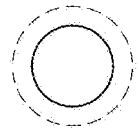
Figure 22G:
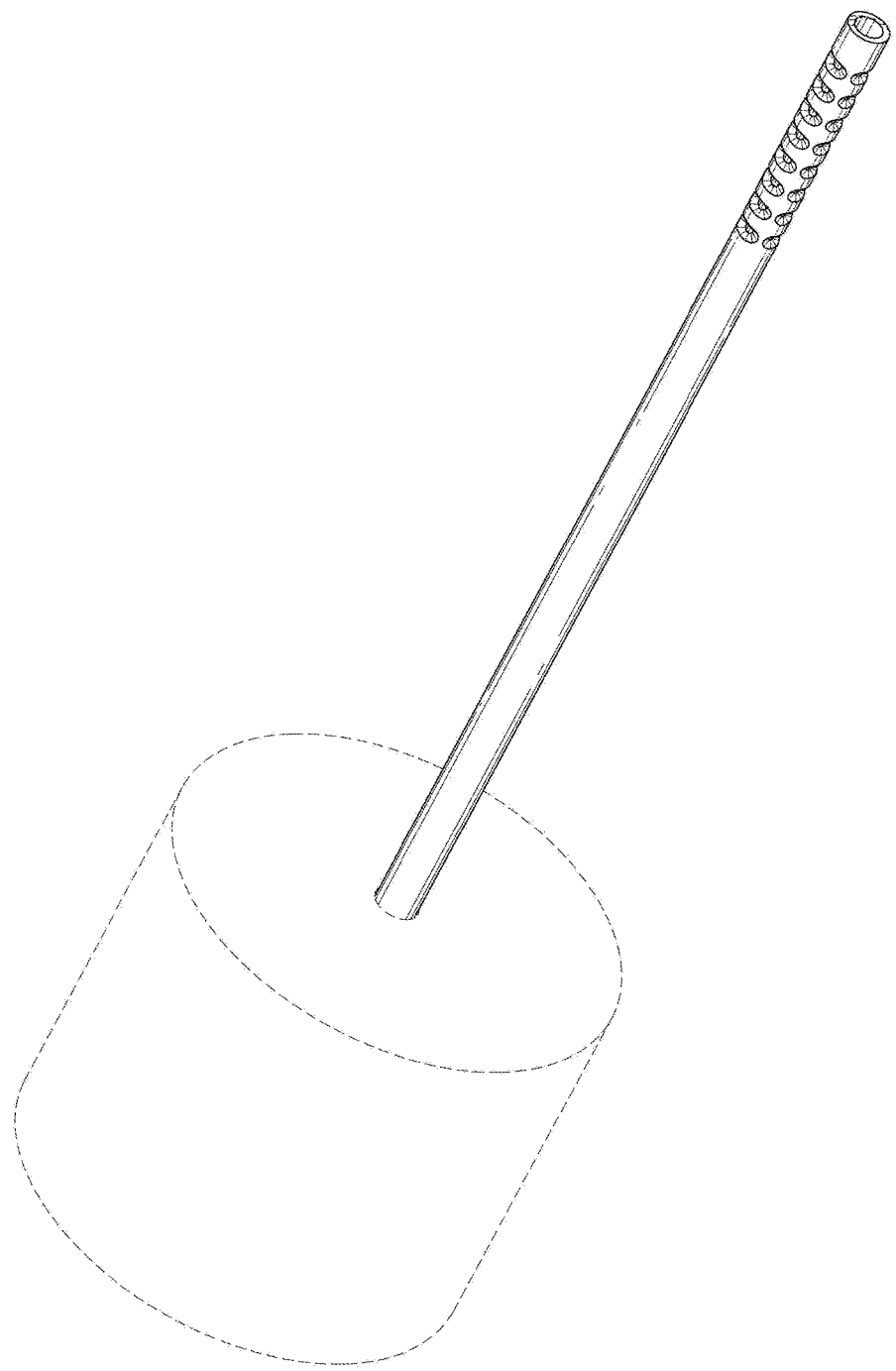

FIG. 17 demonstrates the use of an embodiment of the present application in an ultrasonic procedure. Referring to FIG. 17, a piezo/magneto tip 1703 is being utilized in accordance with the present method to treat the biofilm 1702 on a tooth 1701. Water progresses through the tip 1703 in the internal water line 1704 (which can be seen in FIGS. 11-16). Through the tip 1703, the treated water sprays 1705 from out of the device 1706 (partially pictured). In this embodiment, the water is not treated in the tip 1703, but rather in the hand piece and/or in a reservoir elsewhere in or connected to the device 1706 before in enters the tip 1703 and is utilized on the tooth 1701 and biofilm 1702.

An embodiment of the present invention is utilized in treating all water used in a dental office during various dental procedures. During dental procedures, water is often sprayed into the mouth while simultaneously being suctioned out. It is not desirable to allow a patient to swallow this water because the procedures expose pollutants in the mouth, which can be harmful to the health of the patient, if ingested. However, it is impossible to prevent all the water from being ingested and there may be pathogens in the water because the water system in the area where the dental office is located is not of a high quality. When an individual is being treated whose health is compromised, for example, an elderly patient, the pathogens from the water entering the now-exposed dental structures and/or being ingested by the patient, can harm the general health of this patient. Thus, an embodiment of the present invention can be utilized as part of the delivery system for any water dispensed into the mouth of a patient by a health professional. Embodiments used for this purpose utilize one to many reservoirs so that any dispensed water is treated with an electrical discharge before dispensed, even when it is immediately and almost simultaneously suctioned.

Another challenge related to water faced in a dental office (or other medical office) is the sterilization and/or purification of the water lines utilized. Pathogens in dental and/or medical water lines is a known problem and the FDA and ADA have both established guidelines for its reduction and/or attempted elimination. Embodiments of the present invention can be utilized to purify these water lines utilized in the aforementioned delivery system and/or other systems within a dental/medical environment.

An embodiment of the present invention can be used to create a treated water vapor that can be used to mist surfaces in a sanitary environment, such as an operating room. Rather than dispense the treated water/liquid, as fluid, an embodiment of the present invention dispenses the water as a mist, which is applied to surfaces. Because the bactericidal properties of the water and/or liquid that is pulsed with the electric discharge extends beyond the time that it is pulsed, the water/liquid can be used as a cleaning agent in a medical or other setting.

The cavitation processes and products created using embodiments of the present invention can be destructive to matter that they come into contact with. By utilizing tips configured for different uses, and selecting different power settings, embodiments of the present invention can assist in eradication of unwanted biological matter from different mediums. For example, embodiments of the present invention may assist in the eradication of unwanted microorganisms, such as E. Coli, from bodies of water.

Although the present invention has been described in relation to particular embodiments thereof, specifically embodiments that relate to dentistry, many other variations and modifications will become apparent to those skilled in the art. As such, it will be readily evident to one of skill in the art based on the detailed description of the presently preferred embodiment of the apparatus, system and method explained herein, that different embodiments can be realized. For example, an embodiment of the present invention is utilized to purify water, such as water located in the wilderness. This embodiment utilizes a battery or batteries and/or one or more solar cells as a power source. A further embodiment of the present invention is used in place of chlorine to eradicate microbes from a swimming pool. This embodiment is integrated into the swimming pool's existing cleaning system. Because there is no voltage leakage, the water can be enjoyed without fear of electrolysis. This embodiment can also utilize a battery or batteries and/or one or more solar cells as a power source.

Further contemplated integrations for embodiments of the present invention include, but are not limited to, cleaning and sterilizing other dental equipment, integrating an embodiment into a dishwasher for cleaning and disinfecting dishes, integrating an embodiment of the present invention into a home system for safe drinking water, integrating an embodiment into a tool to treat athlete's foot, integrating an embodiment into a disinfecting mop, and/or integrating an embodiment into a shower system that kills staff infections, funguses and other unwanted organic matter.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The invention claimed is:

1. An electrical discharge irrigation device, comprising:
a portable hand piece, the hand piece configured to be held or gripped by a single hand of a user, the hand piece comprising:
a power source to produce a first voltage;
a circuit coupled to the power source, the circuit configured to receive the first voltage from the power source and to convert the first voltage to a second voltage;
a discharge capacitor coupled to the circuit, the discharge capacitor configured to receive the second voltage from the circuit;

at least one of a transistor or a controlled rectifier coupled to the discharge capacitor configured to receive the second voltage; and a housing wherein the power source, the circuit, the discharge capacitor, and the at least one of a transistor and a controlled rectifier are encased in the housing; and an output tip coupled to the housing and coupled to the at least one of the transistor or the controlled rectifier, the output tip comprising:

a first end and a second end and a longitudinal axis extending between them;

an electrode located in an interior space of the output tip configured to receive an electrical charge from the at least one of a transistor and a controlled rectifier and to release an electric discharge; and a ground return located on an outside surface of the output tip, wherein a space between the electrode and the ground return comprises a conductive medium, the conductive medium being in contact with the electrode and the ground return to produce the electric discharge, wherein the second voltage is higher than the first voltage and the electrical discharge comprises a high current rate.

2. The device of claim 1, further comprising at least one opening on the outside surface of the output tip, wherein the electrical discharge creates waves within the conductive medium causing the conductive medium to exit the output tip through the at least one opening.

3. The device of claim 2, wherein the conductive medium that exits the output tip further comprises cavitation byproducts selected from the group consisting of: plasma, compression waves, UV radiation, UV light, hydrated electrons, OH radicals, $H_2O_2$, $H_3O$, $O_2$, $MnO_2$, $O_3$, O, $HO_2$, electrons, positive ions, negative ions, super oxides, nanoparticles, and anti-pathogens.

4. The device of claim 3, wherein the at least one opening is configured to direct the conductive medium that exits the output tip to target a specific anatomic structure when the output tip is inserted into a cavity of a patient.

5. The device of claim 4, wherein the at least one opening is configured at an angle greater than or equal to 0 degrees and less than or equal to 180 degrees relative to the longitudinal axis extending between the first end and the second end.

6. The device of claim 4, wherein the at least one opening is configured greater than or equal to 45 degrees and less than or equal to 115 degrees relative to the longitudinal axis extending between the first end and the second end.

7. The device of claim 2, wherein the at least one opening is at the first end of the output tip.

8. The device of claim 2, wherein the outside surface of the output tip is configured to be non-planar.

9. The device of claim 1, wherein the at least one of the transistor or the controlled rectifier is selected from the group consisting of: a high side low side MOSFET, an insulated-gate bipolar transistor, a silicon-controlled rectifier, a bipolar NPN transistor, a bipolar PNP transistor, and a Darlington transistor.

10. The device of claim 1, wherein output tip is detachable to the housing.

11. The device of claim 1, wherein a ground return is further located on an inner surface of the output tip, and wherein the electrode opposes the ground return at a distance.

12. The device of claim 1, wherein the output tip further comprises an insulating layer in contact with one of the electrode and the ground return, the insulating layer comprising at least one perforation, the at least one perforation defining an area for electrical coupling between the electrode and the ground return.

* * * * *